United States Patent
Dake et al.

(10) Patent No.: US 11,464,776 B2
(45) Date of Patent: *Oct. 11, 2022

(54) INHALABLE IMATINIB FORMULATIONS, MANUFACTURE, AND USES THEREOF

(71) Applicant: Aerovate Therapeutics, Inc., Boston, MA (US)

(72) Inventors: Ben Dake, Boston, MA (US); Ralph Niven, Portola Valley, CA (US)

(73) Assignee: Aerovate Therapeutics, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/874,153

(22) Filed: May 14, 2020

(65) Prior Publication Data

US 2020/0375895 A1 Dec. 3, 2020

Related U.S. Application Data

(60) Provisional application No. 62/984,037, filed on Mar. 2, 2020, provisional application No. 62/958,481, filed
(Continued)

(51) Int. Cl.

| A61K 9/00 | (2006.01) |
|---|---|
| A61K 47/26 | (2006.01) |
| A61K 31/501 | (2006.01) |
| A61K 31/506 | (2006.01) |
| A61P 11/00 | (2006.01) |
| A61K 38/18 | (2006.01) |

(Continued)

(52) U.S. Cl.
CPC .......... *A61K 31/506* (2013.01); *A61K 9/0073* (2013.01); *A61K 9/0075* (2013.01); *A61K 9/0078* (2013.01); *A61K 31/501* (2013.01); *A61K 38/1858* (2013.01); *A61K 38/193* (2013.01); *A61K 47/26* (2013.01); *A61P 9/12* (2018.01); *A61P 11/00* (2018.01); *C07B 2200/13* (2013.01)

(58) Field of Classification Search
CPC .. A61K 9/0073; A61K 9/0075; A61K 9/0078; A61K 31/501; A61K 47/26; A61K 38/1858; A61K 31/506; A61K 38/193; A61P 9/12; A61P 11/00; C07B 2200/13
See application file for complete search history.

(56) References Cited

U.S. PATENT DOCUMENTS

| 5,521,184 A | 5/1996 | Zimmermann |
|---|---|---|
| 7,507,821 B2 | 3/2009 | Anli et al. |

(Continued)

FOREIGN PATENT DOCUMENTS

| CN | 103910711 | * | 7/2014 |
|---|---|---|---|
| EP | 2582689 A1 | | 4/2013 |

(Continued)

OTHER PUBLICATIONS

Freyhaus, 2009, Significant improvement of right ventricular function by imatinib mesylate in scleroderma-associated pulmonary arterial hypertension, Clin Res Cardiol 98:265-267.
(Continued)

*Primary Examiner* — Jianfeng Song
(74) *Attorney, Agent, or Firm* — Brown Rudnick LLP

(57) ABSTRACT

The invention relates to inhalable imatinib formulations, manufacture, and uses thereof.

11 Claims, 54 Drawing Sheets

Related U.S. Application Data on Jan. 8, 2020, provisional application No. 62/948,408, filed on Dec. 2, 2019, provisional application No. 62/877,575, filed on Jul. 23, 2019, provisional application No. 62/849,054, filed on May 16, 2019, provisional application No. 62/849,056, filed on May 16, 2019, provisional application No. 62/849,058, filed on May 16, 2019, provisional application No. 62/849,059, filed on May 16, 2019.

(51) Int. Cl.
*A61K 38/19* (2006.01)
*A61P 9/12* (2006.01)

(56) References Cited

U.S. PATENT DOCUMENTS

| | | | |
|---|---|---|---|
| 7,638,627 | B2 | 12/2009 | Kankan et al. |
| 7,674,901 | B2 | 3/2010 | Szczepek et al. |
| 8,252,926 | B2 * | 8/2012 | Gunduz .............. A61P 35/00 544/295 |
| 9,925,184 | B2 | 3/2018 | Zisman |
| 2006/0223817 | A1 * | 10/2006 | Adin .................. C30B 7/00 514/252.18 |
| 2006/0275372 | A1 | 12/2006 | Jenkins et al. |
| 2008/0103305 | A1 | 5/2008 | MacDonald et al. |
| 2008/0181958 | A1 | 7/2008 | Rothrock et al. |
| 2008/0207904 | A1 | 8/2008 | MacDonald et al. |
| 2009/0136579 | A1 | 5/2009 | Egashira |
| 2010/0330130 | A1 | 12/2010 | Khunt et al. |
| 2011/0190313 | A1 | 8/2011 | Pascoe et al. |
| 2011/0275097 | A9 | 11/2011 | Singh et al. |
| 2011/0281867 | A1 | 11/2011 | Kalman et al. |
| 2011/0306763 | A1 | 12/2011 | Kamath et al. |
| 2012/0192861 | A1 | 8/2012 | Surber |
| 2013/0060030 | A1 | 3/2013 | Kompella et al. |
| 2013/0310424 | A1 | 11/2013 | Surber |
| 2015/0044288 | A1 * | 2/2015 | Surber .............. A61K 31/506 424/489 |
| 2015/0196543 | A1 | 7/2015 | Surber |
| 2017/0224706 | A1 | 8/2017 | Surber |
| 2018/0162837 | A1 | 6/2018 | Zisman |
| 2018/0263995 | A1 | 9/2018 | Schmidt et al. |
| 2018/0325917 | A1 | 11/2018 | Surber |
| 2019/0030012 | A1 | 1/2019 | Surber |
| 2019/0054076 | A1 | 2/2019 | Surber |
| 2020/0060968 | A1 | 2/2020 | Surber et al. |
| 2020/0306264 | A1 | 10/2020 | Surber |
| 2020/0405704 | A1 | 12/2020 | Surber |

FOREIGN PATENT DOCUMENTS

| | | | |
|---|---|---|---|
| WO | 2006/133046 | A2 | 12/2006 |
| WO | 2007/119601 | A2 | 10/2007 |
| WO | 2008/136010 | A1 | 11/2008 |
| WO | 2010/019540 | A1 | 2/2010 |
| WO | 2011/023146 | A1 | 3/2011 |
| WO | 2011/039782 | A1 | 4/2011 |
| WO | 2011/095835 | A1 | 8/2011 |
| WO | 2011/100282 | A2 | 8/2011 |
| WO | 2012/090221 | A1 | 7/2012 |
| WO | 2019/060463 | A2 | 3/2019 |

OTHER PUBLICATIONS

Ghofrani, 2005, Imatinib for the Treatment of Pulmonary Arterial Hypertension, N Engl J Med, 353(13):1412-1413.

Ghofrani, 2010, Imantinib in Pulmonary Arterial Hypertension Patients with Inadequate Response to Established Therapy, American Journal of Respiratory and Critical Care Medicine, 182:1172-1177.

Hoeper, 2013, Imatinib Mesylate as Add-on Therapy for Pulmonary Arterial Hypertension, Results of the Randomized IMPRES Study, 122 pages.

Novartis Study Shows QT1571 Significantly Improved Walking Distance in Patients with Life-Threatening Pulmonary Arterial Hypertension, 2011, 5 pages.

Schermuly, 2005, Reversal of experimental pulmonary hypertension by PDGF inhibition, J Clin Invest, 115 (10):2811-2821.

International Search Report and Written Opinion issued in International Application No. PCT/US2020/032872, dated Sep. 28, 2020, 16 pages.

International Search Report and Written Opinion issued in International Application No. PCT/US2020/032874, dated Jul. 21, 2020, 7 pages.

Kesely, 2016, Inhibition of an Erythrocyte Tyrosine Kinase with Imatinib Prevents Plasmodium falciparum Egress and Terminates Parasitemia, PLoS One, vol. 11, No. 10.

* cited by examiner

INHALABLE IMATINIB FORMULATIONS, MANUFACTURE, AND USES THEREOF

CROSS-REFERENCE TO RELATED APPLICATIONS

This Application claims the benefit of, and priority to, U.S. Provisional Application Nos. 62/849054, filed May 16, 2019; 62/849056, filed May 16, 2019; 62/849058, filed May 16, 2019; 62/849059, filed May 16, 2019; 62/877575, filed Jul. 23, 2019; 62/942408, filed Dec. 2, 2019; 62/984037, filed Mar. 2, 2020; and 62/958481, filed Jan. 8, 2020; the content of each of which is hereby incorporated by reference herein in its entirety.

FIELD OF THE INVENTION

The invention generally relates to inhalable formulations of imatinib, imatinib metabolites, imatinib salts, and their manufacture and uses.

BACKGROUND

Pulmonary arterial hypertension (PAH) is a condition involving elevated blood pressure in the arteries of the lungs with unknown causes and is differentiated from systemic hypertension. PAH is a progressive disease where resistance to blood flow increases in the lungs causing damage to the lungs, the pulmonary vasculature and the heart that can eventually lead to death. While symptoms are treatable with vasodilators and other medications, there is no known disease modifying therapy or cure and advanced cases can eventually require lung transplants.

Imatinib, especially the mesylate salt thereof, is a tyrosine kinase inhibitor approved for use in treating certain types of cancer. Imatinib's potential to inhibit the tyrosine kinase PDGFR (platelet-derived growth factor receptor) which is highly upregulated in the pulmonary arteries in cases of PAH, led to interest in its use in treating PAH. See, Olschewski, H, 2015, Imatinib for Pulmonary Arterial Hypertension—Wonder Drug or Killer Drug? Respiration, 89: 513-514, incorporated herein by reference. To that end, studies have been conducted to determine the potential of imatinib in treating PAH and patients have been found to respond favorably to said treatment. Unfortunately, an unacceptable amount of severe adverse events including subdural hematoma blunted enthusiasm for the drug. Frost, et al., 2015, Long-term safety and efficacy of imatinib in pulmonary arterial hypertension, J Heart Lung Transplant, 34(11): 1366-75, incorporated herein by reference.

SUMMARY

Compositions and methods of the invention address problems with imatinib-based PAH treatments through the use of specialized formulations and delivery mechanisms. Particularly, the invention provides a formulation of inhalable imatinib with a higher ratio of API (active pharmaceutical ingredient) than found in conventional formulations. In certain embodiments, formulations comprising 50% or more imatinib or imatinib salts are provided. Compositions and methods of the invention recognize that large volumes may be difficult or dangerous for patients to inhale and that, therefore, minimizing the amount of non-API components in the formulation can improve patient comfort, safety, and compliance by reducing the overall amount of compound that is inhaled while still providing a therapeutically effective API concentration in target tissue.

Furthermore, aerodynamic properties important to inhalable drug uptake can more easily be managed when less of the formulation is required for carriers or other additives. The performance of dry-powder formulations consisting of 50%, 75%, and 90% API was tested via aerodynamic particle size distribution, blend content uniformity, capsule content uniformity, and emitted dose by dosage unit sampling apparatus (DUSA) with favorable results as shown in Example 3 below. By providing functional inhalable formulations with high concentrations of imatinib or salts thereof, compositions and methods of the invention can provide the load-reducing benefits discussed above while still delivering therapeutic results and avoiding the severe adverse events associated with other drug delivery routes.

High-API ratio inhalable compositions of the invention offer greater lung exposure than equivalent doses of imatinib or imatinib mesylate administered through conventional oral routes or by IV. While a relatively high oral dose of imatinib or imatinib mesylate would be required to achieve the same target lung exposure as achieved by inhalation of the inventive formulations, significantly lower dosages can be delivered using the inventive compositions and methods.

In various embodiments, the imatinib or salts thereof used in the high-API compositions and methods of the invention can consist of entirely or almost entirely a single crystal form (e.g., greater than 80%, 85%, 90%, 95%, 99% or 100% of a single crystal form), thereby allowing for controlled and predictable dosing and patient response. In certain embodiments, greater than 95% of imatinib or a salt thereof in the inhalable formulation may be present in a single crystal form. Various crystal forms are discussed in detail below and x-ray powder diffraction diagrams are provided.

In certain embodiments inhalable imatinib compounds may be micronized through wet or dry milling (e.g., jet milling) to achieve the desired particle size for dry powder formulations for inhalation. Imatinib or appropriate salts thereof may be micronized to particle sizes of about 0.5 µm to about 5 µm mass median aerodynamic diameter (MMAD) for desired deep lung penetration. Inhaled products can be limited in terms of mass of powder that can be administered and certain imatinib salts will contribute significantly to the molecular weight of the inhaled compound. Accordingly, in certain embodiments, the imatinib free base may be preferred for efficient delivery of the active moiety to lung tissue. If required, various excipients or carriers can be added to imatinib or salts thereof before or after micronization depending on application while maintaining a relatively high (e.g., 50% or greater) ratio of the API. For example, carriers, excipients, conditioners, and force control agents such as lactose (which when used as a carrier may be conditioned with various solvents to increase separation of imatinib during inhalation), magnesium stearate, leucine, isoleucine, dileucine, trileucine, lecithin, distearylphosphatidylcholine (DSPC) or other lipid-based carriers, or various hydrophilic polymers where they exhibit appropriate physico-chemical properties may be included. The skilled artisan will appreciate that excipients or carriers are optional and that many embodiments of the invention do not require excipients or carriers. In compounds including carriers or excipients, API:carrier ratios may be greater than 50:50, 75:25, or 90:10. Additional ratios are contemplated as discussed below.

Another advantage of the compounds and methods of the invention is the ability to exclude all or most amorphous imatinib from the formulation, even after micronization. As noted above, because crystal form can be important to drug pharmacokinetics and dosing, as well as physicochemical stability and avoiding amorphous content can therefore be important to providing predictable and efficient therapy.

Because the inhalable formulations described herein can modulate the uptake of imatinib in the target tissue of the lungs or microvasculature, formulations of the invention can be used to treat various conditions of the pulmonary cardiovascular system while avoiding the adverse events associated with higher doses that are administered by other routes of administration that introduce the drug systemically prior to reaching the target tissue. For example, compounds and methods of the invention can be used to treat PAH as well as lung transplant rejection, pulmonary veno-occlusive disease (PVOD) and pulmonary hypertension secondary to other diseases like heart failure with preserved ejection fraction (HFpEF) or schistosomiasis. Dose ranges can include between about 10 mg to about 100 mg per dose for inhalation on a twice to four times per day schedule. About 0.1 mg to about 80 mg of the active imatinib compound may then be deposited within the lungs after inhalation. Because compositions of the invention can have relatively high concentrations of API (e.g., 50% or greater), the above doses can be achieved with less overall volume of inhalable compared to conventional formulations having 1%-3% API.

In certain embodiments, formulations of the invention can include processing and administration of imatinib in free base form. Free base imatinib formulations of the invention can retain crystallinity after micronization and are less hygroscopic than certain imatinib salts. Accordingly, compounds and methods of the invention include inhalable formulations of free base imatinib.

Methods and formulations of the invention may include spray-dried imatinib or salts thereof for inhalation. While carriers such as lactose may be used after micronization to aid in delivery via inhalation, those carriers may generally comprise larger diameter particles and complication in the separation of the active imatinib compound may result in lower amounts of the inhaled compound reaching the lungs. Furthermore, the amount of active compound reaching the lungs may be less predictable using such carriers and methods, making dosing more complicated. Accordingly, spray-dried methods may be used wherein imatinib or salts thereof along with various excipients or other additives may be micronized to a desired particle size and suspended or solubilized for spray-drying and inhalation. Using formulations with a higher (e.g., 50% or more) ratio of API can also help achieve more predictable drug concentrations in the target tissue.

In certain embodiments, the micronized imatinib may be suspended in a feedstock for the purposes of spray-drying to avoid the creation of amorphous or polymorphic imatinib content that may occur if dissolved in a solution (e.g. in an appropriate organic solvent or within an acidified aqueous solution) upon spray-drying. By creating a stable suspension of micronized imatinib for spray-drying, once dried, the inhalable formulation can retain the desired crystal structure, particle size, and low levels of amorphous content obtained before the micronization process.

Stable suspensions for spray-drying may be obtained through manipulation of factors affecting imatinib solubility such as pH, ionic strength, and dispersing agents or surfactants. Excipients that may be used before micronization in the spray-drying methods described above include, for example, leucine, dileucine, trileucine, bulking agents such as trehalose or mannitol, lecithin, DSPC or other lipid-based carriers, citrate, or acetate.

Aspects of the invention include an inhalable formulation consisting of at least about 50% imatinib or a salt thereof. The inhalable formulation may include one or more carrier agents. The imatinib or salt thereof may be about 50% of the formulation and the carrier agents may make up the remainder of the formulation. The one or more carrier agents can comprise lactose. In certain embodiments, the inhalable formulation may be a dry powder.

In various embodiments, the imatinib or salt thereof can be present in a therapeutically effective amount to treat a condition of the pulmonary cardiovascular system. The condition of the pulmonary cardiovascular system may be pulmonary arterial hypertension (PAH). Greater than 80% of the imatinib or salt thereof in the inhalable formulation can be present in a single crystal form. The single crystal form can be type A. In certain embodiments, the salt may be at least one selected from the group consisting of glycolate, malate, tartrate, malonate, isethionate, and citrate.

In certain aspects, methods of the invention may include treating a condition of the pulmonary cardiovascular system by providing to a subject an inhalable formulation consisting of at least about 50% imatinib or a salt thereof. In various embodiments, the subject may be a human.

DETAILED DESCRIPTION

Figure 1:
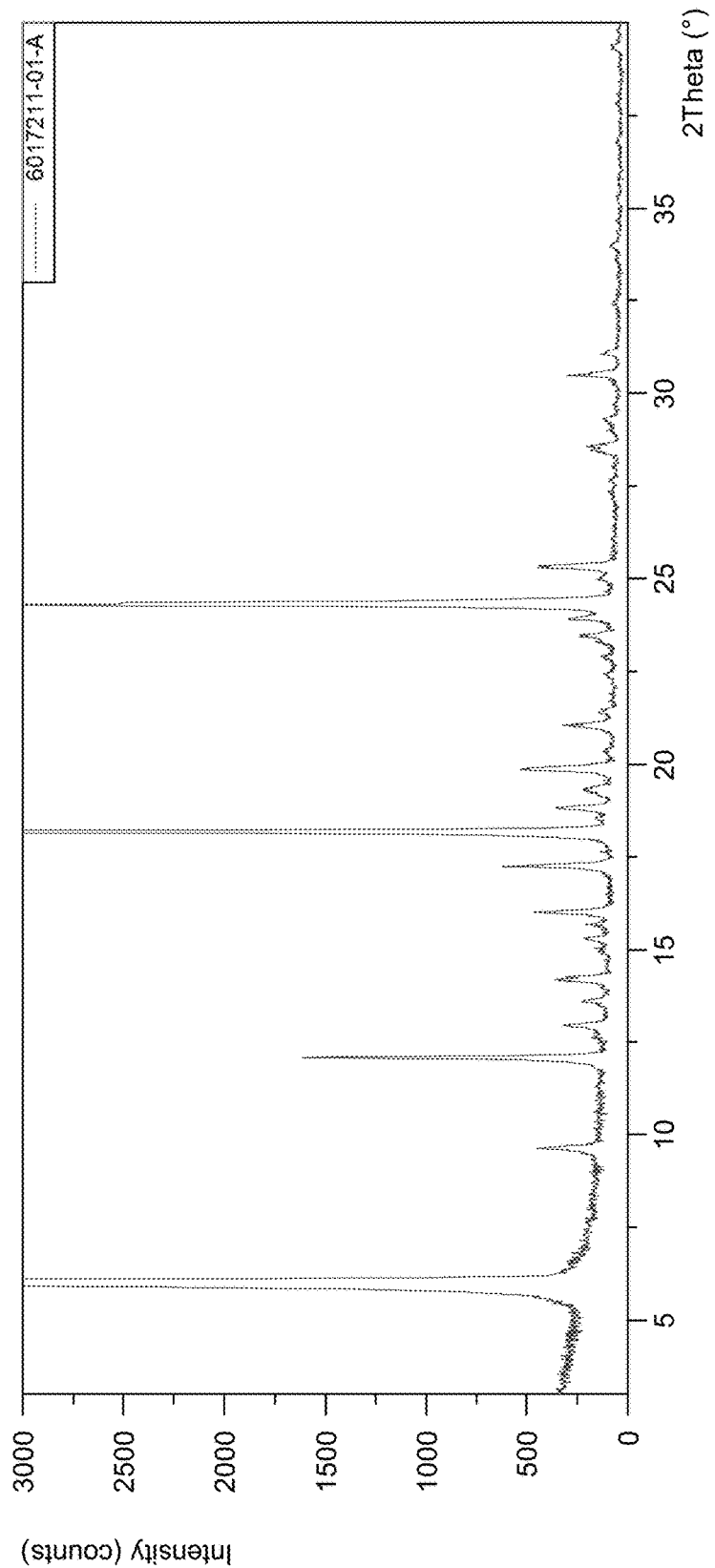
FIG. 1 shows an x-ray powder diffraction diagram of the type A crystal form of imatinib.

The invention relates to inhalable formulations of imatinib and salts thereof. Specifically, inhalable formulations having high ratios of imatinib or salts thereof (e.g., 50% or more) relative to other components are described herein. Imatinib, as used throughout the application, refers to the free base compound unless a salt thereof is recited. Imatinib as the free base has the below structure.

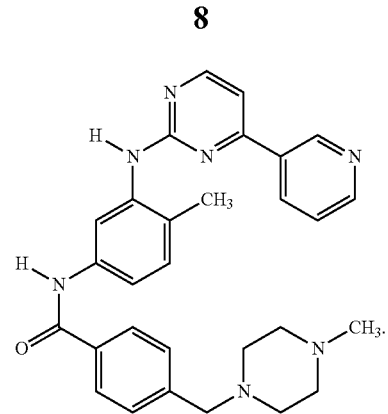

The methods and compositions described herein provide greater concentrations of imatinib in target lung tissue than obtained with equivalent doses administered orally or through IV. Furthermore, those doses, comprising a high percentage of the overall formulation, are deliverable in lower volume formulations than conventional formulations of between 1% and 3% API. Reducing the volume a patient must inhale can increase patient comfort and compliance, thereby improving results. Additionally, a higher percentage of API content can improve the API distribution and blend uniformity. Accordingly, methods and compositions of the invention allow for treatment of conditions of the pulmonary cardiovascular system (e.g., PAH) with lower doses and less inhalable volume than would be required in systemic administration, thereby lowering the risk of adverse events including subdural hematoma (See, Frost et al.). Thus, the invention provides viable treatment methods for life threatening diseases that were heretofore too risky for practical application.

In certain embodiments, compounds of the invention include formulations of imatinib or salts thereof. In preferred embodiments, the free base imatinib is used in a formulation (either in dry powder or suspension) for inhalation to treat a condition of the pulmonary cardiovascular system such as PAH. Certain salt forms are also contemplated. In various embodiments, imatinib salts that were found to exhibit suitable thermal stability and few or single polymorphic forms include glycollate, isethionate, malonate, tartrate, and malate. Other salt forms contemplated herein are xinafoate, furoate, trifenatate, HCl, sulfate, phosphate, lactate, maleate, fumarate, succinate, adipate, mesylate, and citrate.

When the compounds of the present invention are administered as pharmaceuticals, to humans and mammals, they can be given alone or as a pharmaceutical composition containing, for example, 0.1 to 99.5% of active ingredient (e.g., imatinib or a salt thereof) in combination with a pharmaceutically acceptable carrier. In preferred embodiments, to reduce inhaled volumes for patients and improve patient outcomes, formulations can comprise at least 50% imatinib or a salt thereof.

In certain embodiments, imatinib formulations of the invention may include one or more excipients. Excipients may include, for example, lactose in various forms (e.g., roller dried or spray dried). Larger lactose particles can be used as a carrier for inhalation of micronized imatinib formulations. The carrier particles, with their larger size, can be used to increase aerodynamic forces on the combined imatinib/carrier in order to aid in delivery through inhalation. Solvents may be used to condition the lactose surface such that the active component can be effectively separated from the lactose as it leaves the inhaler device and within the oral cavity when being used as a carrier. Magnesium stearate can be used as a force-control agent or conditioning agent in various embodiments. In some embodiments, leucine can be used as a force-control agent including different forms of leucine (e.g. isoleucine) along with dileucine and even trileucine.

Lecithin phospholipids such as DSPC may be used as an excipient for dry powder inhalation. In certain embodiments, excipients may include various hydrophilic polymers. See, for example, Karolewicz, B., 2016, A review of polymers as multifunctional excipients in drug dosage form technology, Saudi Pharm J., 24(5): 525-536, incorporated herein by reference.

In the high-API-ratio formulations contemplated herein, carriers or excipients may make up the remainder of the formulation in amounts of 50% or less of the overall composition. In certain embodiments, inhalable formulations may have API:carrier ratios of 50:50, 55:45, 60:40, 65:35, 70:30, 75:25, 80:20, 85:15, 90:10, or 95:5. Certain inhalable formulations may be pure API with no additional components. In various embodiments, formulations may include imatinib or salts thereof as the API in amounts greater than 5%, 10%, 15%, 20%, 25%, 30%, 35%, 40%, or 45%. As used herein, API ratios refer to % w/w.

In various embodiments, micronized imatinib and salts thereof retain crystallinity, even after micronization and spray drying (as discussed in detail below). For example, imatinib formulations of the invention can include less than 50%, less than 25%, less than 20%, less than 10%, less than 9%, less than 8%, less than 7%, less than 6%, less than 5%, less than 4%, less than 3%, less than 2%, or less than 1% amorphous imatinib by mass. In preferred embodiments, formulations of the invention include no observable amorphous imatinib content. Of particular note is, by suspending micronized imatinib particles in a solution as opposed to solubilizing, the desired crystalline form and low amorphous content obtained during micronization is carried through to the spray-dried inhalable powder because the imatinib crystals are not dissolved in the solution to a significant degree.

Another unexpected result obtained with methods and formulations of the invention is that imatinib formulations of the invention are significantly less hygroscopic than conventional imatinib mesylate compounds. Accordingly, the imatinib formulations of the invention are better suited for dry powder inhalation and can comprise less than 5% water content, less than 4%, less than 3%, less than 2%, or, in preferred embodiments, less than 1% water content.

As discussed above, in order to accurately and consistently model pharmacokinetics of the imatinib formulations for proper dosing, low polymorphism is desired. To that end, inhalable formulations of the invention include imatinib or a salt thereof present in a single crystal form. In various embodiments, imatinib or a salt thereof may be present at greater than 75%, 80%, 85%, 90%, 95%, or, in preferred embodiments, greater than 99% in a single crystal form by mass. The single crystal form may be, for example, type A or type B in various embodiments.

Figure 2:
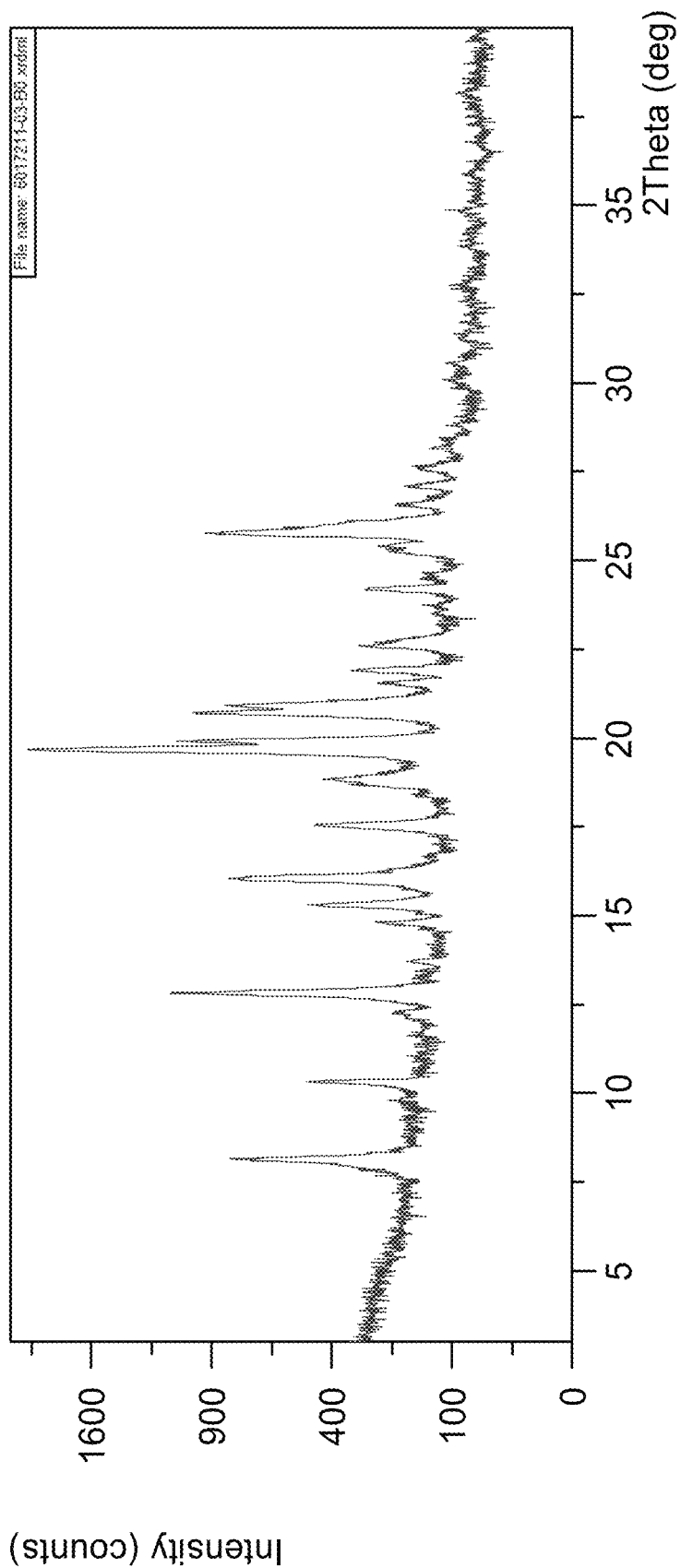
FIG. 2 shows an x-ray powder diffraction diagram of the type B crystal form of imatinib.

Crystalline purity can be estimated using any known method including, for example, x-ray powder diffraction (XRPD). An XRPD diagram for the type A crystal form of free base imatinib is shown in FIG. 1. An XRPD diagram for the type B crystal form of free base imatinib is shown in FIG. 2.

In various embodiments, imatinib or salts thereof are provided in dry powder formulations for inhalation. Dry powder can be administered via, for example, dry powder inhalers such as described in Berkenfeld, et al., 2015, Devices for Dry Powder Drug Delivery to the Lung, AAPS PharmaSciTech, 16(3): 479-490, incorporated herein by reference. Dry powder compounds may be divided into single doses for single, twice daily, three times daily, or four times daily inhalation to treat disorders such as PAH or other conditions of the pulmonary cardiovascular system. The single doses may be divided into individual capsules or other formats compatible with the dry powder inhaler to be used.

In other embodiments, imatinib suspensions having the characteristics described herein (e.g., low polymorphism and amorphous content) can be delivered via inhalation using, for example, a nebulizer. Imatinib suspensions may offer advantages over solutions as discussed below. For nebulized suspensions, micronization and particle diameter may be of particular importance for efficient delivery and imatinib may be preferably micronized to a mass median diameter of 2 μm or less. The suspension solution for nebulizer inhalation can be aqueous and doses may be divided into individual containers or compartments for sterile storage prior to use.

Micronized imatinib particle size can range from about 0.5 μm to about 5 μm depending on application (e.g., dry powder or suspension for inhalation). In preferred embodiments the size range is about 1 μm to about 3 μm in dry powder formulations to achieve deep lung penetration.

In various embodiments, the imatinib formulations of the invention may be pharmaceutical compositions for use in treating various conditions of the pulmonary cardiovascular system, such as PAH. For example, imatinib is a potent inhibitor of the platelet-derived growth factor receptor (PDGFR) and other signaling kinases. Accordingly, the compositions of the invention may be used to treat any disease or disorder that involves inhibition of PDGFR or other kinases sensitive to imatinib.

In certain embodiments, the compositions of the invention may be used to treat PAH. For treatment of PAH or other disorders, a therapeutically effective amount of a pharmaceutical composition of imatinib according to the various embodiments described herein can be delivered, via inhalation (e.g., via dry powder inhaler or nebulizer) to deliver the desired amount of imatinib compound to the target lung tissue.

Dosages for treating PAH and other conditions of the pulmonary cardiovascular system may be in the range of between about 10 mg to about 100 mg per dose for inhalation on once, twice or three times per day schedule. About 0.1 mg to about 80 mg of the imatinib of salt thereof may then be deposited within the lung after inhalation. In certain embodiments about 10 mg to 30 mg of imatinib may be given in a capsule for a single dry-powder inhalation dose with about 5 mg to about 10 mg of the compound to be expected to reach the lungs. In inhalable suspension embodiments, imatinib may be present at about 0.1 to about 1 mg/kg in a dose and may be administered one to four times a day to obtain the desired therapeutic results.

In certain embodiments, imatinib formulations of the invention may be used to treat pulmonary hypertension as a result of schistosomiasis. See, for example, Li, et al., 2019, The ABL kinase inhibitor imatinib causes phenotypic changes and lethality in adult Schistosoma japonicum, Parasitol Res., 118(3): 881-890; Graham, et al., 2010, Schistosomiasis-associated pulmonary hypertension: pulmonary vascular disease: the global perspective, Chest, 137(6 Suppl): 20S-29S, the content of each of which is incorporated herein by reference.

Imatinib pharmaceutical compositions of the invention may be used to treat lung transplant recipients to prevent organ rejection. See, Keil, et al., 2019, Synergism of imatinib, vatalanib and everolimus in the prevention of chronic lung allograft rejection after lung transplantation (LTx) in rats, Histol Histopathol, 1: 18088, incorporated herein by reference.

In certain embodiments, pharmaceutical compositions described herein can be used to treat pulmonary veno-occlusive disease (PVOD). See Sato, et al., 2019, Beneficial Effects of Imatinib in a Patient with Suspected Pulmonary Veno-Occlusive Disease, Tohoku J Exp Med. 2019 Feb; 247(2): 69-73, incorporated herein by reference.

For treatment of any conditions of the pulmonary cardiovascular system for which imatinib may produce a therapeutic effect, compounds and methods of the invention may be used to provide greater concentration at the target lung tissue through inhalation along with consistent, predictable pharmacokinetics afforded by low polymorphism and amorphous content. The efficient localization of therapeutic compound at the target tissue allows for lower systemic exposure and avoidance of the adverse events associated with prolonged oral administration of imatinib mesylate.

Methods of the invention can include preparation of imatinib formulations. As noted above, imatinib or salts thereof may be administered via inhalation in suspension or dry powder form. Dry powder formulations may be obtained via any known method including, in preferred embodiments, jet milling. Jet milling can be used to grind imatinib and, potentially, various additives (e.g., excipients) using a jet (or jets) of compressed air or gas to force collisions between the particles as they transit at near sonic velocity around the perimeter of a toroidal chamber. The size reduction is the result of the high-velocity collisions between particles of the process material. Outputs of the jet mill may allow particles to exit the apparatus once a desired size has been reached. As noted herein, desired particle size for dry powder inhalation and other formulations may be in the range of about 0.5 µm to about 5 µm.

In certain embodiments, bulk imatinib may be micronized to the desired size for inhalation via wet milling wherein the imatinib particles are suspended in a slurry and reduced through shearing or impact with a grinding media.

An unexpected finding of the invention is that, once micronized, free base imatinib retains crystallinity and is considerably less hygroscopic than certain salt forms of imatinib (e.g., imatinib mesylate). Furthermore, micronized imatinib obtained using methods of the invention has been found to exhibit no apparent polymorphs other than the designated Type A and very low levels of amorphous content. Accordingly, this can result in improved stability of the drug substance and any drug product upon storage. Single crystal forms such as described may allow for more predictable in vivo behavior and appropriate dosing can be determined.

Once micronized, in dry powder form, imatinib formulations of the invention, with their low polymorphic and amorphous content, can be prepared for inhalation. In certain embodiments, the dry powder imatinib can be combined with larger carrier particles such as lactose as discussed above.

In some embodiments an imatinib suspension can be formed. The suspension may result from dry micronization followed by suspension of the resulting dry powder or can be obtained as the outcome of a wet milling procedure. Imatinib suspensions of micronized crystal forms may be used in nebulized inhalation treatment or may be spray dried for dry powder treatments.

Figure 3:
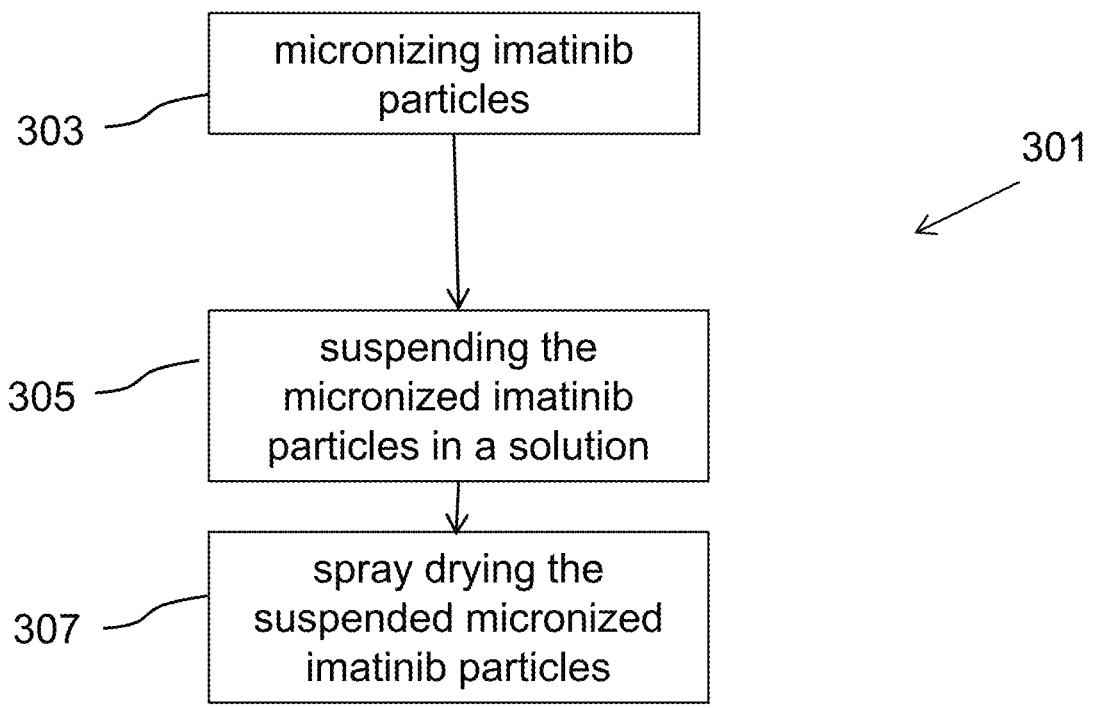
FIG. 3 diagrams steps of an exemplary method of preparing an inhalable formulation of imatinib.

FIG. 3 diagrams a spray drying method for preparing a dry powder imatinib formulation for inhalation. First, bulk imatinib is micronized 303 as described above to obtain imatinib particles in a desired size range. Then the micronized imatinib is suspended in a solution 305 such that they do not dissolve and instead retain the desired crystalline features (e.g., low polymorphism and amorphous content). The suspended particles can then be spray dried 307 using any known method. Spray drying techniques are well characterized and described, for example, in Ziaee, et al., 2019, Spray drying of pharmaceuticals and biopharmaceuticals: Critical parameters and experimental process optimization approaches, Eur. J. Pharm. Sci., 127: 300-318, and Weers et al., 2019, AAPS PharmSciTech. 2019 Feb 7; 20(3): 103. doi: 10.1208/s12249-018-1280-0, and 2018/0303753, each of which is incorporated herein by reference. Spray drying micronized imatinib or salts thereof provides for uniform and predictable crystallinity and particle size and can avoid the need for large carrier molecules that may adversely affect the amount of inhaled drug that reaches the target lung tissue.

In spray-dried embodiments, micronized drug particles may be suspended within a non-aqueous solvent or within an emulsion of a non-aqueous solvent which, in turn is emulsified or dispersed within an aqueous environment (e.g. oil in water) and spray-dried, resulting in crystalline drug particles. The non-aqueous component may or may not be fugitive and thus could be removed completely during spray drying or, it could be retained, depending on the desired properties required. In such embodiments, each atomized droplet (mass median diameter ~10 µm) contains dispersed drug crystals. During the initial moments of the drying process, the more volatile aqueous phase begins to evaporate. The rapidly receding atomized droplet interface drives enrichment of the slowly diffusing drug and emulsion particles at the interface. This leads to formation of a void space in the center of the drying droplet. As the drying process continues, the less volatile oil phase in the emulsion droplets evaporates, resulting in formation of hollow pores in their place. Overall, the resulting hollow spray-dried composite particles contain drug crystals.

As maintaining a stable solution of crystalline imatinib is important to many features of the formulations and methods of the invention, formulation methods include manipulation of the suspension to prevent dissolution of the imatinib. Aqueous solution factors such as pH, ionic strength and dispersing agents may be used to obtain a stable suspension for nebulized inhalation or spray drying. For example, the pH of the aqueous solution may be adjusted to prevent dissolution.

Additionally, the presence of ions in aqueous solution may tend to 'salt out' the imatinib. The solubility of the both imatinib and its mesylate salt may decrease with salinity. Accordingly, salt in the aqueous solution may be used to reduce solubility of the imatinib crystals in certain embodiments.

To promote dispersion and thoroughly deagglomerate the imatinib particles, a dispersing agent or surfactant (e.g., Tween 20 or Tween 80) may be added but should not cause dissolution of the imatinib in suspension.

In certain embodiments, excipients can be added to the suspension before spray drying. In various embodiments, the excipient may be a water-soluble excipient, such as leucine, dileucine, trileucine, trehalose, mannitol, citrate or acetate. In other embodiment, the excipient may be a water insoluble excipient, such as lecithin, distearylphosphatidylcholine (DSPC) or limonene. Such insoluble excipients may be dissolved in a non-aqueous medium that is miscible or immiscible with water, thereby creating an emulsion. Alternatively, a liposomal dispersion could be created into which the suspended imatinib could be added and homogenized or where it could be spray dried in separate feedstocks.

The effective dosage of each agent can readily be determined by the skilled person, having regard to typical factors such as the age, weight, sex and clinical history of the patient. In general, a suitable daily dose of a compound of the invention will be that amount of the compound which is the lowest dose effective to produce the desired therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms.

The pharmaceutical compositions of the invention include a "therapeutically effective amount" or a "prophylactically effective amount" of one or more of the compounds of the present invention, or functional derivatives thereof. An "effective amount" refers to an amount effective, at dosages and for periods of time necessary, to achieve the desired therapeutic result, e.g., a diminishment or prevention of effects associated with PAH. A therapeutically effective amount of a compound of the present invention or functional derivatives thereof may vary according to factors such as the disease state, age, sex, and weight of the subject, and the ability of the therapeutic compound to elicit a desired response in the subject. A therapeutically effective amount is also one in which any toxic or detrimental effects of the therapeutic agent are outweighed by the therapeutically beneficial effects.

A "prophylactically effective amount" refers to an amount effective, at dosages and for periods of time necessary, to achieve the desired prophylactic result. Typically, since a prophylactic dose is used in subjects prior to, or at an earlier stage of disease, the prophylactically effective amount may be less than the therapeutically effective amount. A prophylactically or therapeutically effective amount is also one in which any toxic or detrimental effects of the compound are outweighed by the beneficial effects.

Dosage regimens may be adjusted to provide the optimum desired response (e.g. a therapeutic or prophylactic response). For example, a single inhalable bolus may be administered, several divided doses may be administered over time or the dose may be proportionally reduced or increased as indicated by the exigency of the therapeutic situation. Actual dosage levels of the active ingredients in the pharmaceutical compositions of this invention may be varied so as to obtain an amount of the active ingredient which is effective to achieve the desired therapeutic response for a particular subject, composition, and mode of administration, without being toxic to the patient.

The term "dosage unit" as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the compound, and (b) the limitations inherent in the art of compounding such an active compound for the treatment of sensitivity in individuals.

In some embodiments, therapeutically effective amount can be estimated initially either in cell culture assays or in animal models, usually rats, non-human primates, mice, rabbits, dogs, or pigs. The animal model is also used to achieve a desirable concentration range and route of administration. Such information can then be used to determine useful doses and routes for administration in other subjects. Generally, the therapeutically effective amount is sufficient to reduce PAH symptoms in a subject. In some embodiments, the therapeutically effective amount is sufficient to eliminate PAH symptoms in a subject.

Dosages for a particular patient can be determined by one of ordinary skill in the art using conventional considerations, (e.g. by means of an appropriate, conventional pharmacological protocol). A physician may, for example, prescribe a relatively low dose at first, subsequently increasing the dose until an appropriate response is obtained. The dose administered to a patient is sufficient to effect a beneficial therapeutic response in the patient over time, or, e.g., to reduce symptoms, or other appropriate activity, depending on the application. The dose is determined by the efficacy of the particular formulation, and the activity, stability, or half-life of the compounds of the invention or functional derivatives thereof, and the condition of the patient, as well as the body weight or surface area of the patient to be treated. The size of the dose is also determined by the existence, nature, and extent of any adverse side-effects that accompany the administration of a particular vector, formulation, or the like in a particular subject. Therapeutic compositions comprising one or more compounds of the invention or functional derivatives thereof are optionally tested in one or more appropriate in vitro and/or in vivo animal models of disease, such as models of PAH, to confirm efficacy, tissue metabolism, and to estimate dosages, according to methods well known in the art. In particular, dosages can be initially determined by activity, stability or other suitable measures of treatment vs. non-treatment (e.g., comparison of treated vs. untreated cells or animal models), in a relevant assay. Administration can be accomplished via single or divided doses.

In certain embodiments, in which an aqueous suspension is part of the manufacturing process, the aqueous suspension may contain the active material in admixture with excipients suitable for the manufacture of aqueous suspensions. Such excipients are suspending agents dispersing or wetting agents such as a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, mannitol, or trehalose.

Dispersible powders and granules suitable for preparation of an aqueous suspension by the addition of water provide the active ingredient in admixture with a dispersing or wetting agent, suspending agent and one or more preservatives.

The term "pharmaceutical composition" means a composition comprising a compound as described herein and at least one component comprising pharmaceutically acceptable carriers, diluents, adjuvants, excipients, or vehicles, such as preserving agents, taste-masking agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

The term "pharmaceutically acceptable carrier" is used to mean any carrier, diluent, adjuvant, excipient, or vehicle, as described herein. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Examples of suitable carriers, diluents, solvents, or vehicles include water, ethanol, polyols, suitable mixtures thereof, vegetable oils (such as olive oil), and organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

The term "pharmaceutically acceptable" means it is, within the scope of sound medical judgment, suitable for use in contact with the cells of humans and lower animals without undue toxicity, irritation, allergic response, and the like, and are commensurate with a reasonable benefit/risk ratio.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

Equivalents

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Example 1

Intratracheal instillation of imatinib in an animal model was found to provide significantly (e.g., 25 times higher as measured via AUC) lung exposure to the compound compared to oral or IV administration. Accordingly, lower doses of imatinib can be provided through inhalation while still providing the same or greater concentration in the target lungs thereby achieving the desired therapeutic effects with diminished risk of adverse events. TABLE 1 shows lung level comparisons in an animal model of various doses of imatinib and imatinib mesylate suspensions and solutions administered orally or via intratracheal instillation (IT) or intravenous (IV).

TABLE 1

Figure 4:
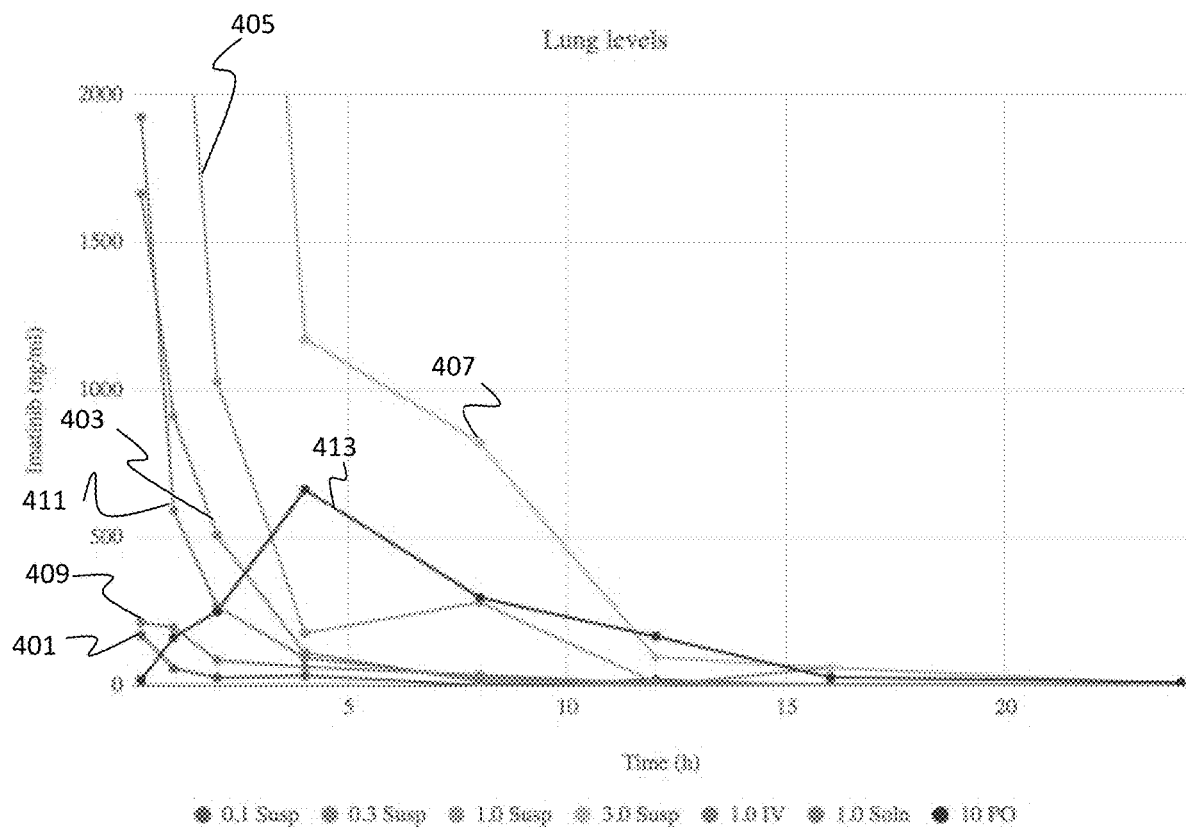
FIG. 4 shows imatinib lung levels over time for various doses of imatinib solutions and suspensions delivered via various administration routes.

| Route | Form | Dose (mg/kg) | AUC (h*ng/g) | Dose multiple vs. Oral | FIG. 4 Indicator |
|---|---|---|---|---|---|
| IT | suspension | 3 | 379659 | 27.4 | 407 |
| IT | suspension | 1 | 96981 | 21.0 | 405 |
| IT | suspension | 0.3 | 40986 | 29.6 | 403 |
| IT | suspension | 0.1 | 4707 | 10.2 | 401 |
| IT | solution-mesylate | 1 | 41852 | 9.1 | 411 |
| IV | solution-mesylate | 1 | 7794 | 1.7 | 409 |
| Oral | solution-mesylate | 10 | 46223 | 1 | 413 |

FIG. 4 shows lung concentrations of imatinib over time of the various forms and routes described in TABLE 1. The suspensions administered via IT were found to maintain levels above IC50 long enough to allow for TID or even BID dosing for inhaled solutions. The plotted routes, forms, and doses are indicated in TABLE 1 above.

Figure 5:
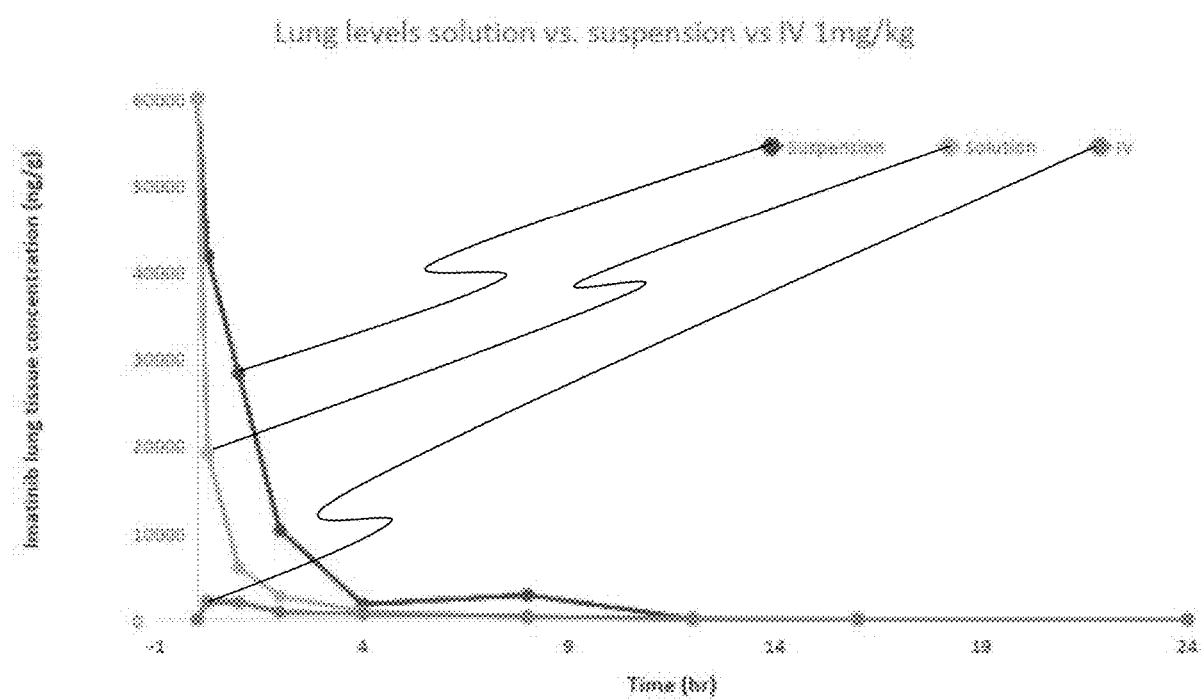
FIG. 5 shows an imatinib lung concentration comparison between 1 mg/kg of imatinib suspension or solution delivered by intratracheal instillation and 1 mg/kg of imatinib delivered by IV.

FIG. 5 shows lung concentrations of imatinib solution and suspensions administered via IT compared to lung concentrations of an IV solution of imatinib at 1 mg/kb dose and illustrates a clear AUC advantage in the IT suspension over the IT solution and both over the IV solution.

Example 2

Initial physicochemical characterization of unmicronized and micronized Imatinib Free Base was performed using an array of techniques. Imatinib free base was obtained as a dry powder.

Particle size reduction of Imatinib Free Base was performed using a 2-inch air jet mill (Food Pharma Systems, PM-2, Italy). The system was operated under nitrogen at a venturi and ring pressure of 8 bar and 7 bar, respectively. A total of 8.00 g of raw Imatinib Free Base material was micronized. The rate at which the material was introduced into the mill was approximately 0.5 g/min. All samples were collected and stored in an amber glass jar, which was then sealed in aluminium laminate pouch.

Figure 6:
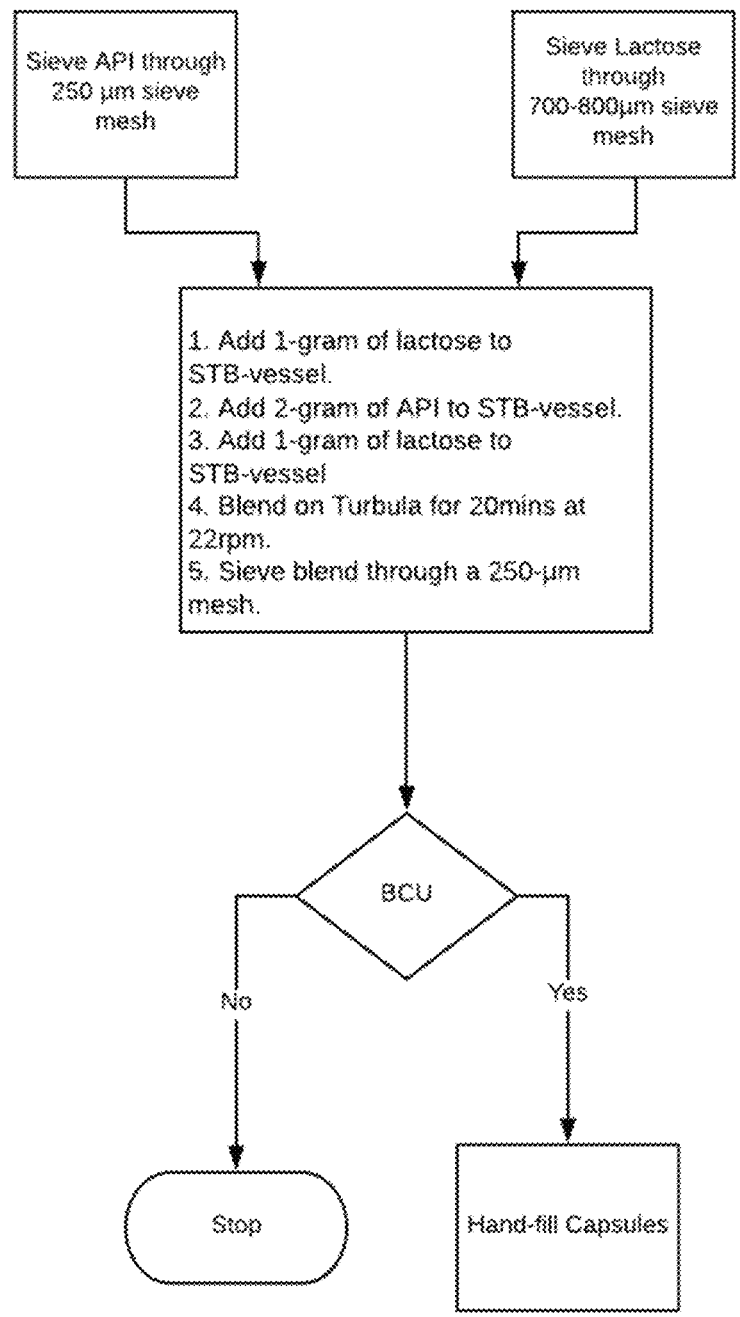
FIG. 6 diagrams exemplary processing steps for inhalable imatinib preparations.

Micronized material was used to manufacture a 50% drug load with inhalation grade lactose (Respitose ML001, available from DFE pharma, Germany). This formulation was manufactured at 4-gram total batch size using low shear blending. An STB-50 vessel was used for the manufacture. The processing steps are shown in the flow diagram in FIG. 6. This formulation equated to a 10 mg nominal dose per 20 mg of powder.

After conducting blend content uniformity (BCU) measurements, formulations (20.0±0.2 mg) was filled into size 3 Hydroxypropyl methylcellulose (HPMC) capsules by hand. Filled capsules were tested for emitted dose by a Dosage Unit Sampling Apparatus (DUSA) and total lung dose using an OPC-standard anatomical throat. The inhaler used for this component of the study was a HR-RS01 (Plastiape, Italy) at 60 L/min.

A feasibility batch was manufactured on small scale (2 g) using a Buchi B290 laboratory spray dryer (see Table 2 below). Micronized Imatinib was suspended in water at an API:Leucine ratio of 75:25 w/w. The aspiration rate was at the highest setting, maximum suitable atomisation pressure and feed rate of 2-4 mL/min. Spray drying conditions was checked by assessment of yield, powder appearance and PSD during the run.

TABLE 2

| | Spray drying formulation in water |
|---|---|
| Imatinib (micronized) | 1500 mg |
| Leucine | 500 mg |
| NaCl | N/A |
| Total solids | 2000 mg |
| Water | 25 mL (8% w/v solids) |
| % dissolved imatinib | 0.01% w/w (150 micrograms) |
| % imatinib in the soluble components | 0.03% w/w |

For particle sizing, unmicronized imatinib was dispersed with compressed air (2 bar) and sized by laser diffraction (RODOS dry powder feeder; HELOS laser diffractometer, WINDOX 4.0 software; Sympatec GmbH, Germany). The 10, 50 and 90% undersize particle size values (X10, X50 and X90, respectively) were obtained. To evaluate the extent of cohesion between particles, values of X50 were measured (n=3) over the pressure range of 1-3 bar for the micronized material.

The specific surface area (SSA) of Imatinib samples (0.6 g) was measured using a Micrometrics TriStar 3000 surface area analyser (Micromeritics Instrument Corporation, Norcross, USA). An eleven-point BET nitrogen adsorption analysis was carried out in triplicate after degassing the samples for 16 hours in a FlowPrep 060 degasser at 25° C. (Micromeritics Instrument Corporation, Norcross, USA).

To determine the X-ray powder diffraction (XRPD) pattern of the FP samples, all samples were analyzed on a Bruker Powder Diffractometer (D8; Bruker AXS Inc., Madison, USA) using CuKα radiation ($\lambda$=1.54 Å). The data were collected over a single 2θ sweep with range 2θ=2–40° 2θ and step time 0.2 s.

The thermal properties of all samples were investigated using a differential scanning calorimeter (DSC 8000, PerkinElmer, UK), calibrated with an indium standard. Approximately 3 mg of sample was accurately weighted into an aluminum pan and crimped with a lid to form a hermetic seal. The sample and reference pan were heated at a rate of 10° C./min from 20° C. to 300° C. The calorimeter head was continuously flushed with dry nitrogen gas at 0.2 L/min during all measurements. Thermalgravimetric analysis was performed with a PerkinElmer Pyris 1 using aluminum vented pans in ceramic crucibles. The samples were heated at a rate of 10° C./min from 20° C. to 400° C.

Figure 7:
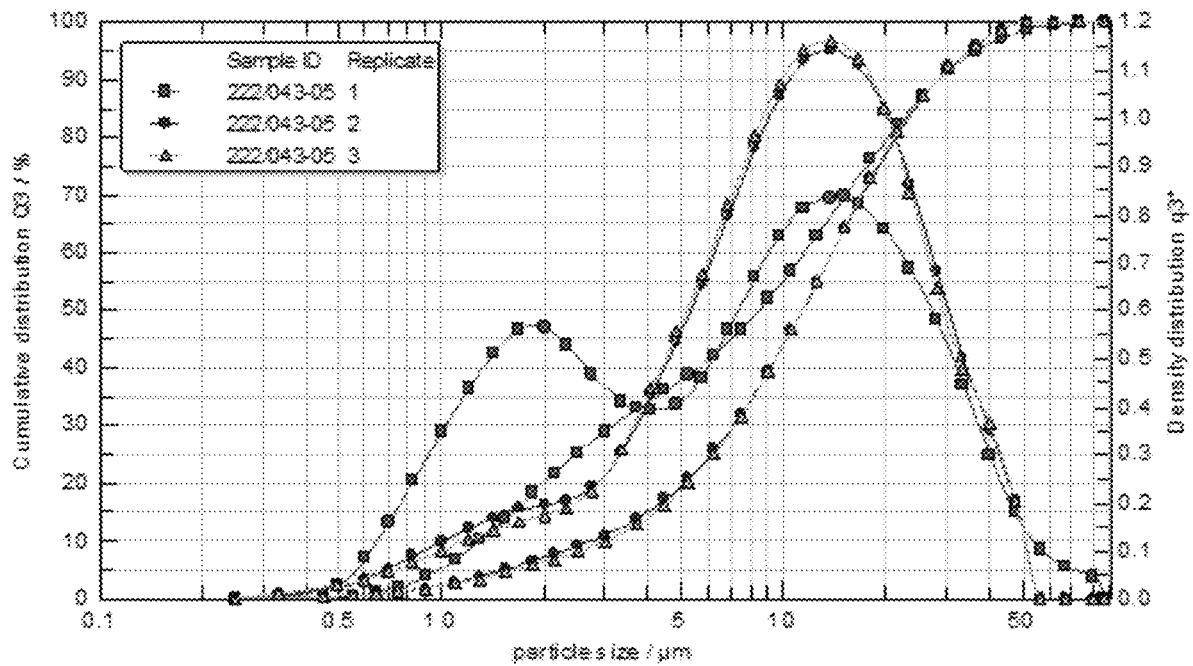
FIG. 7 shows particle size distribution (PSD) analysis of unmicronized imatinib.
Figure 8:
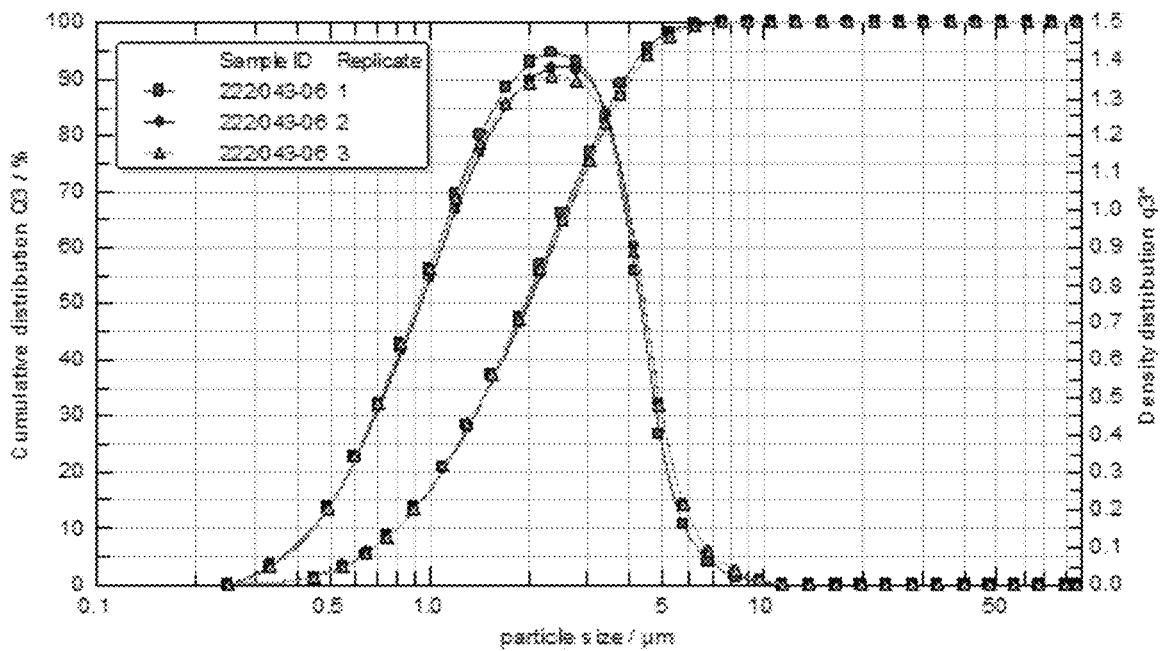
FIG. 8 shows PSD analysis of micronized imatinib at 1 bar.
Figure 9:
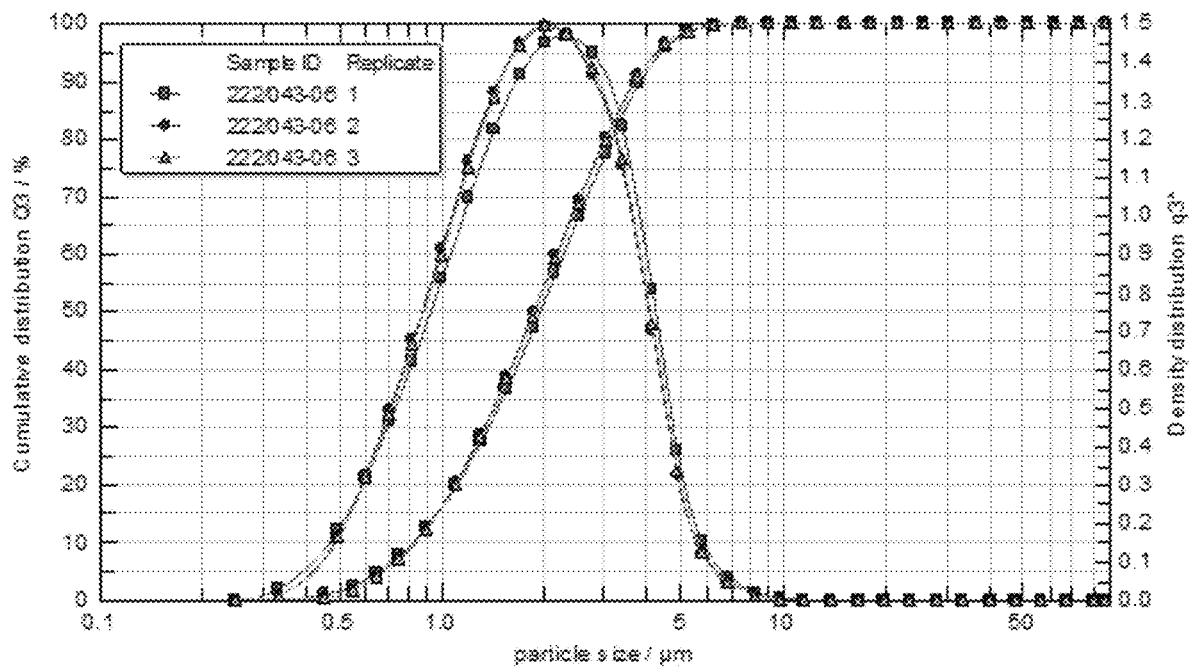
FIG. 9 shows PSD analysis of micronized imatinib at 2 bar.
Figure 10:
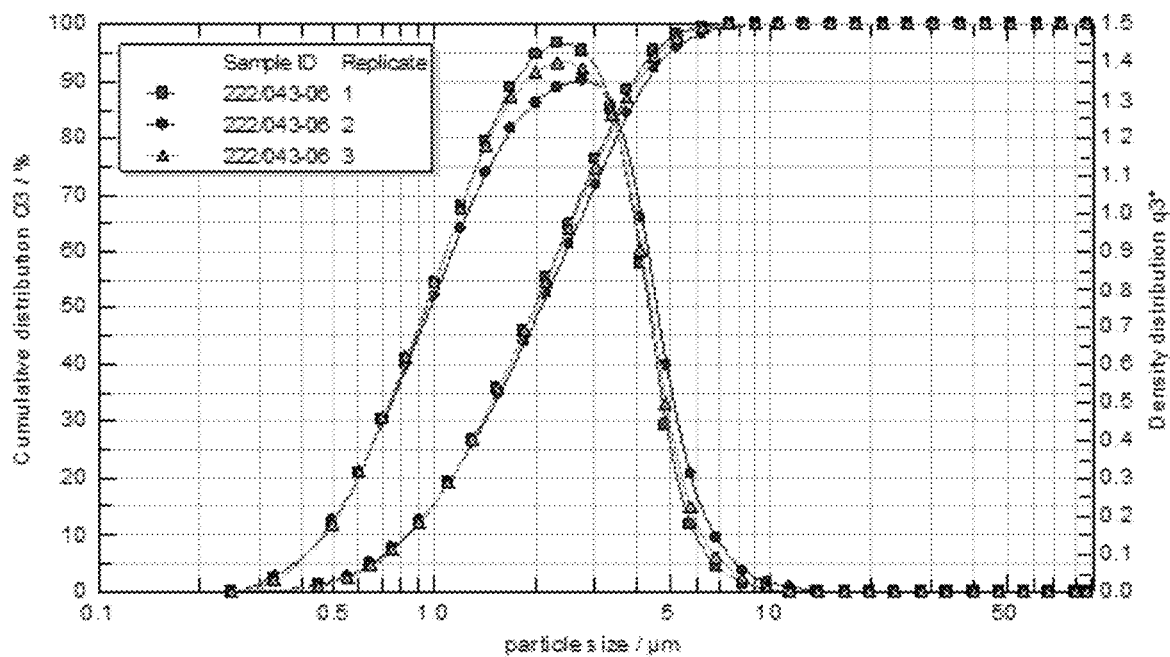
FIG. 10 shows PSD analysis of micronized imatinib at 3 bar.

Particle size distribution (PSD) analysis of the unmicronized material is shown in FIG. 7 and micronized material is shown at 1, 2, and 3 bar in FIGS. 8-10, respectively. These data are also summarized in Table 3. In addition, the specific surface area of unmicronized and micronized Imatinib free-base is shown in TABLE 4.

TABLE 3

Particle size distribution of unmicronized, micronized and co-spray dried Imatinib.

| Dispersing Conditions | $d_{10}$/μm (SDev) | $d_{50}$/μm (SDev) | $d_{90}$/μm (SDev) |
|---|---|---|---|
| Un-Micronized material | | | |
| 2 bar | 2.38 (0.94) | 10.42 (1.65) | 28.68 (0.24) |
| Micronized material | | | |
| 1 bar | 0.80 (0.00) | 1.95 (0.03) | 4.00 (0.10) |
| 2 bar | 0.83 (0.01) | 1.89 (0.05) | 3.74 (0.08) |
| 3 bar | 0.83 (0.00) | 2.01 (0.05) | 4.11 (0.18) |
| Spray Dried | | | |
| | 0.79 (0.01) | 3.02 (0.02) | 8.04 (0.10) |

TABLE 4

Specific surface area (SSA) analysed by BET of unmicronized and micronized Imatinib.

| Material | SSA (m2/g) | Mean SSA (m2/g) | Std. Dev. |
|---|---|---|---|
| Un-Micronized | 0.88 | 0.88 | 0.00 |
| | 0.87 | | |
| Micronized | 7.29 | 7.85 | 0.80 |

Unmicronized Imatinib had a median particle size of 10.4 μm and 10% and 90%-undersize of 2.38 and 28.68 μm, respectively. The span of the PSD of the unmicronized material was 2.53. The surface area of the unmicronized material was 0.88 m2/g.

From the 8 g of unmicronized material that was air-jet micronized, a total of 5.6 g of micronized material was collected. This equated to a product yield of 71.3%. The surface area of the micronized material was 7.9 m2/g, suggesting that the micronization process was successful in creating new surface area and reduction of particle size. For the suspension spray-dried material with leucine, the yield from the process was approximately 80% and presented good flow properties.

The median particle size of the micronized material when dispersed at 1, 2 and 3 bar was 1.95, 1.89 and 2.01 μm, respectively. The 10%-undersize ranged from 0.80-0.83 μm and 90%-undersize ranged from 3.74-4.11 μm. These data suggest the new micronized Imatinib had a slightly finer particle size than the material micronized in report 20181026-106-001 v3.0. That material had d10, d50 and d90 of 1.25, 2.07 and 3.41 μm, respectively.

Figure 11:
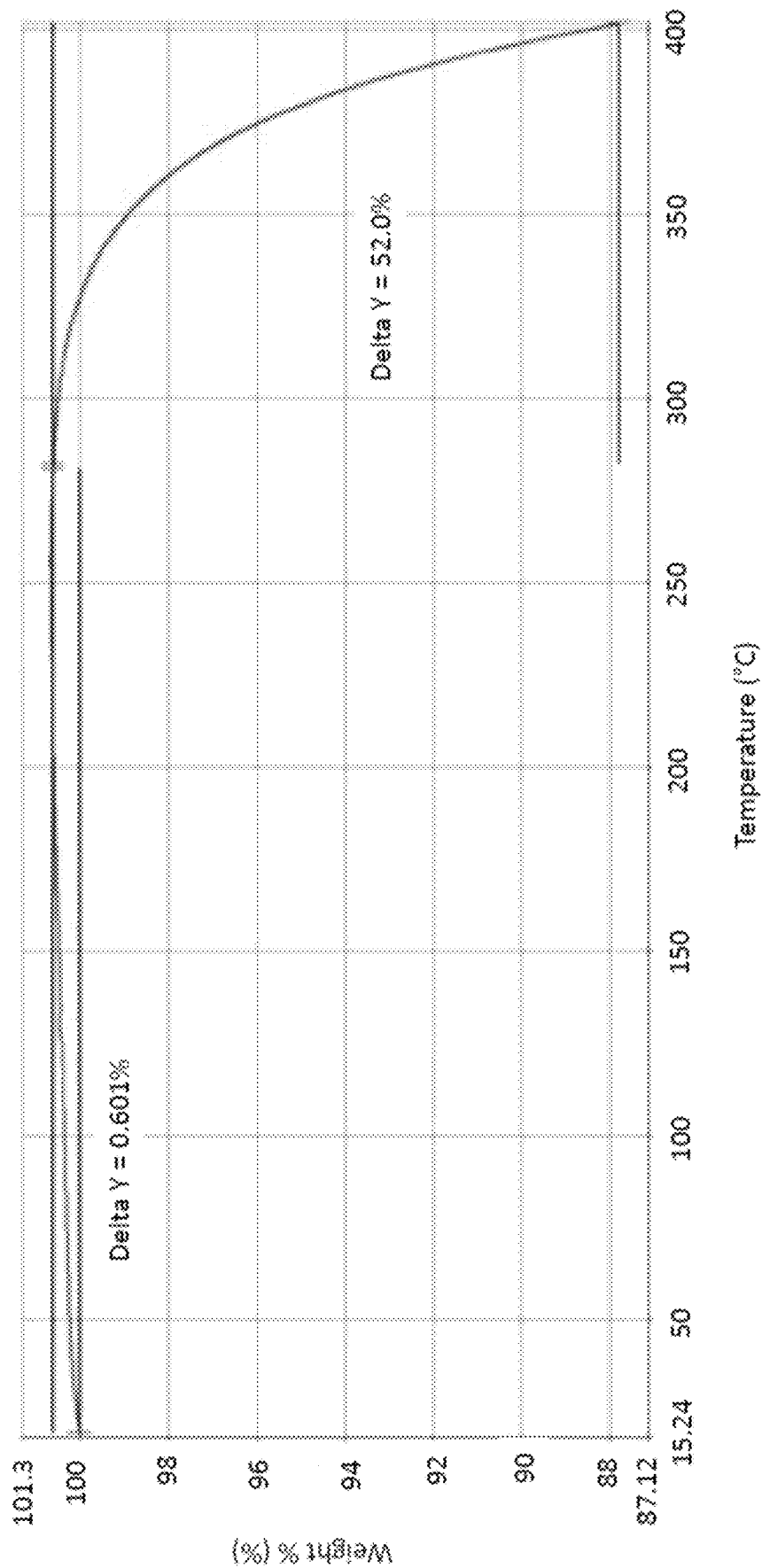
FIG. 11 shows thermalgravimetric analysis (TGA) of imatinib Free Base, pre-micronization.

The particle size in terms of d10, d50 and d90 was 0.79, 3.02 and 8.04 μm, respectively. These data suggested that the spray-drying of suspended micronized Imatinib had a modestly larger particle size. The un-micronized sample was analyzed by thermogravimetric analysis (TGA) to determine the decomposition temperature prior to differential scanning calorimeter (DSC) analysis. It was concluded that the sample starts to decompose at approx. 300° C. and therefore the DSC analysis was set for 20-300° C. (FIG. 11).

Figure 12:
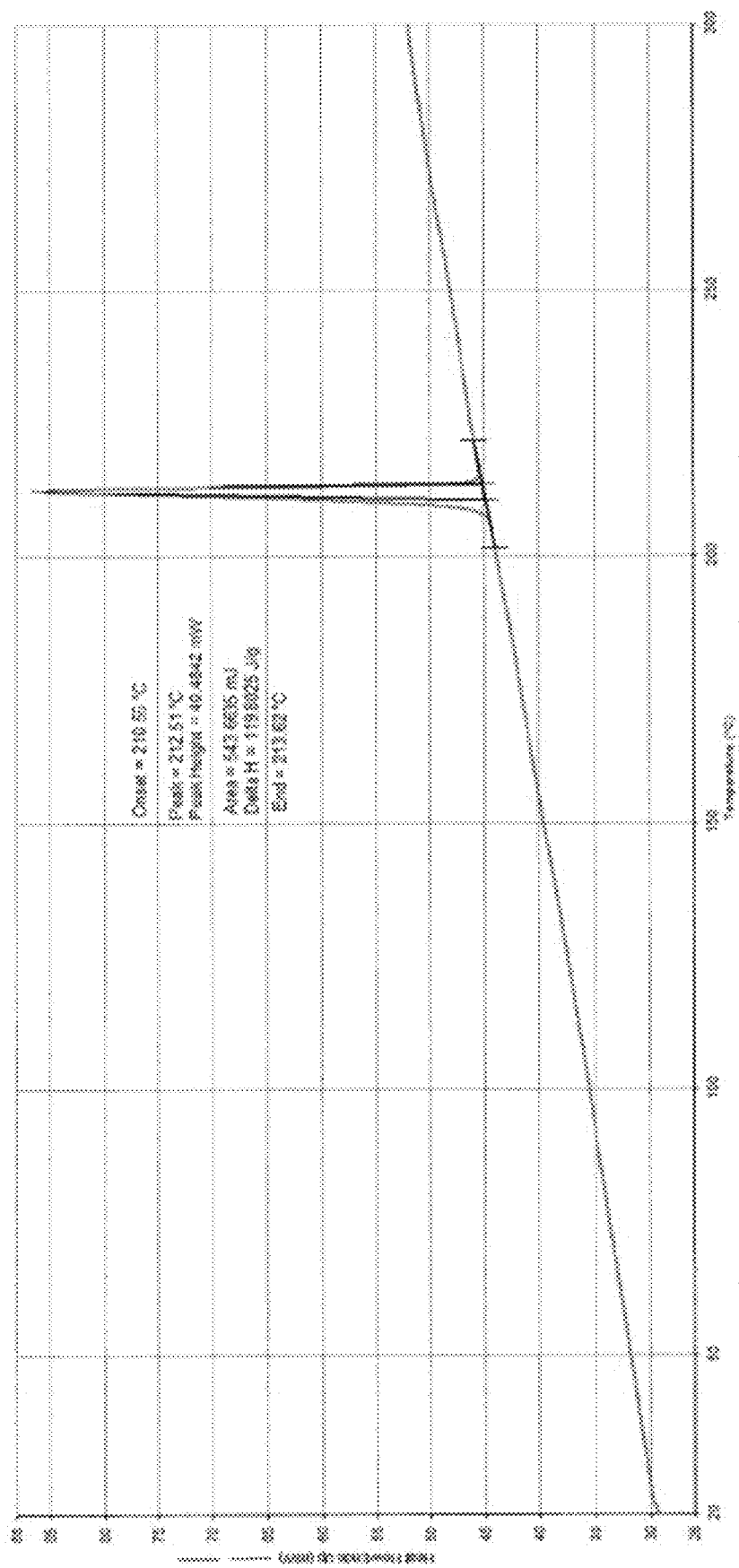
FIG. 12 shows a differential scanning calorimeter (DSC) thermogram of un-micronized imatinib
Figure 13:
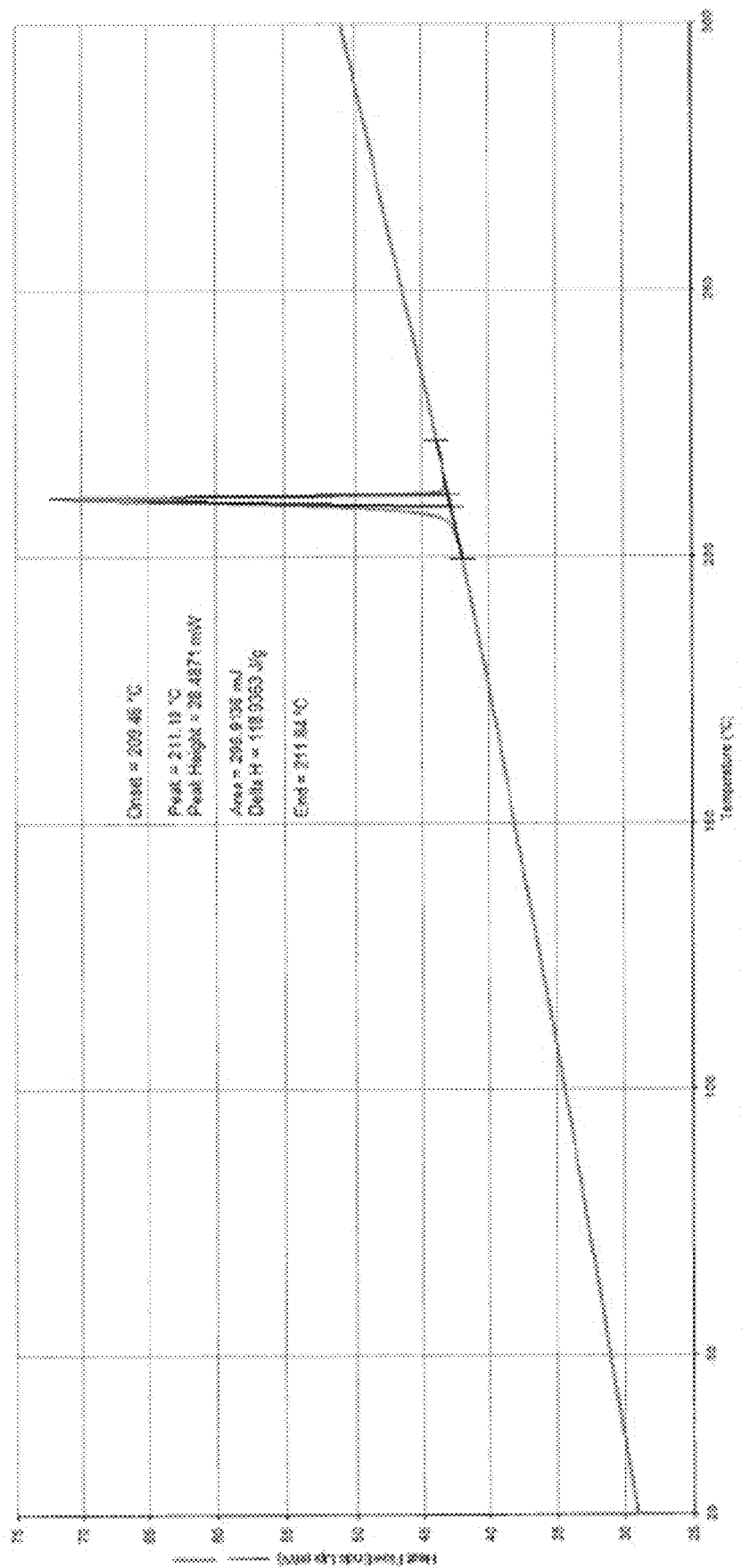
FIG. 13 shows a DSC thermogram of micronized imatinib.

The DSC thermograms of unmicronized and micronized imatinib are shown in FIGS. 12 and 13, respectively. DSC of the Free Base suggested a large endothermic event with an onset of ca. 210° C. (peak at ca. 212° C.), which was most likely associated with material melting. The imatinib exhibited similar DSC thermograms for both the un-micronized and micronized material with a melt onset of approx. 210° C. and peak enthalpies of approx. 119 J/g.

Figure 14:
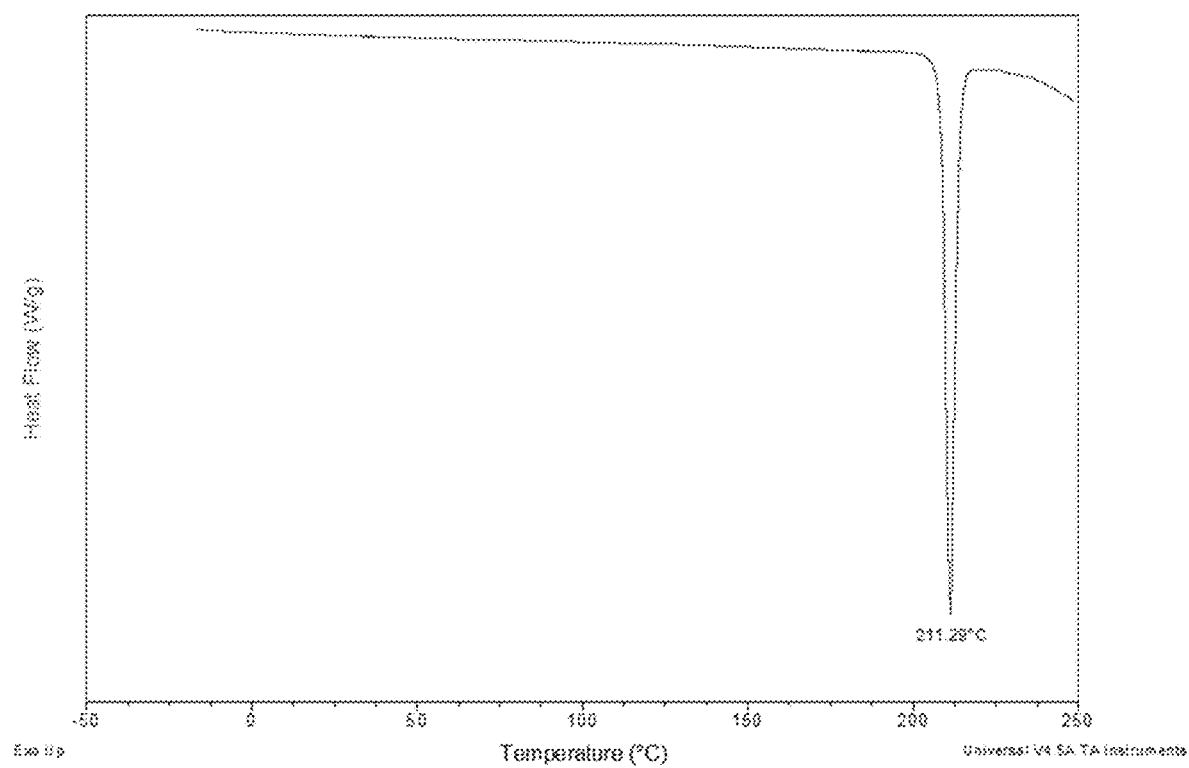
FIG. 14 shows a DSC thermogram of co-spray-dried imatinib with leucine.

The DSC trace of spray-dried Imatinib/leucine batch is shown in FIG. 14. The material shows a melting event at 211° C. associated with Imatinib melting. There was no cold crystallization or Tg. This suggests that the material remained completely crystalline.

The combination of lactose ML001 containing imatinib at 50% w/w was evaluated. This formulation was tested for the Total Lung Dose by Anatomical Throat (n=3), ED by DUSA with the High Resistance RS01 and PSD by Sympatec (0.5, 1 and 2 bar).

Figure 15:
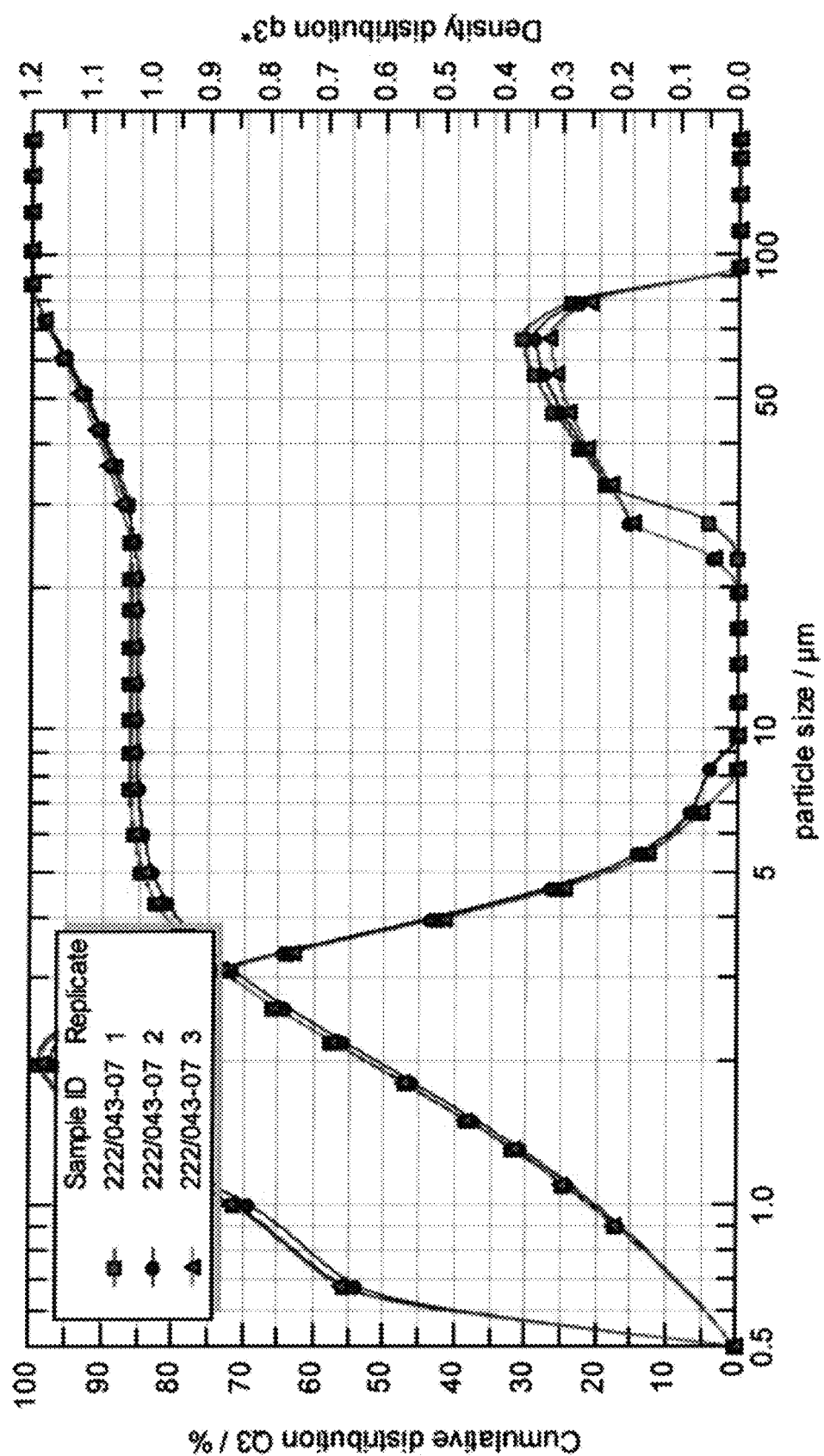
FIG. 15 shows PSD analysis of various carrier-based imatinib samples discussed in Example 2.

The capsule content uniformity and preliminary aerosolization data using a coated OPC anatomical throat are shown in Tables 5 and 6, respectively. In addition, the single actuation content is shown in Table 7. The particle sizing of the formulation is summarized in Table 8 and shown in FIG. 15.

TABLE 5

% Assay per 10 random capsules filled with carrier-based formulation.

| | Assay % |
|---|---|
| Sample 1 | 96.21 |
| Sample 2 | 98.27 |
| Sample 3 | 95.91 |
| Sample 4 | 94.21 |
| Sample 5 | 99.00 |
| Sample 6 | 96.51 |
| Sample 7 | 99.25 |
| Sample 8 | 98.17 |
| Sample 9 | 95.74 |
| Sample 10 | 96.24 |
| MEAN | 97.03 |
| STDEV | 1.713 |
| % RSD | 1.765 |
| USP <905> AV | 5.581 |

TABLE 6

Emitted dose, deposition in anatomical throat and total lung dose post aerosolization from a high-resistance RS01 at 60 L/min.

| | 1 | 2 | 3 | Average/mg | SD |
|---|---|---|---|---|---|
| Emitted Dose/mg | 6.65 | 7.16 | 6.13 | 6.64 | 0.51 |
| Anatomical Throat Deposition/mg | 1

TABLE 11-continued

Emitted dose by DUSA performed using a high-resistance RS01 at 60 L/min.

| | Target DD % |
|---|---|
| Sample 6 | 75.82 |
| Sample 7 | 74.05 |
| Sample 8 | 85.60 |
| Sample 9 | 80.04 |
| Sample 10 | 85.50 |
| MEAN | 79.4 |
| STDEV | 5.3 |
| % RSD | 6.72 |

Example 3: Evaluation of Dry Inhaler Formulation of Imatinib Free Base

The objective for this evaluation was to further identify the performance of imatinib free base when included into both blended and spray dried formulations. Four drug product batches were used, three spray-dried and one blended, for evaluation.

Materials

TABLE 12

Materials utilized in the study

| API | Batch No. | Quantity |
|---|---|---|
| Imatinib free base micronized | NP-106-18104-M | ~65 g |
| Leucine | 323170080 | 30 g |
| Lactose (ML001) | 10165XV | ~30 g |
| Qualicaps | Size 3 Medium Lubrification | — |

Analytical Methods

Air-Jet Micronization

Particle size reduction of Imatinib Free Base was performed using a 2-inch air jet mill (Food Pharma Systems, PM-2, Italy). The system was operated under nitrogen at a venturi and ring pressure of 8 bar and 7 bar, respectively. A total of 700.00 g of raw Imatinib Free Base material was micronized, twelve sub-lots of 50 g each in order to obtain at least 550 g (yield) of micronized material.

The rate at which the material was introduced into the mill was approximately 0.5 g/min. All samples were collected and stored in an amber glass jar, which was then sealed in an aluminium laminate pouch.

Micronized material was then used for the manufacture of Spray-Dried formulations (50:50, 75:25, 90:10) and a Carrier-Based formulation, 50 API:50 ML001, as described below.

Manufacture of Carrier-Based Dry Powder Inhaler Formulation using Micronized Imatinib The combination of lactose ML001 and Imatinib at a 50:50 ratio was evaluated positively so a larger scale of 30 g blend size was evaluated.

Part of the micronized material collected from the air-jet micronization was used to manufacture the formulation described above, using low shear blending. The STB-110 vessel was been used for the manufacture.

Figure 16:
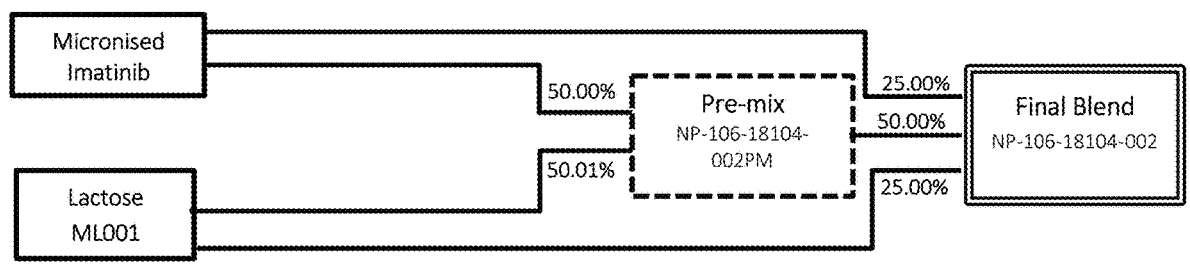
FIG. 16 shows an exemplary manufacturing scheme for a 50:50 Imatinib:Lactose blend.

The batch was NP-106-18104-002 and the process followed for the manufacture of this formulation is shown in FIG. 16.

Formulation Evaluation post Manufacture

The blended formulation was manufactured to equate to a 10 mg nominal dose per 20 mg of powder inside each capsule.

In order to make sure that the content of API was uniform within the formulation, it was submitted to Blend Content Uniformity testing. Samples from ten sections (FIG. 17) of the final formulation were taken and the amount of API in each sample was measured to confirm that it was at the same concentration in each part of the blend. The homogeneity of the final blend was assessed as per USP <905>.

After conducting blend content uniformity (BCU) measurements, the final blend (20.0±1.0 mg) was filled into size 3 HPMC capsules by using Omnidose TT.

Filled capsules were tested for emitted dose by DUSA and APSD using an OPC anatomical throat. An HR-RS01 (as-received high resistance device, Plastiape, Italy) was used for testing at 60 L/min.

Suspension Spray Drying

A feasibility batch was manufactured on small scale (10 g) using a Buchi B290 laboratory spray dryer. Micronized Imatinib was suspended in water at an API:Leucine ratio of 75:25, 50:50 and 90:10 w/w. The aspiration rate was at the highest setting, maximum suitable atomisation pressure of 4.0 bar, feed rate of 2-4 mL/min and within outlet temperature of 75° C. Spray drying conditions were checked by assessment of yield, powder appearance and PSD during the run.

Powders were collected under reduced humidity conditions and stored refrigerated at 2-8° C., in sealed containers. All formulations were filled into size 3 HPMC capsules for evaluation, using the following fill weights:
50:50, API:Leucine=20.0±1.0 mg
75:25, API:Leucine=13.3±0.7 mg
90:10, API:Leucine=11.1±0.6 mg Results: Blended Formulation and Suspension Spray-Dried Formulations Formulation Performance of High-Payload Carrier Based Formulation Containing Micronized Imatinib After the first part of the feasibility assessment, the combination of lactose ML001 for a formulation containing Imatinib with 50% of drug was evaluated positively, so a larger scale of 30 g blend size was evaluated. The formulation was tested for Aerodynamic Particle Size Distribution by NGI using an Anatomical Throat (n=3), ED by DUSA with High Resistance RS01. The batch was labelled as NP-106-18104-002.

Formulation Performance of Spray Drying Formulations

The aim of the second part of this study was to evaluate the combination of leucine for a formulation containing Imatinib with 75%, 50% and 90% drug loading. These preparations were manufactured by suspending the micronized Imatinib in an aqueous system with leucine and then spray drying the system. These formulations were tested in terms of Aerodynamic Particle Size Distribution (APSD) and Emitted Dose by DUSA, using the High Resistance RS01 Plastiape device. The target dose weight of the formulation in the capsule was equivalent to a nominal API dose of 10.00 mg.

Three batches of formulation containing varying weight ratios of imatinib: leucine (75:25, 90:10 & 50:50% w/w) were spray dried using a Buchi B290 spray dryer.

Feed solutions were prepared according to the details in Table 13—Overview of Spray-Dried formulations. For each solution, leucine was initially dissolved under stirring into deionised water. Once the leucine had fully dissolved, the micronized imatinib was added to create an opaque white suspension. Addition of the API resulted in some formation of foam. This appeared to be worse in the batches spray dried at higher API concentration (119 #008A/B).

TABLE 13

Overview of Spray-Dried formulations

| Batch# | API:Leucine ratio (% w/w) | API mass (g) | Leucine mass (g) | Total mass (g) | Volume of H$_2$O (mL) | % w/v Solids |
|---|---|---|---|---|---|---|
| 119#008A | 75:25 | 10.50 | 3.50 | 14.00 | 175 | 8 |
| 119#008B | 90:10 | 12.60 | 1.40 | 14.00 | 175 | 8 |
| 119#008C | 50:50 | 6.50 | 6.50 | 13.00 | 325 | 4 |

The feed solutions were spray dried according to the conditions detailed in Table. The feed solutions were constantly stirred during spray drying to avoid sedimentation of the suspended API during the run.

TABLE 14

Overview of Spray-Dried formulations

| Batch# | Liquid feed rate (g/min) | Inlet Temp. (° C.) | Outlet Temp. (° C.) | Atomisation pressure (bar) | Weight of product (g) | Yield (%) |
|---|---|---|---|---|---|---|
| 119#008A | 2 | 108-112 | 73-76 | 4 | 10.75 | 76.8 |
| 119#008B | 2 | 112-114 | 73-75 | 4 | 10.80 | 77.1 |
| 119#008C | 2 | 110-114 | 73-75 | 4 | 9.58 | 73.7 |

All three batches of formulation were successfully manufactured to produce fine white powders which were collected in similar yield from the collection pot. Losses appeared largely due to deposit of material on the walls of the spray chamber.

Blend Content Uniformity

Figure 17:
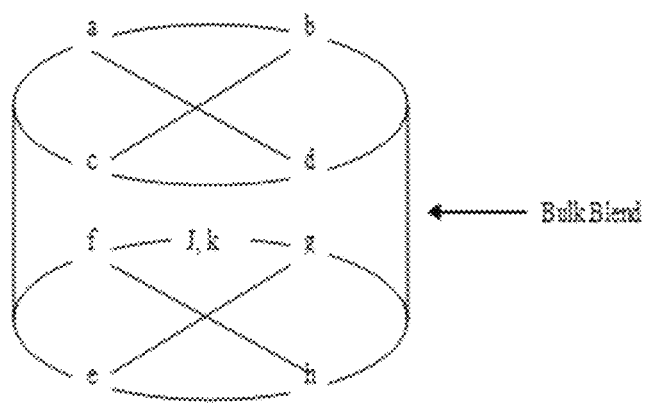
FIG. 17 shows an exemplary sampling strategy for BCU testing.
Figure 18:
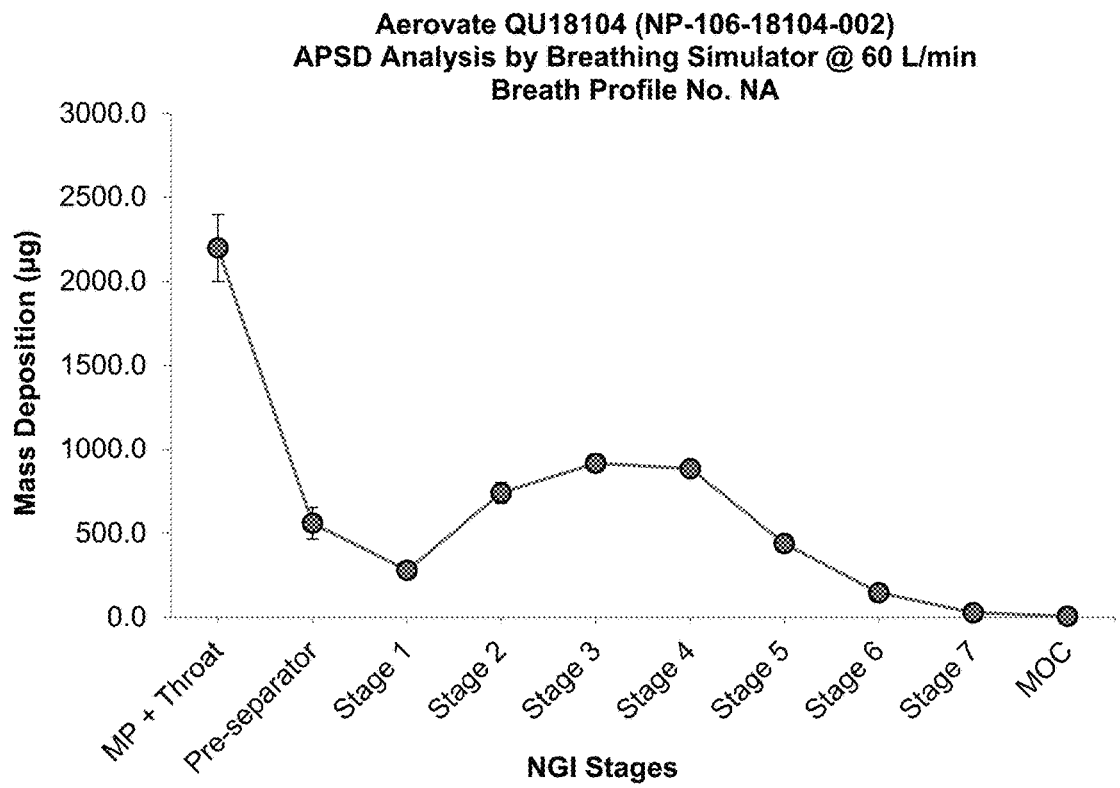
FIG. 18 shows an APSD profile for batch NP-106-18104-002 in Example 3.
Figure 19:
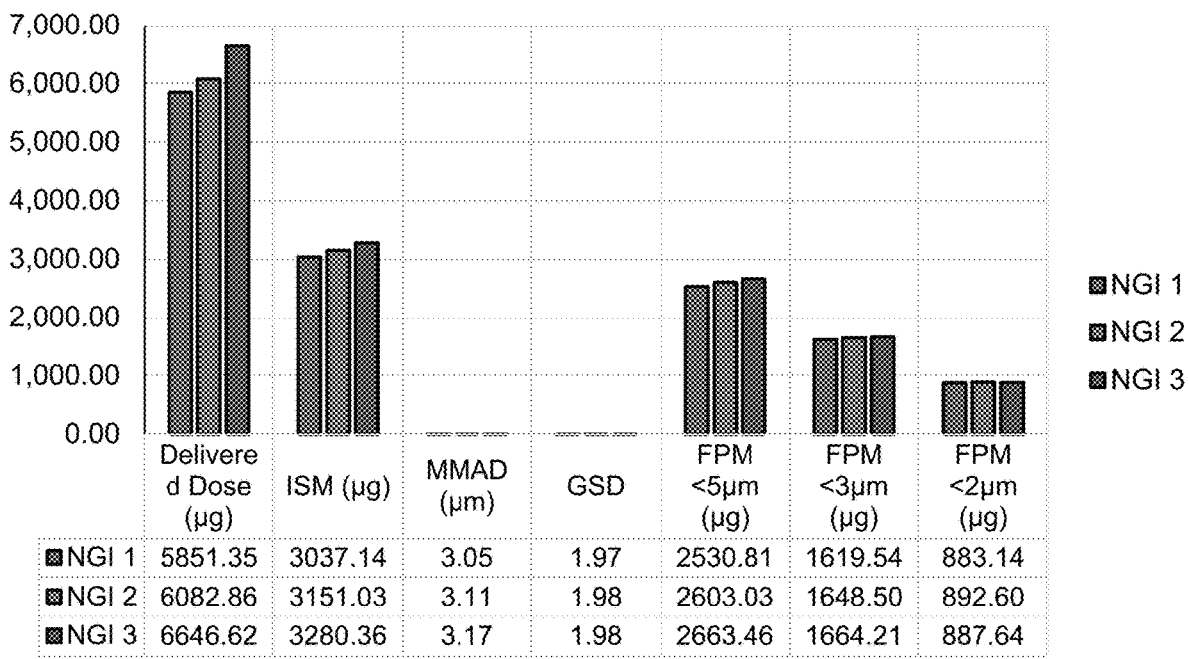
FIG. 19 shows Metrics Results for batch NP-106-18104-002 in Example 3.
Figure 20:
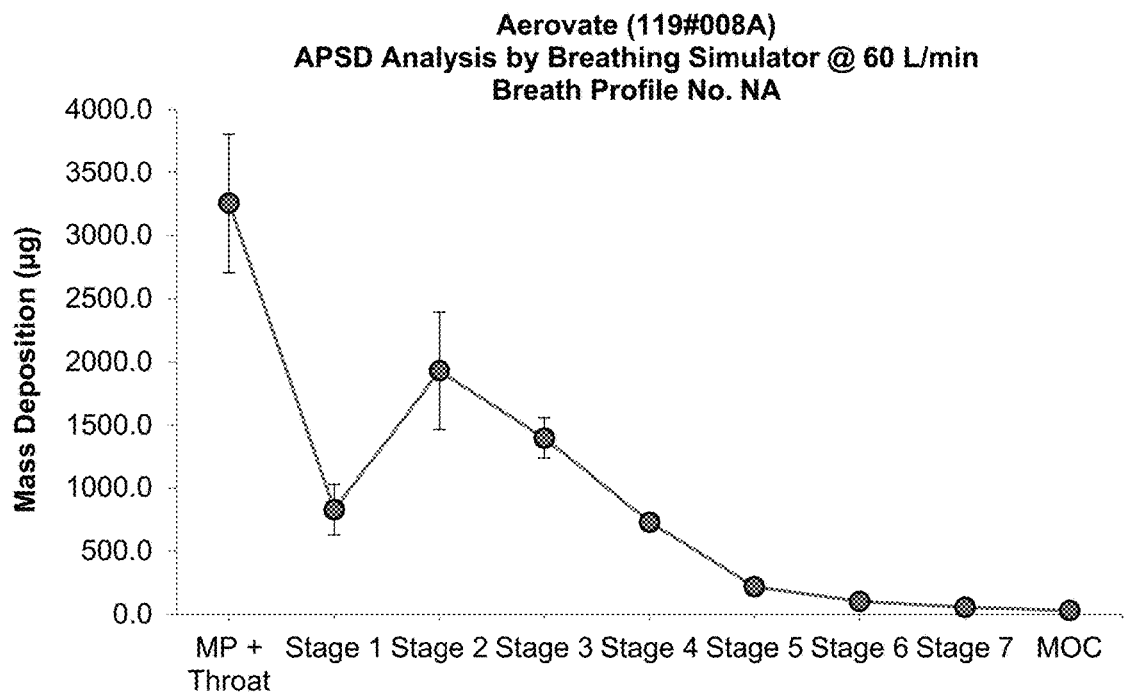
FIG. 20 shows an APSD profile for a 75:25 Imatinib: Lactose Spray-Dried formulation.
Figure 21:
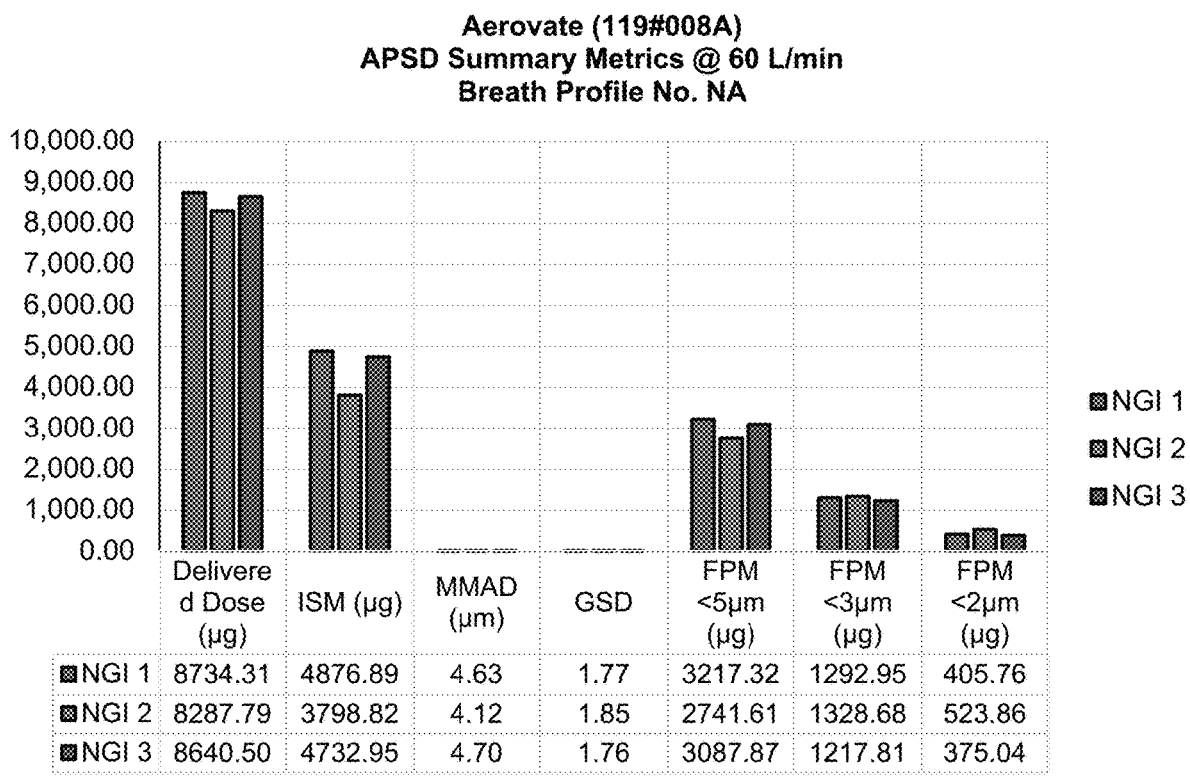
FIG. 21 shows Metrics Results for a 75:25 Imatinib: Lactose Spray-Dried formulation.
Figure 22:
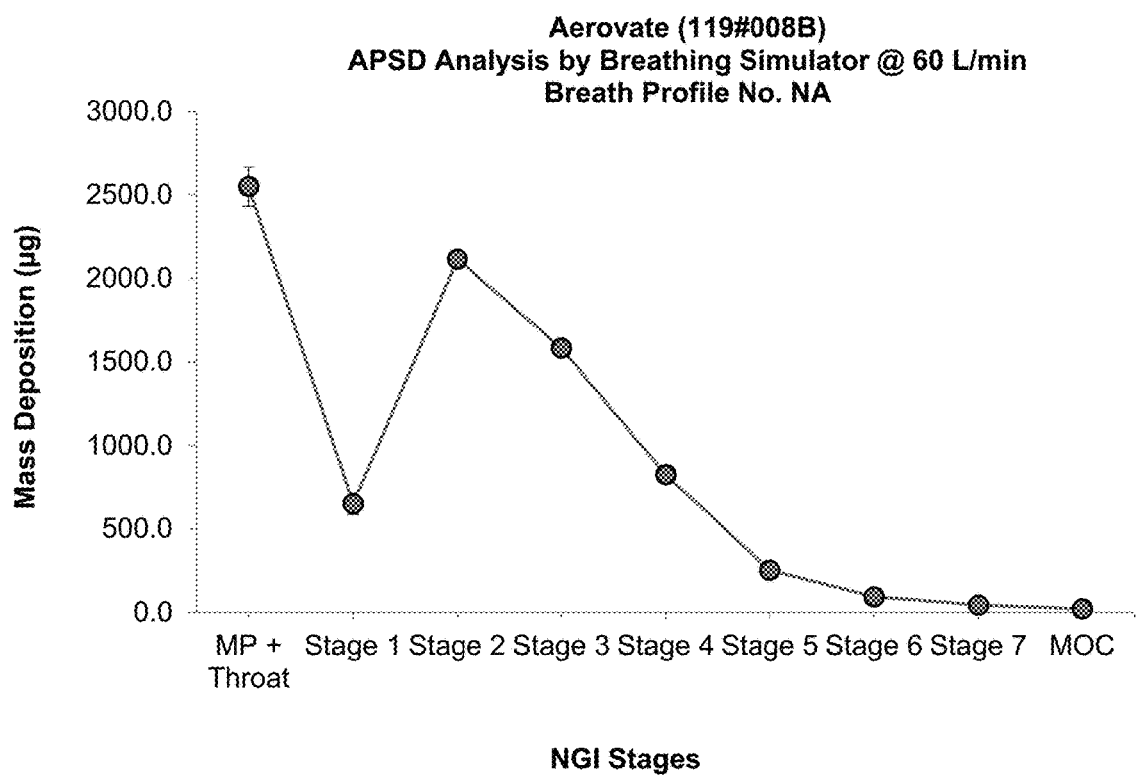
FIG. 22 shows an APSD profile for a 90:10 Imatinib: Lactose Spray-Dried formulation.
Figure 23:
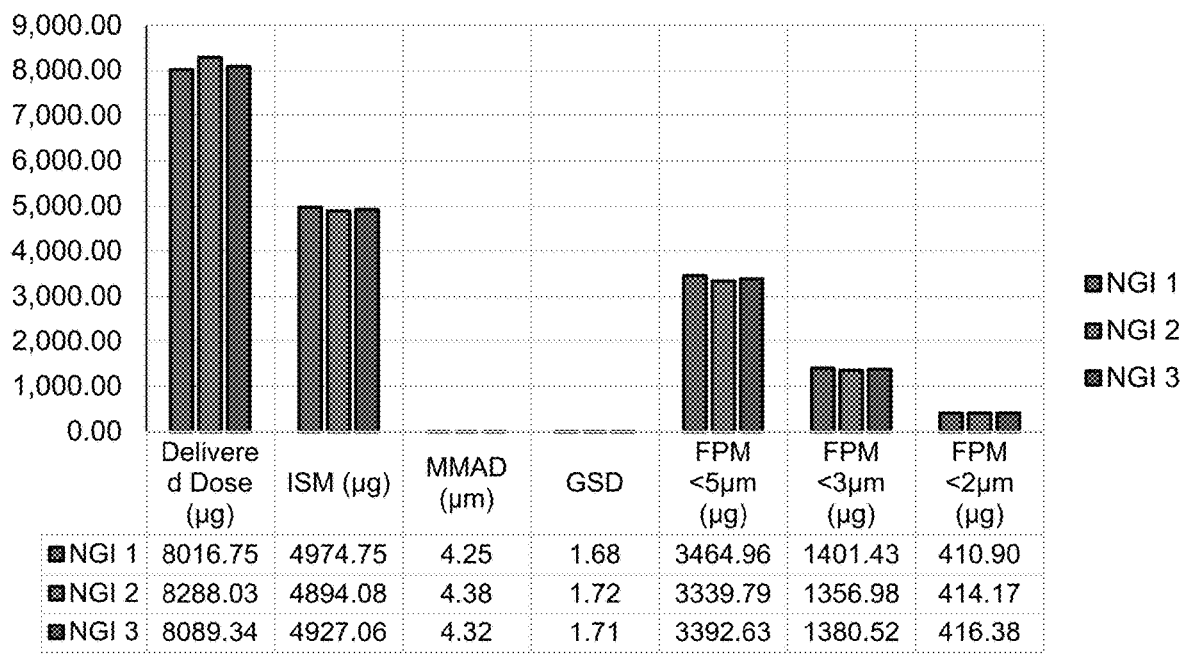
FIG. 23 shows Metrics Results for a 90:10 Imatinib: Lactose Spray-Dried formulation.
Figure 24:
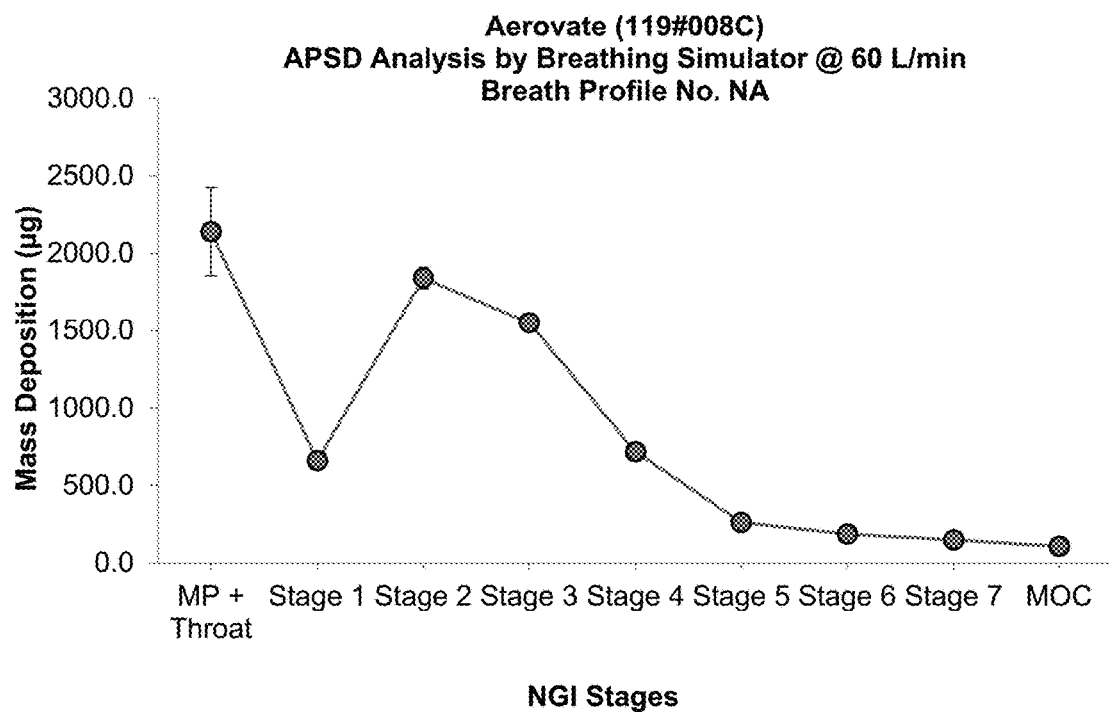
FIG. 24 shows an APSD profile for a 50:50 Imatinib: Lactose Spray-Dried formulation.
Figure 25:
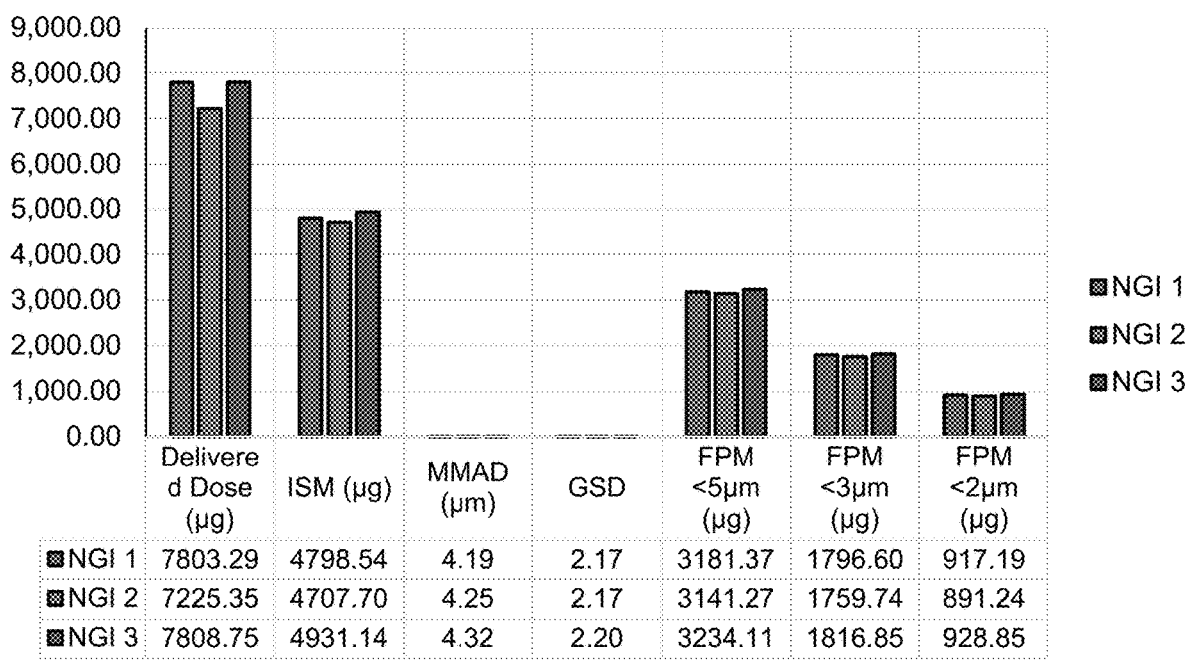
FIG. 25 shows Metrics Results for a 50:50 Imatinib: Lactose Spray-Dried formulation.
Figure 26:
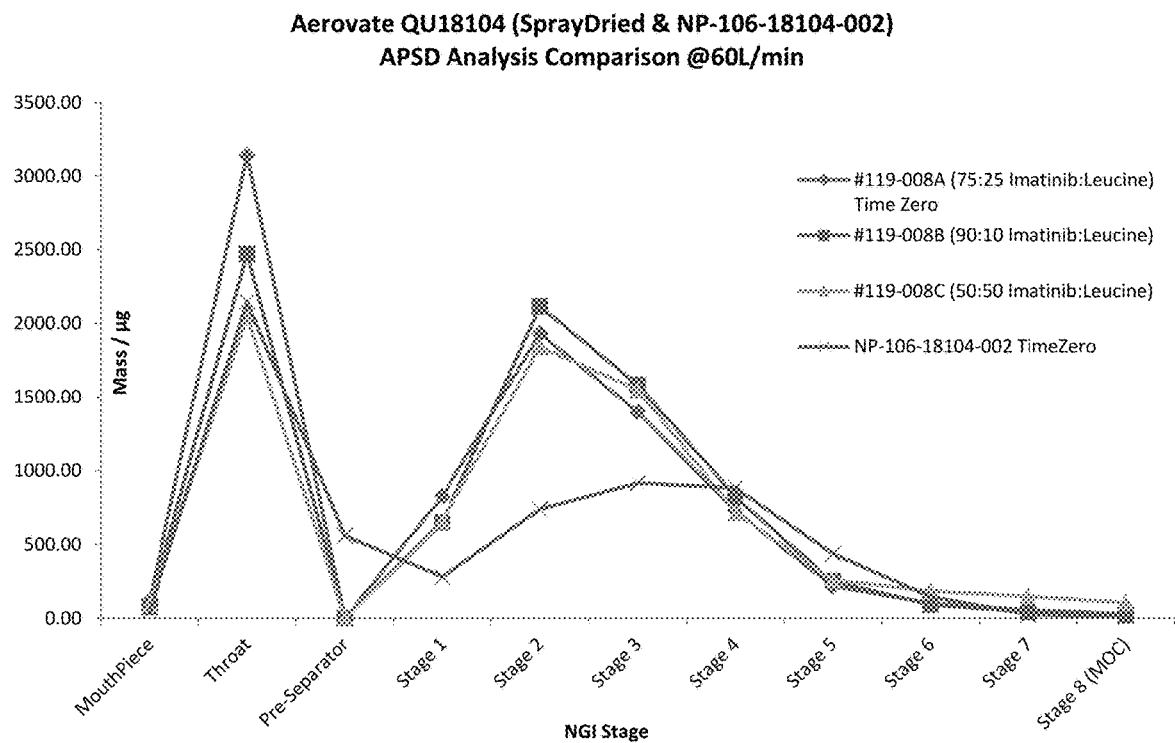
FIG. 26 shows an APSD Comparison profile for various Spray-Dried and Carrier Based DPI (Dry Powder Inhaler) Formulations.
Figure 27:
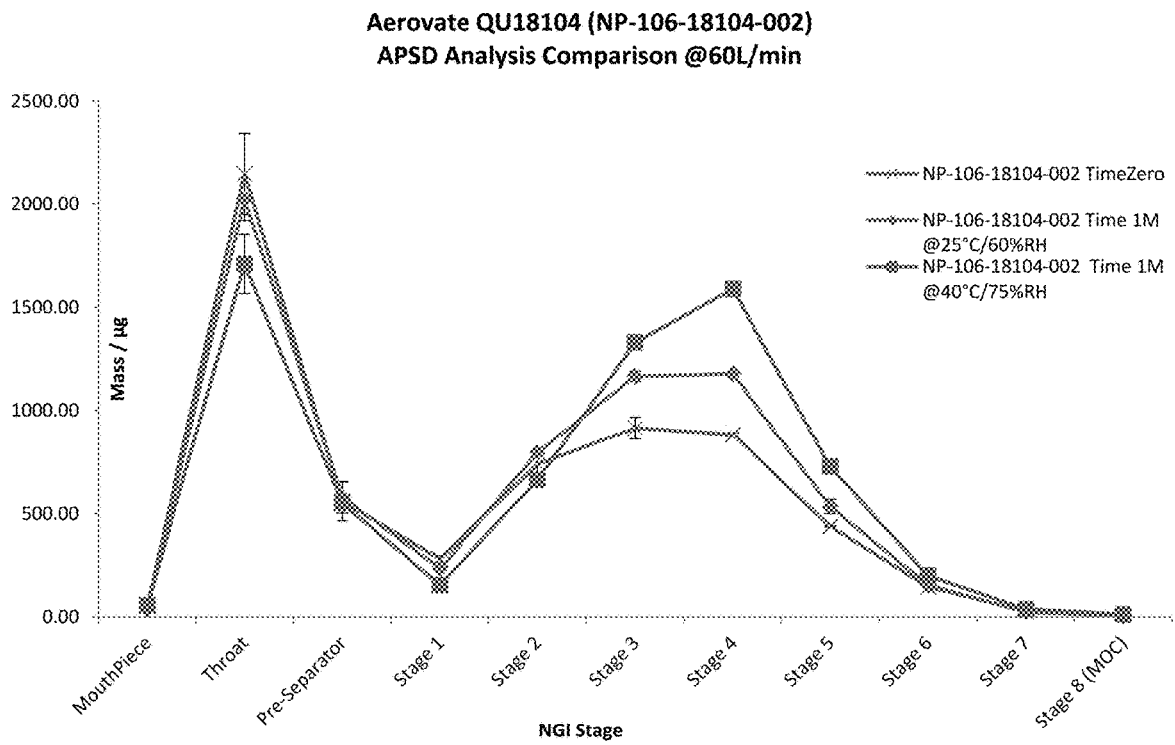
FIG. 27 shows an APSD Comparison profile for batch NP-106-18104-002 at Time Zero and Time 1 Month under two storage conditions as detailed in Example 3.
Figure 28:
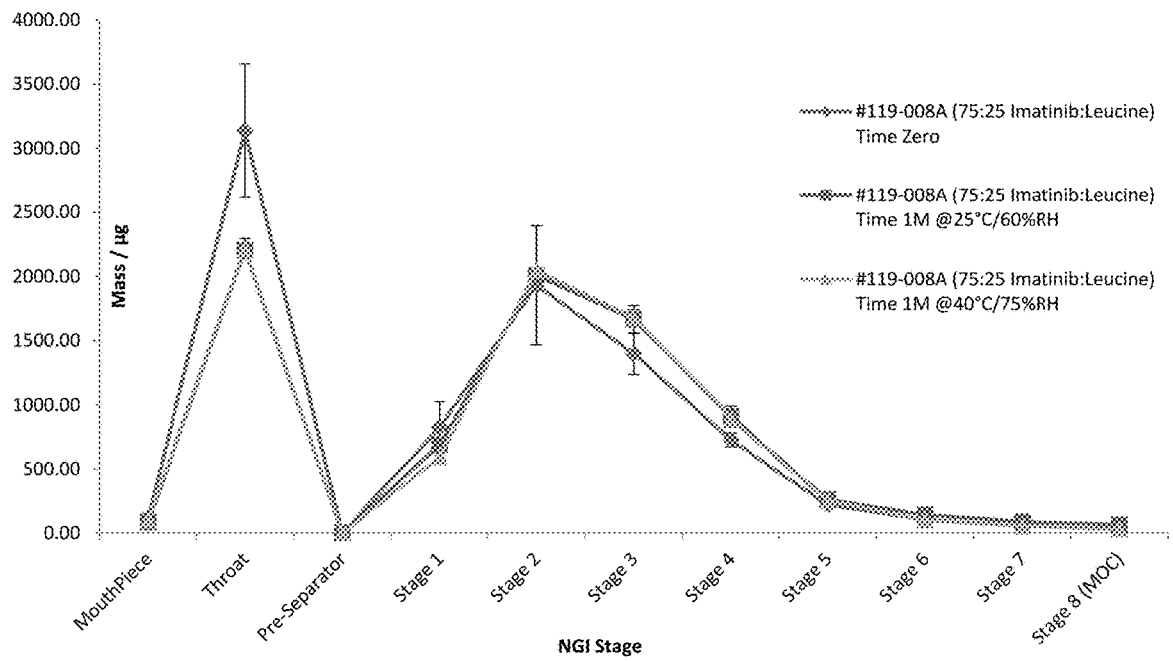
FIG. 28 shows an APSD Comparison profile for a 75:25 Imatinib:Lactose Spray-Dried formulation at Time Zero and Time 1 Month under two storage conditions as detailed in Example 3.
Figure 29:
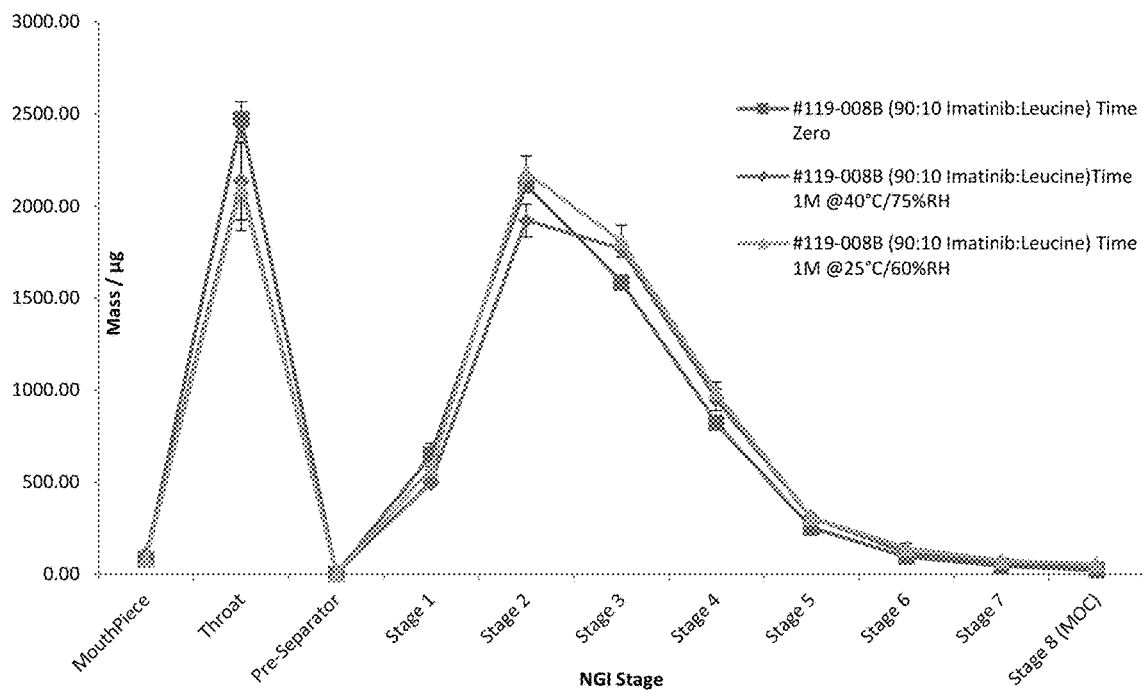
FIG. 29 shows an APSD Comparison profile for a 90:10 Imatinib:Lactose Spray-Dried formulation at Time Zero and Time 1 Month under two storage conditions as detailed in Example 3.
Figure 30:
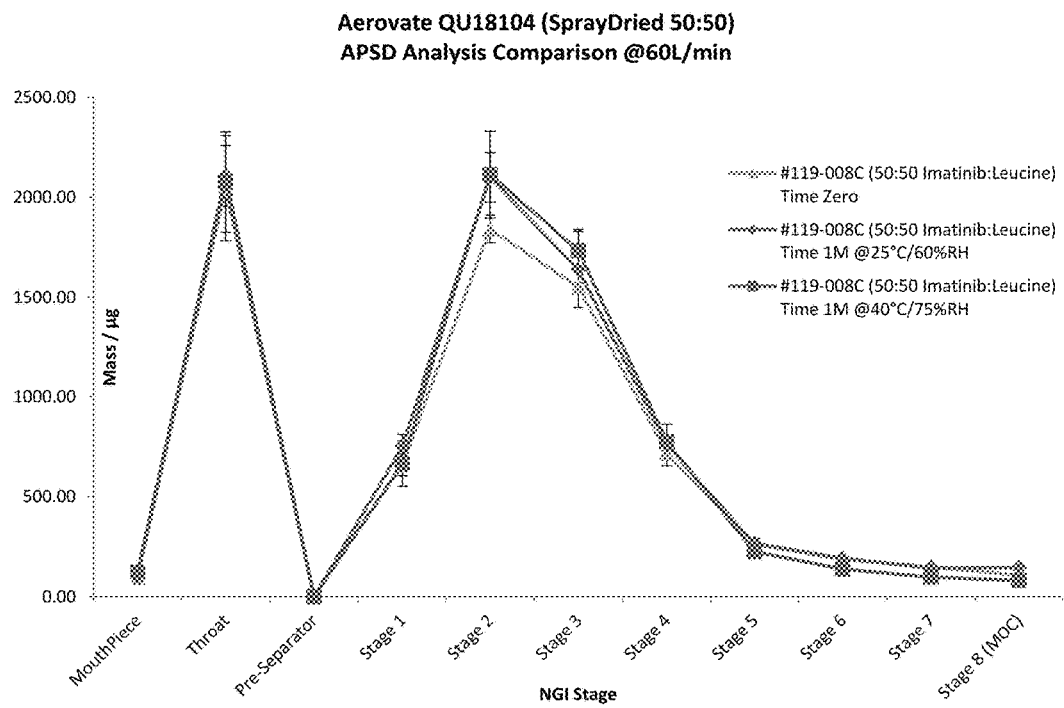
FIG. 30 shows an APSD Comparison profile for a 50:50 Imatinib:Lactose Spray-Dried formulation at Time Zero and Time 1 Month under two storage conditions as detailed in Example 3.

Blend content uniformity (BCU) testing was performed and results are summarized in the table below (Table 15) taken from ten sections (FIG. 17). These data suggest the formulation NP-106-18104-002 was homogenous and met USP <905> acceptance criteria.

TABLE 15

Blend Content Uniformity Results post blend manufacture

| Batch | % Theoretical Yield | % w/w | USP <905> AV | RSD (%) | Results |
|---|---|---|---|---|---|
| NP-106-18104-002 | 98.52% | 49.25% | 6.22 | 2.63% | PASS |

Capsule Content Uniformity

All formulations were filled into capsules using the Harro Hoffliger OmniDose TT filling system. A target fill weight of 20 mg was used with a +/−5% range. The results from these filling trials can be found in Table and 17. These data suggest the capsule content uniformity met the USP <905> acceptance criteria.

TABLE 16

Capsule filling data for all formulations filled

| Batch | Pressure (bar) | Number of repetitions | Mean value of the mass (mg) | RSD (%) | Amount of capsules filled |
|---|---|---|---|---|---|
| NP-106-18104-002 | 0.38 | 2 | 19.95 | 3.13 | 135 |

TABLE 17

Capsule Content Uniformity of all formulations successfully manufactured

| Batch | % Theoretical Yield | USP <905> AV | RSD (%) | Results |
|---|---|---|---|---|
| NP-106-18104-002 | 9.41 | 10.25 | 2.60 | PASS |

Emitted Dose by DUSA

The emitted dose as determined from single actuation content measurements using the high-resistance RS01 are shown in Table. The average emitted dose of the formulation blended with lactose was approximately 7 mg and this resulted in 74% emitted fraction. The average emitted dose of the spray dried formulations was approximately 8.74 mg and this resulted in 87% emitted fraction.

TABLE 18

Emitted Dose by DUSA Results post blend manufacture

| Batch | API:ML001/Leucine ratio (% w/w) | ED (%) | Emitted Dose/mg | RSD (n = 10) |
|---|---|---|---|---|
| NP-106-18104-002 | 50:50 | 74 | 6.96 | 8 |
| 119#008A | 75:25 | 88 | 8.83 | 10 |
| 119#008B | 90:10 | 82 | 8.21 | 7 |
| 119#008C | 50:50 | 92 | 9.20 | 5 |

Aerodynamic Particle Size Distribution (APSD) by NGI

APSD analysis was carried out firstly using the standard High Resistance RS01 at 60 L/min, using an OPC anatomical throat, and the results summary is shown in Table 19 and Error! Reference source not found. for the Carrier Based DPI formulation 50 ML001: 50 Imatinib.

The emitted dose was 6 mg and fine particle mass less than 5 μm (FPM<5 μm) was 2.6 mg. The MMAD was 3.1 μm and the GSD was 2 μm.

A results summary is shown in the same table below and FIGS. 20-26 for the three Spray-Dried formulations with an emitted dose between 8.55-7.61 μm and a fine particle mass less than 5 μm (FPM<5 μm) between 3.01 and 3.18 mg.

The MMAD were 4.48-4.25 μm and the GSD was 1.76-2.18 μm.

TABLE 19

APSD by NGI Performance Metric Results post blend manufacture

| Batch | API:ML001/Leucine ratio (% w/w) | MB (%) | ED (mg) | ISM (mg) | MMAD (mm) | GSD | FPM < 5 μm (mg) |
|---|---|---|---|---|---|---|---|
| NP-106-18104-002 | 50:50 | 89 | 6.19 | 3.16 | 3.11 | 1.98 | 2.60 |
| 119#008A | 75:25 | 97 | 8.55 | 4.47 | 4.48 | 1.76 | 3.01 |
| 119#008B | 90:10 | 99 | 8.13 | 4.93 | 4.32 | 1.70 | 3.34 |
| 119#008C | 50:50 | 83 | 7.61 | 4.81 | 4.25 | 2.18 | 3.18 |

Results: Stability at 1 Month at 25° C./60% RH and 40° C./75% RH

Emitted Dose by DUSA

The emitted dose was determined from single actuation content measurements using the high-resistance RS01 and are shown in Table.

TABLE 20

Emitted Dose by DUSA Results post blend manufacture

| Batch | API:ML001/Leucine ratio (% w/w) | Conditions | ED (%) | Emitted Dose/mg | RSD (n = 10) |
|---|---|---|---|---|---|
| Time Zero | | | | | |
| NP-106-18104-002 | 50:50 | — | 74 | 6.96 | 8 |
| Time 1 Month | | | | | |
| NP-106-18104-002 | 50:50 | 25° C./60% RH | 69 | 6.92 | 3 |
| | | 40° C./75% RH | 73 | 7.33 | 3 |
| Time Zero | | | | | |
| 119#008A | 75:25 | — | 88 | 8.83 | 10 |
| Time 1 Month | | | | | |
| 119#008A | 75:25 | 25° C./60% RH | 95 | 9.46 | 2 |
| | | 40° C./75% RH | 93 | 9.28 | 3 |
| Time Zero | | | | | |
| 119#008B | 90:10 | — | 82 | 8.21 | 7 |
| Time 1 Month | | | | | |
| 119#008B | 90:10 | 25° C./60% RH | | | |
| | | 40° C./75% RH | 87 | 8.74 | 6 |
| Time Zero | | | | | |
| 119#008C | 50:50 | — | 92 | 9.20 | 5 |
| Time 1 Month | | | | | |
| 119#008C | 50:50 | 25° C./60% RH | | | |
| | | 40° C./75% RH | 93 | 9.32 | 3 |

Aerodynamic Particle Size Distribution (APSD) by NGI

APSD analysis was carried out firstly using the standard High Resistance RS01 at 60 L/min, using an OPC anatomical throat, and the results summary is shown in Table 2 and in FIGS. 12-15 for the Carrier Based DPI formulation and various spray-dried formulations.

TABLE 21

APSD by NGI Performance Metric Results post blend manufacture

| Batch | API:ML001/Leucine ratio (% w/w) | Conditions | MB (%) | ED (mg) | ISM (mg) | MMAD (μm) | GSD | FPM < 5 μm (mg) |
|---|---|---|---|---|---|---|---|---|
| Time Zero | | | | | | | | |
| NP-106-18104-002 | 50:50 | — | 89 | 6.19 | 3.16 | 3.11 | 1.98 | 2.60 |
| Time 1 Month | | | | | | | | |
| NP-106-18104-002 | 50:50 | 25° C./60% RH | 96 | 6.65 | 3.80 | 2.98 | 1.85 | 3.24 |
| | | 40° C./75% RH | 96 | 7.03 | 4.56 | 2.63 | 1.76 | 4.12 |
| Time Zero | | | | | | | | |
| 119#008A | 75:25 | — | 97 | 8.55 | 4.47 | 4.48 | 1.76 | 3.01 |
| Time 1 Month | | | | | | | | |
| 119#008A | 75:25 | 25° C./60% RH | 86 | 8.04 | 5.14 | 4.17 | 1.76 | 3.65 |
| | | 40° C./75% RH | 86 | 7.97 | 5.06 | 4.18 | 1.70 | 3.57 |
| Time Zero | | | | | | | | |
| 119#008B | 90:10 | — | 99 | 8.13 | 4.93 | 4.32 | 1.70 | 3.34 |

TABLE 21-continued

APSD by NGI Performance Metric Results post blend manufacture

| Batch | API:ML001/Leucine ratio (% w/w) | Conditions | MB (%) | ED (mg) | ISM (mg) | MMAD (µm) | GSD | FPM < 5 µm (mg) |
|---|---|---|---|---|---|---|---|---|
| | | Time 1 Month | | | | | | |
| 119#008B | 90:10 | 25° C./60% RH | | 8.32 | 5.56 | 4.15 | 1.90 | 3.80 |
| | | 40° C./75% RH | 90 | 7.91 | 5.16 | 4.03 | 1.85 | 3.62 |
| | | Time Zero | | | | | | |
| 119#008C | 50:50 | — | 83 | 7.61 | 4.81 | 4.25 | 2.18 | 3.18 |
| | | Time 1 Month | | | | | | |
| 119#008C | 50:50 | 25° C./60% RH | | 8.20 | 5.24 | 4.26 | 1.91 | 3.59 |
| | | 40° C./75% RH | 86 | 8.02 | 5.16 | 4.25 | 1.71 | 3.60 |

Relative Substances by High Performance Liquid Chromatography

Further analysis was performed through High Performance Liquid Chromatography (HPLC) and minor relative substance was detected and otherwise quantified and reported in Table 22 below along with the relative Assay Area Percentage (Table 23) for Spray Dried formulations and Carrier Based DPI Formulation, NP-106-18104-002 after 1 M at 25° C./60% RH and 40° C./75% RH.

None were above 0.10% as Reporting Limits suggested. Also, the total percentage of all the Relative Substances was below 0.50% for the micronized API and all the formulations analysed.

TABLE 22

Relative substances detected for Time 1 Month
Time 1 Month

| | Unknown Relative Substance | RT | RRT | Area | Area % |
|---|---|---|---|---|---|
| | 119#008A (75:25) | | | | |
| T = 0 | | ND | | | |
| @25° C./60% RH | RS1 | 7.26 | 0.74 | 0.88 | 0.02 |
| | RS2 | 7.79 | 0.80 | 0.10 | 0.00 |
| | RS3 | 11.36 | 1.17 | 0.29 | 0.01 |
| | RS4 | 11.81 | 1.21 | 0.05 | 0.00 |
| @40° C./75% RH | RS1 | 7.17 | 0.74 | 0.55 | 0.01 |
| | RS2 | 7.51 | 0.78 | 0.06 | 0.00 |
| | RS3 | 8.25 | 0.86 | 0.09 | 0.00 |
| | RS4 | 8.88 | 0.92 | 0.09 | 0.00 |
| | RS5 | 10.90 | 1.13 | 0.15 | 0.00 |
| | RS6 | 11.10 | 1.15 | 0.04 | 0.00 |
| | RS7 | 11.30 | 1.17 | 0.49 | 0.01 |
| | RS8 | 11.54 | 1.20 | 0.31 | 0.01 |
| | 119#008B (90:10) | | | | |
| T = 0 | | ND | | | |
| @25° C./60% RH | RS1 | 7.25 | 0.74 | 0.56 | 0.01 |
| | RS2 | 7.88 | 0.81 | 0.07 | 0.00 |
| | RS3 | 11.40 | 1.17 | 0.33 | 0.01 |
| | RS4 | 11.89 | 1.22 | 0.13 | 0.00 |
| @40° C./75% RH | RS1 | 7.18 | 0.75 | 0.64 | 0.02 |
| | RS2 | 7.47 | 0.78 | 0.07 | 0.00 |
| | RS3 | 8.25 | 0.86 | 0.06 | 0.00 |
| | RS4 | 8.90 | 0.93 | 0.08 | 0.00 |
| | RS5 | 10.97 | 1.15 | 0.07 | 0.00 |
| | RS6 | 11.22 | 1.18 | 0.02 | 0.00 |
| | RS7 | 11.31 | 1.19 | 0.43 | 0.01 |
| | RS8 | 11.57 | 1.21 | 0.38 | 0.01 |
| | 119#008C (50:50) | | | | |
| T = 0 | | ND | | | |
| @25° C./60% RH | RS1 | 7.22 | 0.74 | 0.80 | 0.02 |
| | RS2 | 7.83 | 0.81 | 0.11 | 0.00 |
| | RS3 | 11.34 | 1.17 | 0.42 | 0.01 |
| | RS4 | 11.94 | 1.23 | 0.12 | 0.00 |
| @40° C./75% RH | RS1 | 7.26 | 0.75 | 0.67 | 0.02 |
| | RS2 | 7.52 | 0.78 | 0.11 | 0.00 |
| | RS3 | 8.24 | 0.85 | 0.09 | 0.00 |
| | RS4 | 8.92 | 0.92 | 0.18 | 0.00 |
| | RS5 | 10.96 | 1.13 | 0.13 | 0.00 |
| | RS6 | 11.22 | 1.16 | 0.16 | 0.00 |
| | RS7 | 11.35 | 1.17 | 0.50 | 0.01 |
| | RS8 | 11.59 | 1.20 | 0.43 | 0.01 |
| | NP-106-104-002 | | | | |
| T = 0 | | ND | | | |
| @25° C./60% RH | RS1 | 7.23 | 0.74 | 0.50 | 0.01 |
| | RS2 | 7.83 | 0.80 | 0.15 | 0.00 |
| | RS3 | 11.39 | 1.17 | 0.41 | 0.01 |
| | RS4 | 11.85 | 1.22 | 0.15 | 0.00 |
| @40° C./75% RH | RS1 | 7.24 | 0.75 | 0.48 | 0.01 |
| | RS2 | 7.44 | 0.77 | 0.11 | 0.00 |
| | RS3 | 8.31 | 0.86 | 0.11 | 0.00 |
| | RS4 | 8.90 | 0.92 | 0.09 | 0.00 |
| | RS5 | 10.91 | 1.12 | 0.18 | 0.00 |
| | RS6 | 11.17 | 1.15 | 0.15 | 0.00 |
| | RS7 | 11.36 | 1.17 | 0.34 | 0.01 |
| | RS8 | 11.61 | 1.20 | 0.46 | 0.01 |

TABLE 23

Assay Area Percentage

| Batch | API:ML001/Leucine ratio (% w/w) | Conditioning | Assay Area % |
|---|---|---|---|
| NP-106-104-002 | 50:50 | @25° C./60% RH | 99.97 |
| | | @40° C./75% RH | 99.95 |
| 119#008A | 75:25 | @25° C./60% RH | 99.97 |
| | | @40° C./75% RH | 99.96 |
| 119#0008B | 90:10 | @25° C./60% RH | 99.97 |
| | | @40° C./75% RH | 99.96 |
| 119#008C | 50:50 | @25° C./60% RH | 99.96 |
| | | @40° C./75% RH | 99.94 |

Example 4: 3 Month Stability Characterization

The aim of this study was to perform initial physicochemical characterization of unmicronized Imatinib Free Base using an array of techniques. The unmicronized form of the drug was then processed by micronization and blended with lactose or spray dried and characterized after being placed into stability at 40° C./75% RH and @25° C./60% RH for 1 Month and 3 Months.

Materials

The samples for use within this study and are listed in Table 24.

TABLE 24

Materials utilized in the study

| API | Batch No. | Quantity |
|---|---|---|
| Imatinib free base (Dry Powder) | NP-106-004 | 1 Kg |
| Carrier Based DPI Formulation | NP-106-104-002 | 30 g |
| Spray Dried 75:25 | #119-008A | 10 g |
| Spray Dried 50:50 | #119-008B | 10 g |
| Spray Dried 90:10 | #119-008C | 10 g |

Methods

Air-Jet Micronization

Particle size reduction of Imatinib Free Base was performed using a 2-inch air jet mill (Food Pharma Systems, PM-2, Italy). The system was operated under nitrogen at a venturi and ring pressure of 8 bar and 7 bar, respectively. A total of 600.00 g of raw Imatinib Free Base material was micronized, twelve sub-lots of 50g each in order to obtain at least 550 g (yield) of micronized material.

The rate at which the material was introduced into the mill was approximately 0.5 g/min. All samples were collected and stored in an amber glass jar, which was then sealed in an aluminium laminate pouch.

Suspension Spray Drying

A feasibility batch was manufactured on small scale (10 g) using a Buchi B290 laboratory spray dryer. Micronized Imatinib was suspended in water at API:Leucine ratios of 75:25, 50:50 and 90:10 w/w. The aspiration rate was at the highest setting, maximum suitable atomisation pressure of 4.0 bar, feed rate of 2-4 mL/min and within outlet temperature of 75° C. Spray drying conditions were checked by assessment of yield, powder appearance and PSD during the run.

Powders were collected under reduced humidity conditions and stored refrigerated at 2-8° C., in sealed containers.

All formulations were filled into size 3 HPMC capsules for evaluation, using the following fill weights:
50:50, API:Leucine=20.0±1.0 mg
75:25, API:Leucine=13.3±0.7 mg
90:10, API:Leucine=11.1±0.6 mg

Dry Powder Particle Size Distribution Analysis

For particle sizing, unmicronized Imatinib was dispersed with compressed air (2 bar) and sized by laser diffraction (RODOS dry powder feeder; HELOS laser diffractometer, WINDOX 4.0 software; Sympatec GmbH, Germany). The 10, 50 and 90% undersize particle size values (X10, X50 and X90, respectively) were obtained. To evaluate the extent of cohesion between particles, values of X50 were measured (n=3) over the pressure range of 1-3 bar for the micronized material.

Specific Surface Area

The specific surface area (SSA) of Imatinib samples (0.6 g) was measured using a Micrometrics TriStar 3000 surface area analyser (Micromeritics Instrument Corporation, Norcross, USA). An eleven-point BET nitrogen adsorption analysis was carried out in duplicate after degassing the samples for 16 hours in a FlowPrep 060 degasser at 25° C. (Micromeritics Instrument Corporation, Norcross, USA).

X-Ray Powder Diffraction

To determine the X-ray powder diffraction (XRPD) pattern of the Imatinib samples, all samples were analysed on a Bruker Powder Diffractometer (D8; Bruker AXS Inc., Madison, USA) using CuK$\alpha$ radiation ($\lambda$=1.54 Å). The data were collected over a single 2$\theta$ sweep with range 2$\theta$=2–40° 2$\theta$ and step time 0.2 s.

The samples were analysed in deep fill silicon sample holders. Each sample was packed into the well and levelled to ensure a flat surface without introducing possible preferred orientation. The samples were analysed using a PANalytical diffractometer set at 40 kV and 40 mA with a Cu source, using a 0.5 mm Ni filter to remove K$\beta$ interference. 0.6 mm divergence slits, 1 mm anti-scatter slits and 2.5° soller slits in the primary and secondary optics were used.

The instrument was fitted with a Lynxeye detector and data was collected over a range of 10-80° 2$\theta$, with a step size of 0.05°, a scan speed of 0.03°/sec and a step time of 494 sec/step. The samples were spun at a rate of 15 rpm to reduce any preferred orientation affects. Prior to sample analysis, a corundum standard was analysed to ensure instrument alignment.

Differential Scanning Calorimetry & Thermal Gravimetric Analysis

DSC analysis was undertaken using a TA Instruments Q20 MDSC with auto sampler and refrigerated cooling accessory. Approximately 1-4 mg of sample was tested in a T Zero aluminium pan under an N2 flow (50 mL/min). Pans were sealed using a T Zero pan press. The following cycle was used:
Data storage: Off
Equilibrate at −20.00° C.
Isothermal for 5.00 min
Data storage: On
Ramp 10.00° C./min to 250.00° C.
Isothermal for 5.00 min
Ramp 10.00° C./min to −20.00° C.
Isothermal for 5.00 min
Ramp 10.00° C./min to 250.00° C.
End of method
Data analysis was undertaken using TA instrument Universal Analysis 2000 software (build 4.5.0.5).

The calorimeter head was continuously flushed with dry nitrogen gas at 0.2 L/min during all measurements.

Thermal gravimetry analysis was performed with a PerkinElmer Pyris 1 using aluminium vented pans in ceramic crucibles. The samples were heated at a rate of 10° C/min from 20° C. to 400° C.

Sorption/Desorption Analysis (Dynamic 2.4. Vapour Sorption, DVS)

Vapour sorption experiments were conducted isothermally at 25° C. using a TA instruments Q5000 SA Dynamic Vapour Sorption analyser. Samples of spray dried formulation (~10mg) were subject to initial desorption from ambient to 0% RH, followed by sorption up to 90% RH and subsequent desorption to 0% RH. All step changes were performed in increments of 10% RH and the sample was allowed to equilibrate to a weight change <0.01%/min for a minimum of 5 minutes (and maximum of 240 minutes) at each relative humidity before progressing with the next step. See method specifications summary in table 25 below:

TABLE 25

Sorption/Desorption Analysis method specifications

| Parameter | Conditions |
| --- | --- |
| dm/dt(%) | 0.001 |
| Solvent | Water |
| Experiment temperature | 25° C. |
| Humidity range (% RH) | 0-90-0-90-0 |
| Step increment (% RH) | 10 |
| Number of cycles | 2 |
| Maximum step time | 360 minutes |

ICP-OES

Three samples of Imatinib (1× feed and 2× micronized) were submitted for analysis by ICP-OES for chromium, nickel and iron content using the Thermo Fisher iCap 6500 ICP-OES. The instrument was used in solvent mode, with the Isomist module set at 5° C. The calibration range was 0 to 20 ppm with respect to sample mass. The sample was prepared for analysis by dissolving 50 mg±5 mg in methanol (25 mL); a clear solution was obtained, free from particulates. All system suitability requirements were met (analytical quality control, drift, calibration linearity).

Results

Air-Jet Micronization

A total of 600.00 g of raw Imatinib Free Base material was micronized and 463.38 g were collected from the Micronization of twelve sub-lots. The remaining 66.11 g collected by last two sub-lots micronization was used for the manufacture of Spray-Drying formulations (50:50, 75:25, 90:10) and Carrier-Base Formulation 50 API:50 ML001.

Particle Size Distribution & Specific Surface Area Analysis

The particle size distribution (PSD) analysis of the unmicronized material, micronized material, ten respectively sub-lots, and 463.38 g of API blended together is summarised in Table 26 below.

The micronized 463.38 g of bulk material (Imatinib) had a median particle size of 1.95 μm and 10% undersize of 0.90 μm and 90%-of 4.32 μm. The span of the PSD of the micronized material was 1.75. The 100.1 g of additional material micronized in a second moment had a median of particle size of 1.58 μm and a span of 1.74.

The PSD specifications provided below were been satisfied for all the sub-lots manufactured and for the 450 g of material:

D10: 0.70-0.90 μm

D50: 1.50-2.00 μm

D90: 3.20-4.20 μm

From the 50 g of unmicronized material that was air-jet micronized, an average of 45.92 g of micronized material was collected for each of the ten lots.

TABLE 26

Particle size distribution of unmicronized, micronized Imatinib.

| Dispersing Conditions | $d_{10}/\mu m$ (SDev) | $d_{50}/\mu m$ (SDev) | $d_{90}/\mu m$ (SDev) |
| --- | --- | --- | --- |
| Un-Micronized material (Lot of 1 Kg) | | | |
| 2 bar | 2.38 | 10.42 | 28.68 |
| Micronized material | | | |
| Sub-Lot #1    2 bar | 0.84 | 1.73 | 3.71 |
| Sub-Lot #2    2 bar | 0.85 | 1.77 | 3.72 |
| Sub-Lot #3    2 bar | 0.82 | 1.55 | 3.21 |
| Sub-Lot #4    2 bar | 0.87 | 1.79 | 3.58 |
| Sub-Lot #5    2 bar | 0.87 | 1.74 | 3.73 |
| Sub-Lot #6    2 bar | 0.84 | 1.65 | 3.48 |
| Sub-Lot #7    2 bar | 0.84 | 1.68 | 3.87 |
| Sub-Lot #8    2 bar | 0.85 | 1.70 | 4.33 |
| Sub-Lot #9    2 bar | 0.84 | 1.79 | 4.15 |
| Sub-Lot #10   2 bar | 0.86 | 1.83 | 4.16 |
| Bulk Material 463.38 g    2 bar | 0.90 | 1.95 | 4.32 |
| Sub-Lot #11   2 bar | 0.83 | 1.69 | 3.62 |
| Sub-Lot #12   2 bar | 0.84 | 1.78 | 3.99 |
| Micronized material (100.1 g) | | | |
| Sub-Lot #13   4 bar | 0.69 | 1.63 | 3.53 |
| Sub-Lot #14   4 bar | 0.67 | 1.53 | 3.35 |

The Specif Surface Area Analysis (SSA) was conducted for the unmicronized and the first two micronized sub-lots to ensure a correlation with PSD results shown in table 26.

The unmicronized material had a SSA of 0.88 m²g in line with a median particle size of 10.42 μm. A final analysis by BET was performed at the end for the ten micronized sub-lots blended together (463.38 g) to ensure that the whole bulk lot Specific Surface Area was in line with the singular sub-lots manufactured and reported in table 27 below.

The data show an increased SSA upon micronization of 7.43 m²/g. That was in line with a median particle size reduction of 1.95 μm comparing with the unmicronized material analysed at the beginning.

TABLE 27

Specific surface area (SSA) analyzed by BET of unmicronized and micronized Imatinib.

| Material | SSA (m2/g) | Mean SSA | Std. Dev. (m2/g) |
| --- | --- | --- | --- |
| Un-Micronized | 0.88 0.87 | 0.88 | 0.00 |
| Sub-lot #1 | 8.93 | — | — |
| Sub-lot #2 | 7.96 | — | — |

TABLE 28

Specific surface area (SSA) analyzed by BET of 463.38 g of micronized Imatinib.

| Client Sample ID | Sample ID | Sample Mass (g) | SSA (m2/g) | Mean SSA | St Dev | % RSD | Total Surface (m2) |
|---|---|---|---|---|---|---|---|
| NP-106-004 Post Micronized | 222/043-25A | 0.6134 | 7.2374 | 7.4349 | 0.28 | 3.76 | 4.44 |
| | 222/043-25B | 0.6031 | 7.6323 | | | | 4.60 |

Differential Scanning Calorimetry

The un-micronized sample was analysed on the TGA to determine the decomposition temperature prior to DSC analysis. It was concluded that the sample starts to decompose at approx. 300° C. and therefore the DSC analysis was set for 20-300° C. (FIG. 31).

Figure 31:
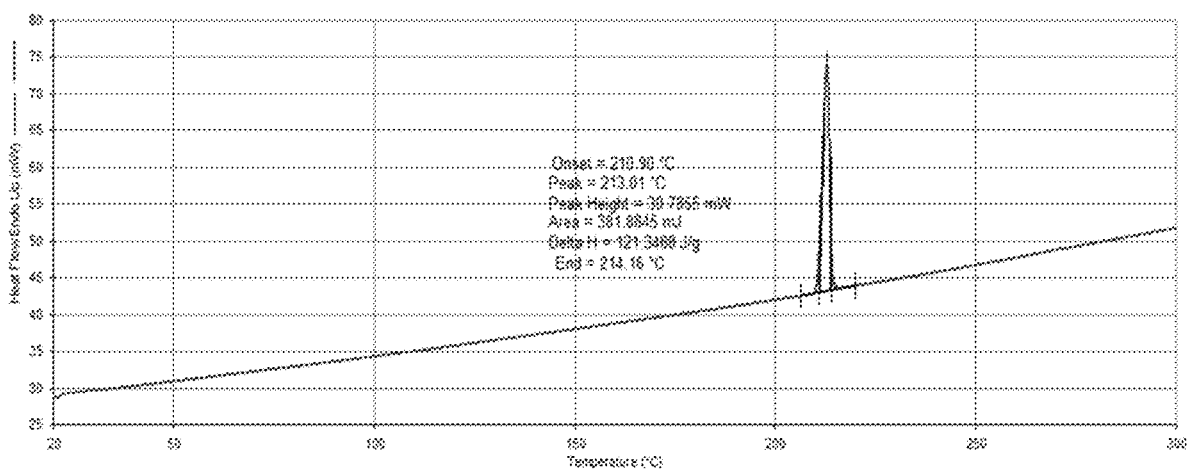
FIG. 31 shows a DSC thermogram of un-micronized material (Lot. 1 Kg) from Example 4.
Figure 32:
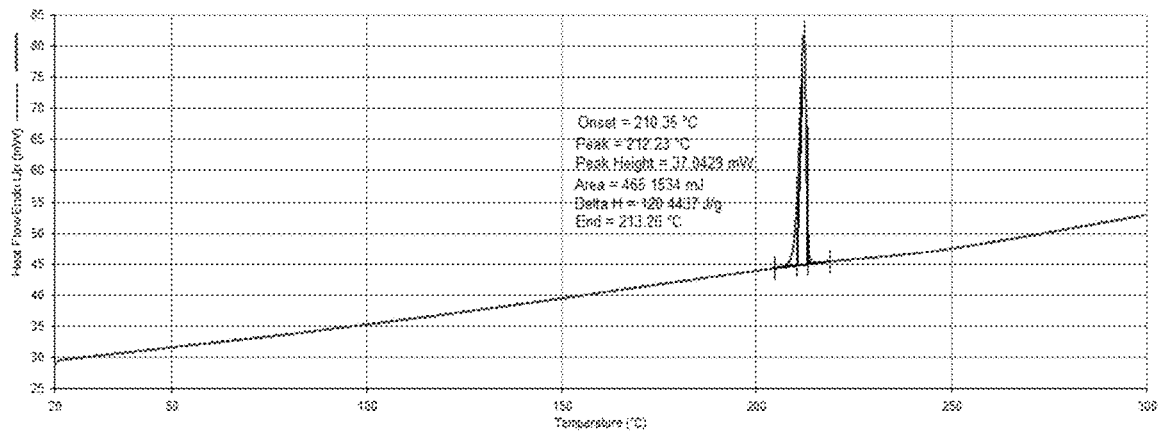
FIG. 32 shows a DSC thermogram of the micronized sub-lot #1 material (50 g) from Example 4.

The DSC thermograms of un-micronized and micronized sub-lot #1 materials and the overlay of their respective thermograms are shown in FIGS. 31-32. DSC of the Free Base suggested a large endothermic event with an onset of ca. 210° C. (peak at ca. 213.01° C. and 212.23° C.) was observed, which was most likely associated with material melting. The imatinib exhibited similar DSC thermograms for both the un-micronized and micronized sub-lot #1 materials with a melt onset of approx. 210° C. and peak enthalpies of approx. 120 J/g.

Figure 33:
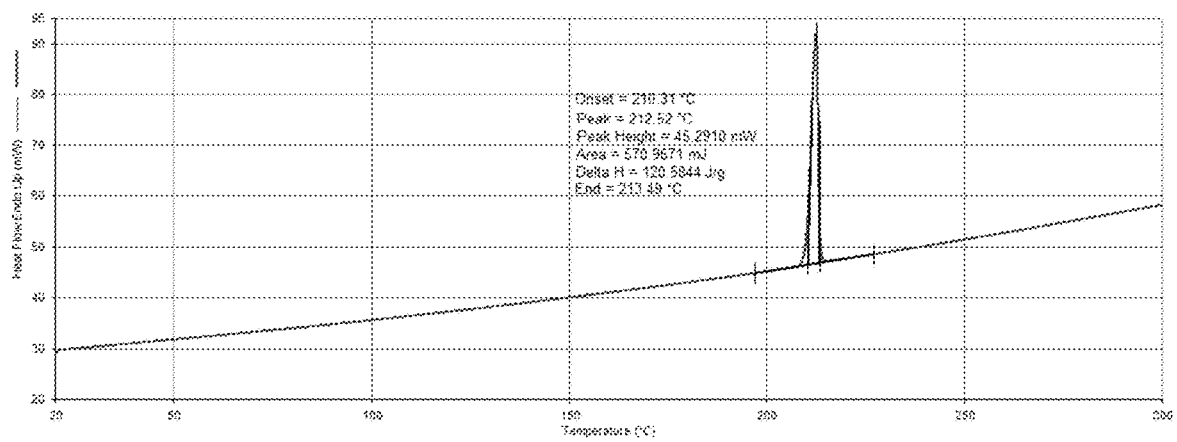
FIG. 33 shows a DSC thermogram of the micronized bulk material (463.38 g) from Example 4.
Figure 34:
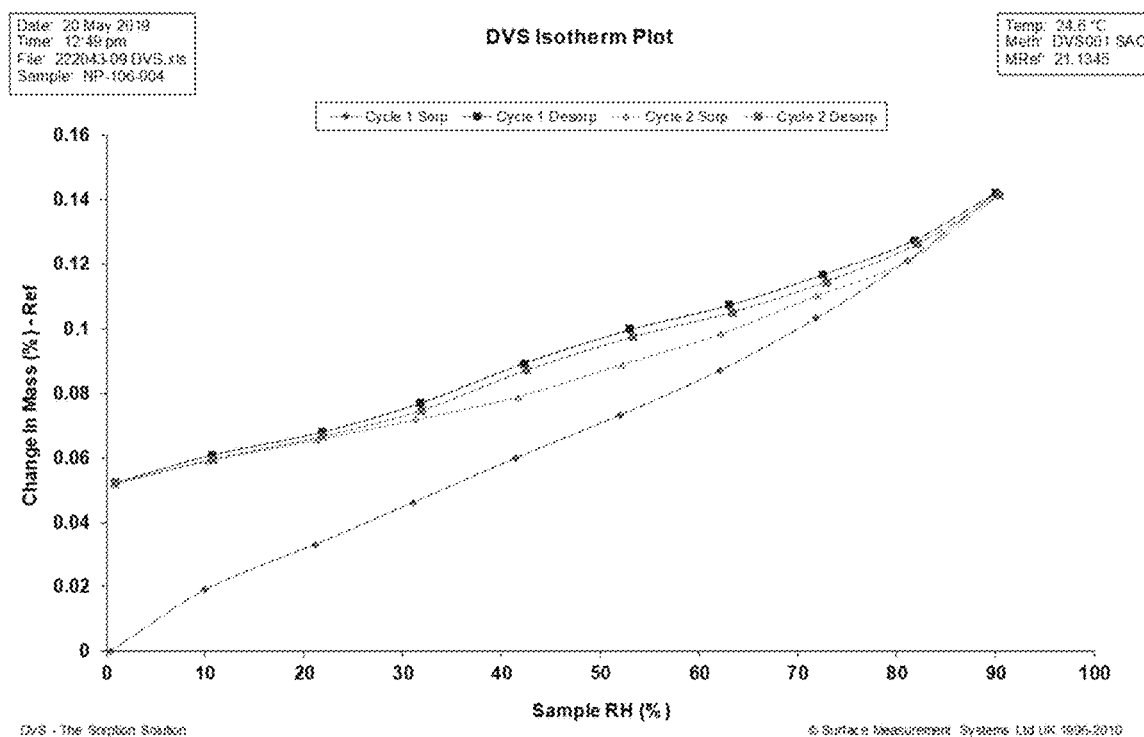
FIG. 34 shows a DVS isotherm plot of the unmicronized Lot. 1 Kg from Example 4.
Figure 35:
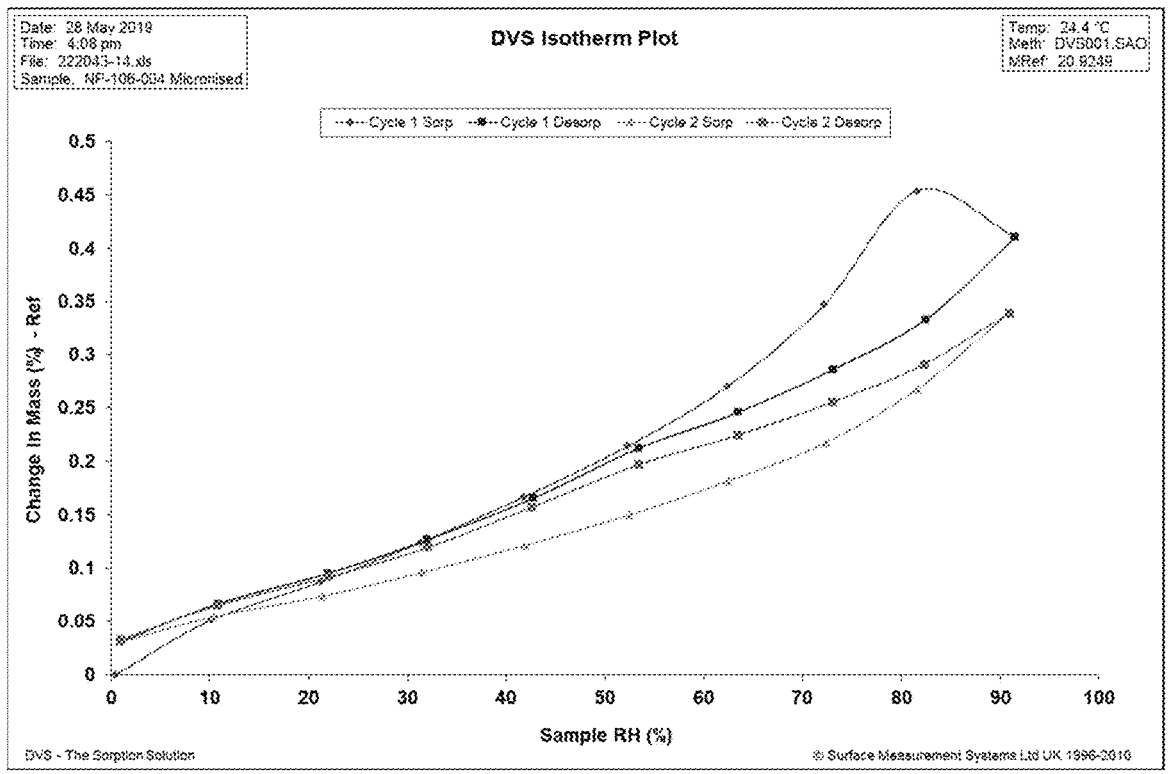
FIG. 35 shows a DVS isotherm plot of the micronized sub-lot #1 material (50 g) from Example 4.
Figure 36:
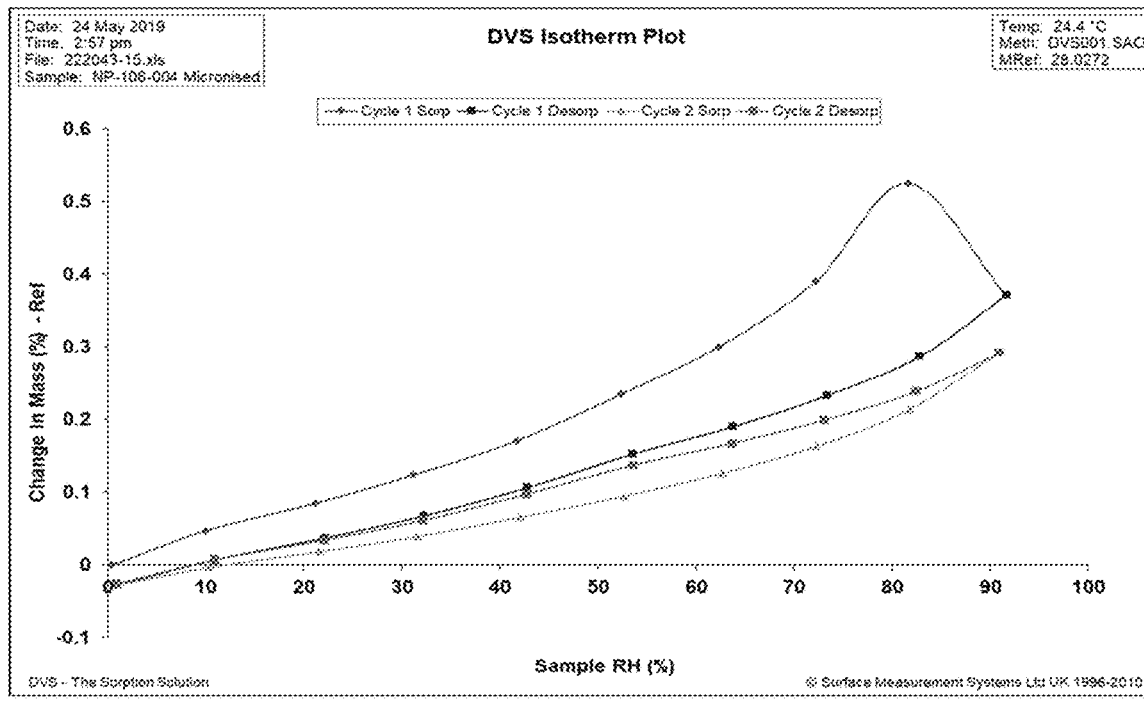
FIG. 36 shows a DVS isotherm plot of the micronized sub-lot #2 material (50 g) from Example 4.
Figure 37:
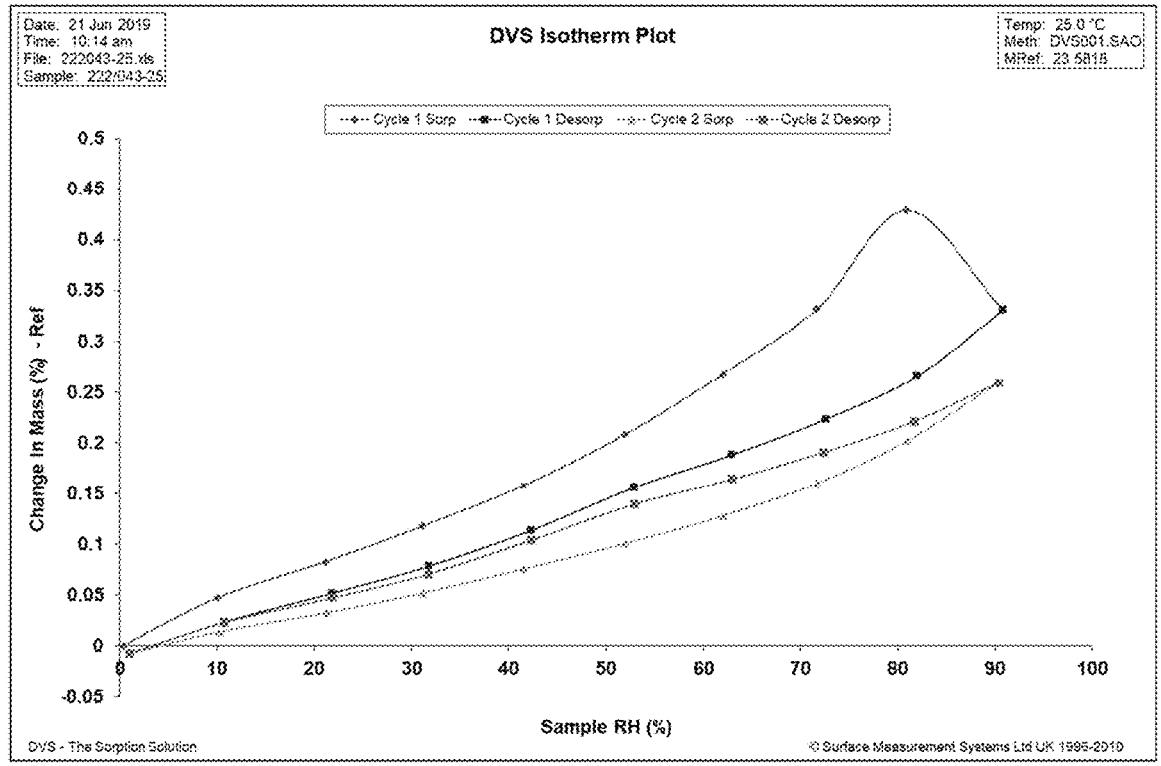
FIG. 37 shows a DVS isotherm plot of the micronized material (463.38 g) from Example 4.

The DSC thermogram for the 463.38 g of material (ten sub-lots blended together) is shown in FIG. 33 with an observed peak at 212.52° C. and peak enthalpy approx. maintained at 120 J/g like the un-micronized and first sub-lot. Sorption/Desorption Analysis (Dynamic Vapour Sorption, DVS) for the various lots is shown in FIGS. 34-37.

X-Ray Powder Diffraction

Figure 38:
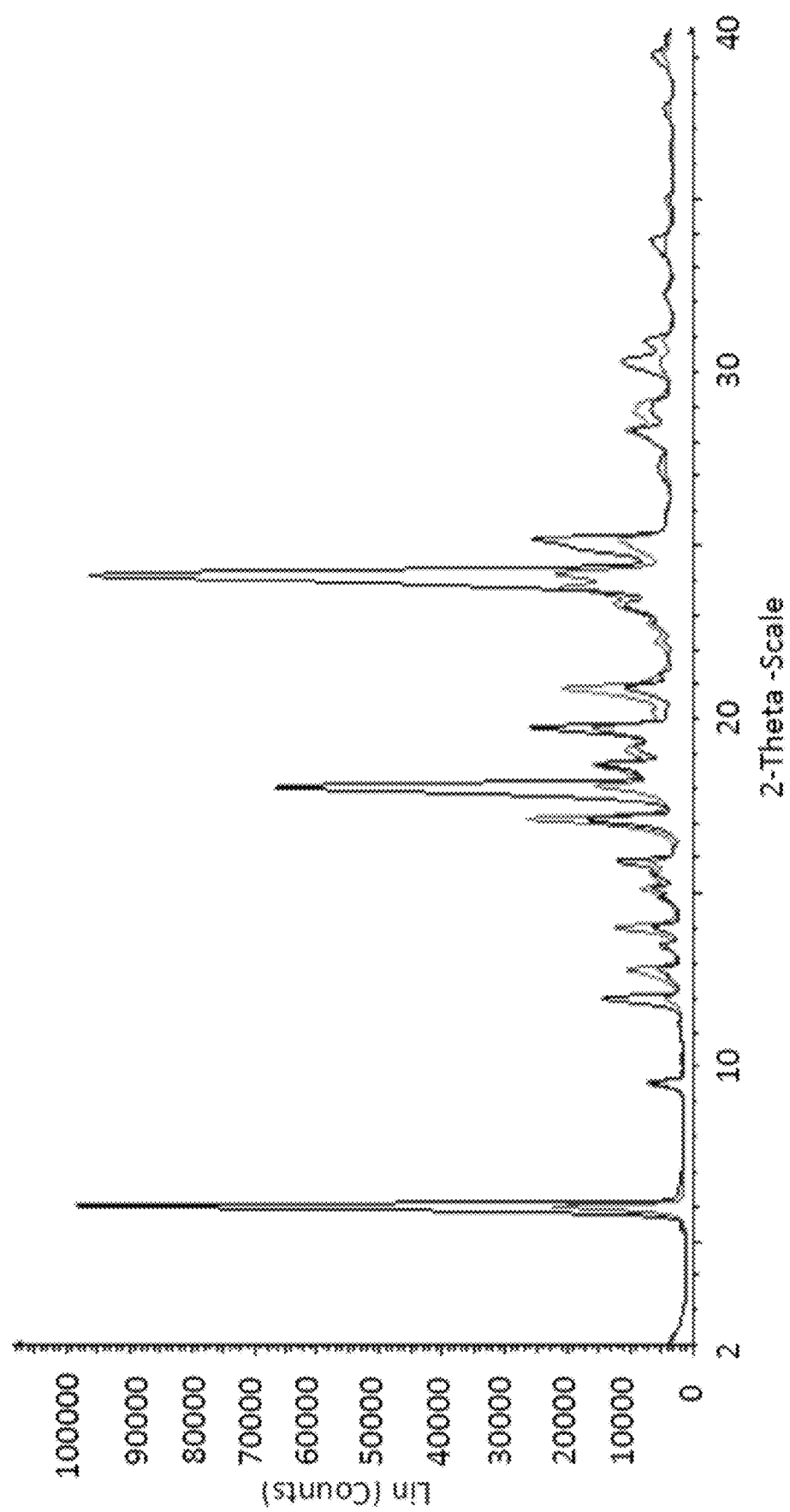
FIG. 38 shows an XRPD overlay of Imatinib Free Base pre and post micronization from Example 4.
Figure 39:
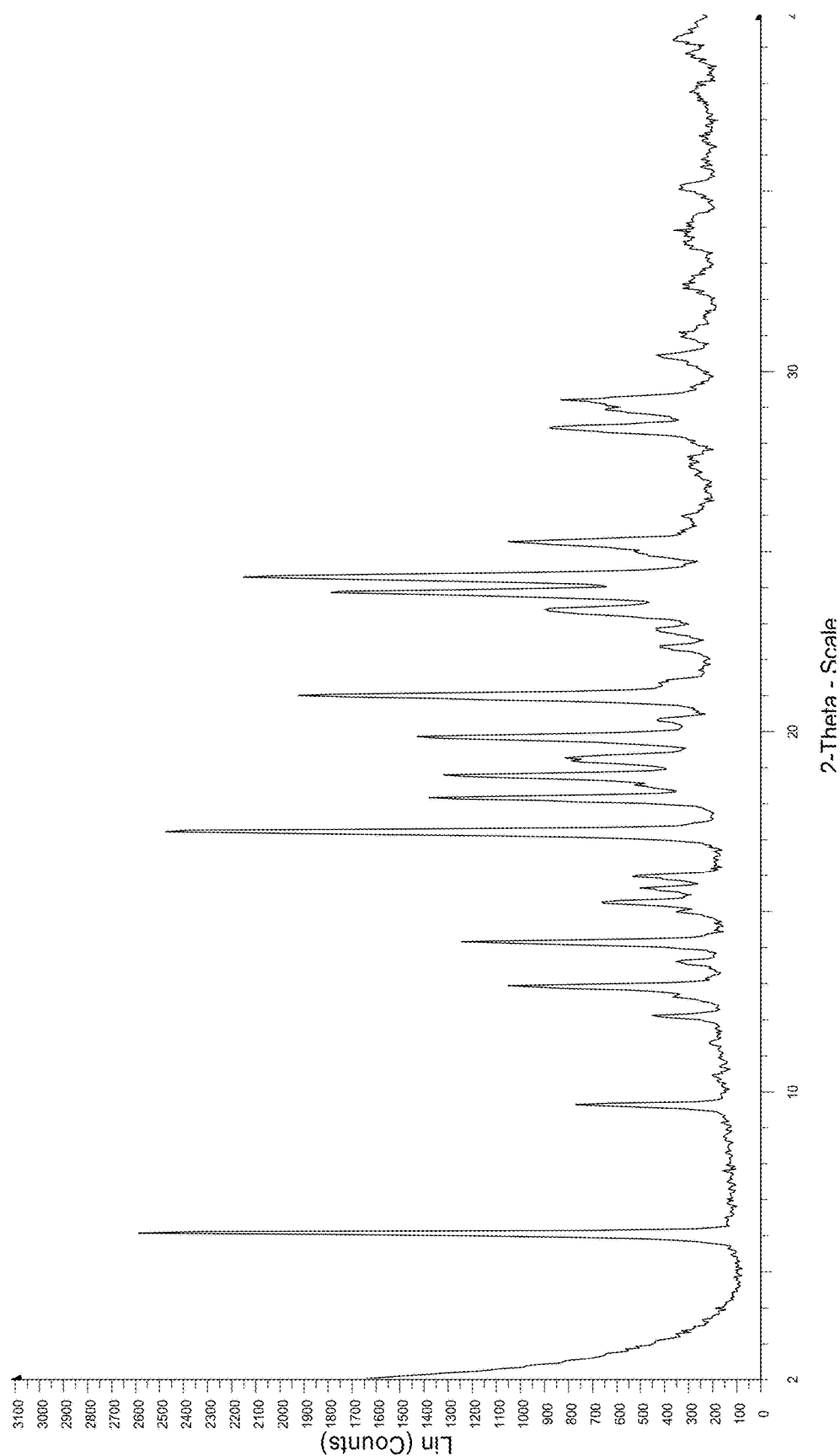
FIG. 39 shows an XRPD isotherm plot of the micronized material (463.38 g) from Example 4.
Figure 40:
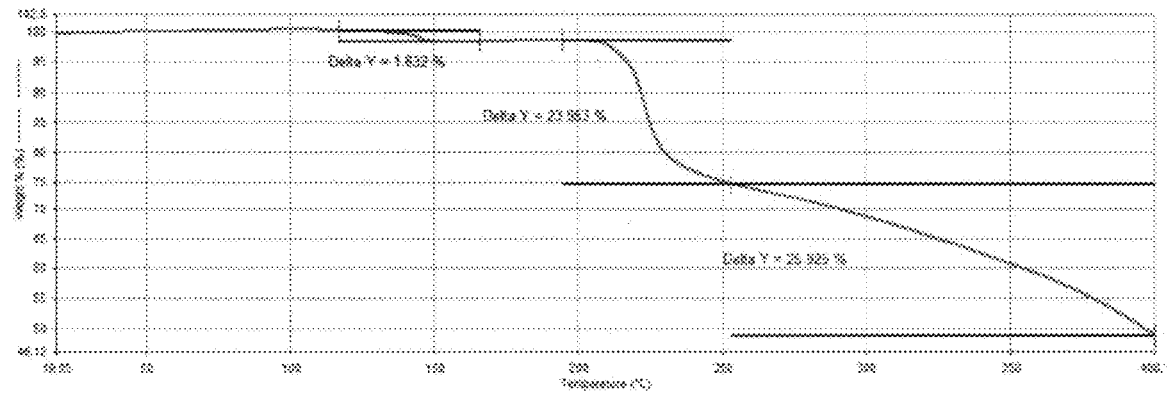
FIG. 40 shows a TGA thermogram of Carrier Based Formulation NP-106-18104-002 from Example 4.
Figure 41:
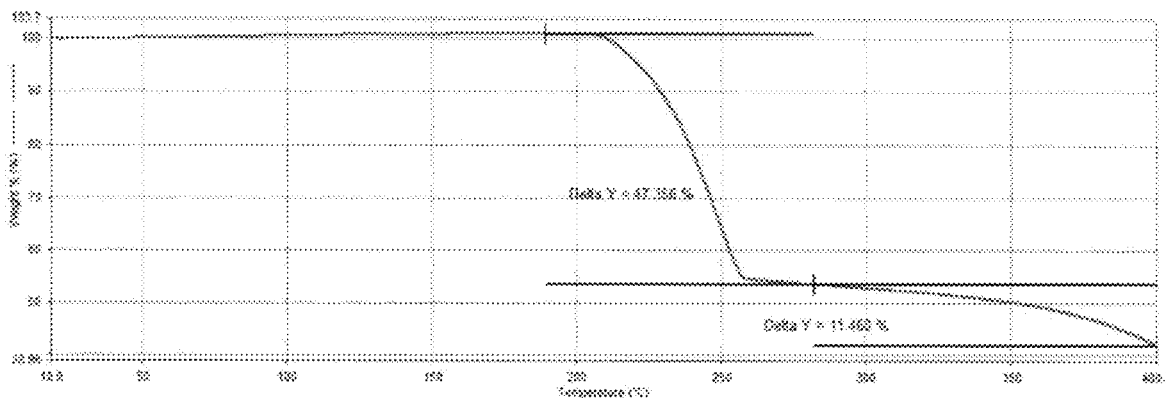
FIG. 41 shows a TGA thermogram of Spray-Dried formulation 119 #008C (50:50 Imatinib: leucine) from Example 4.
Figure 42:
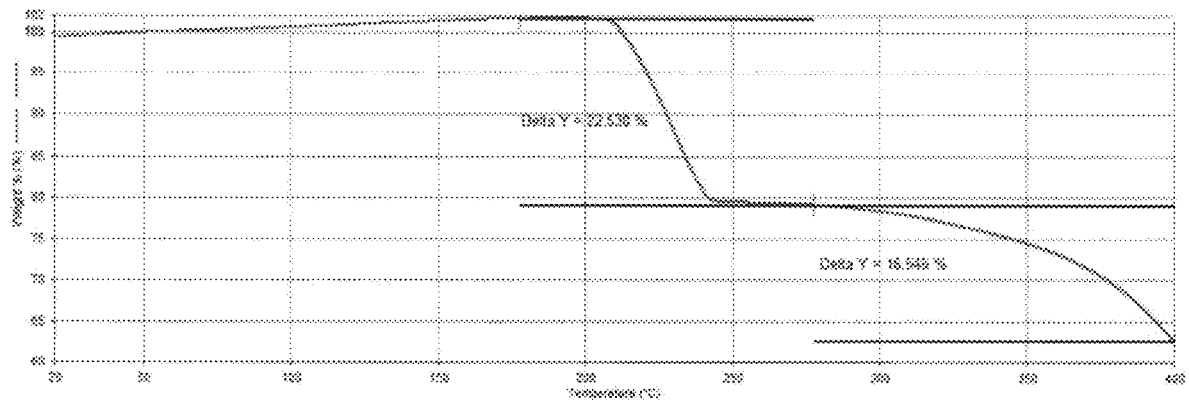
FIG. 42 shows a TGA thermogram of Spray-Dried formulation 119 #008A (75:25 Imatinib: leucine) from Example 4.
Figure 43:
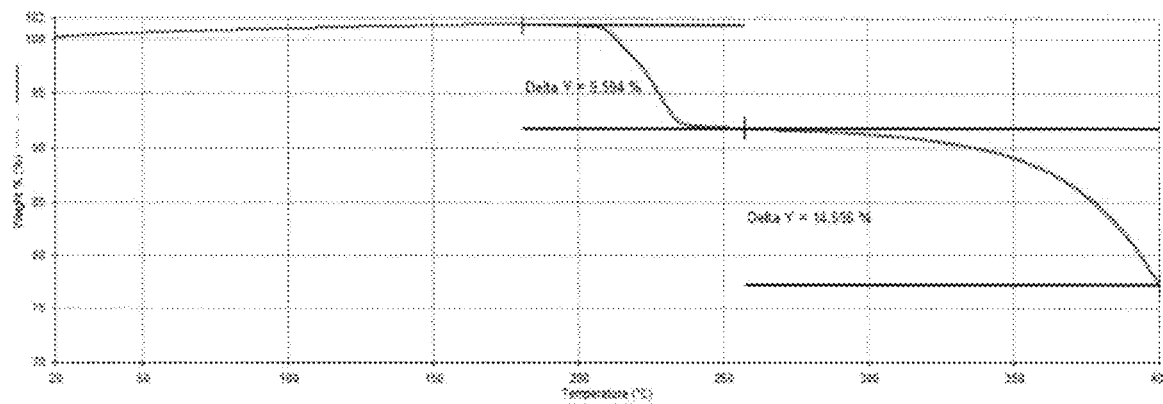
FIG. 43 shows a TGA thermogram of Spray-Dried formulation 119 #008B (90:10 Imatinib: leucine) from Example 4.
Figure 44:
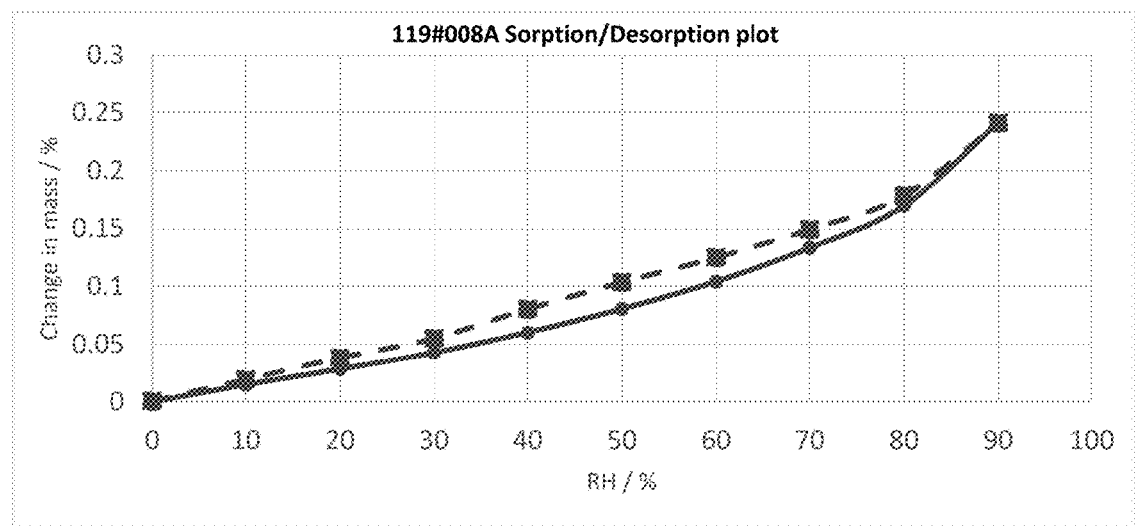
FIG. 44 shows a sorption/desorption trace of batch 119 #008A from Example 4.
Figure 45:
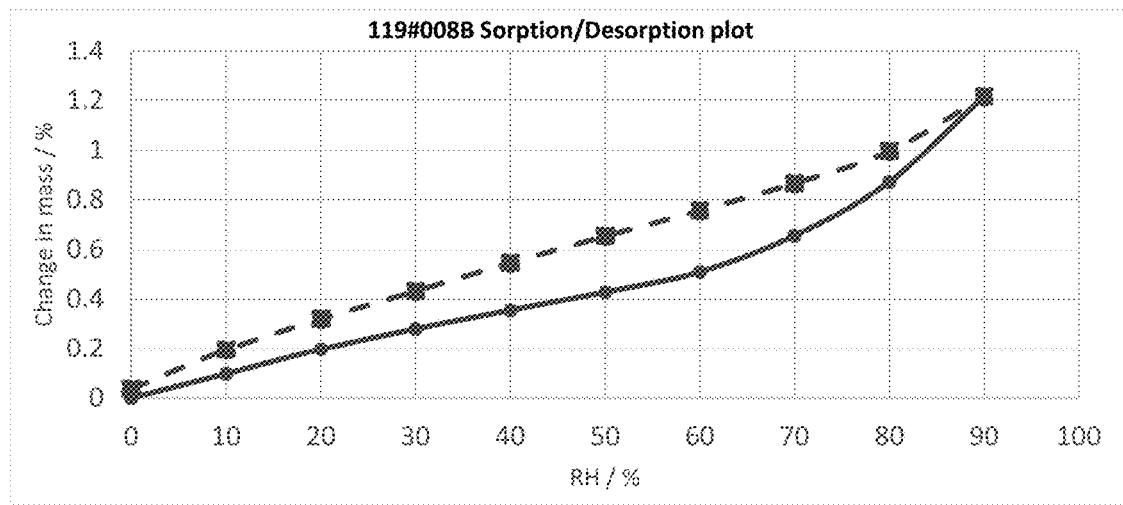
FIG. 45 shows a sorption/desorption trace of batch 119 #008B from Example 4.
Figure 46:
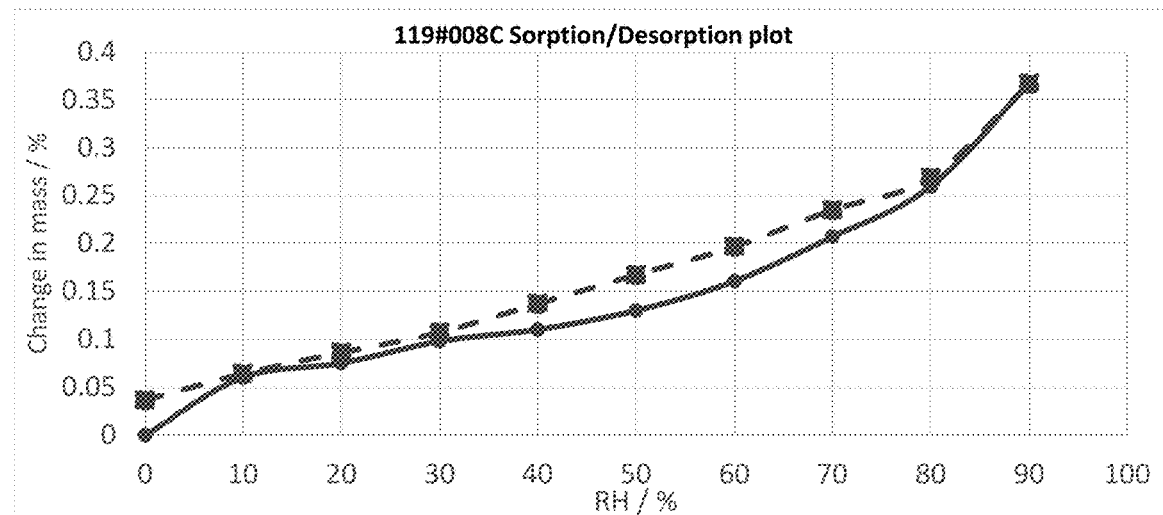
FIG. 46 shows a sorption/desorption trace of batch 119 #008C from Example 4.
Figure 47:
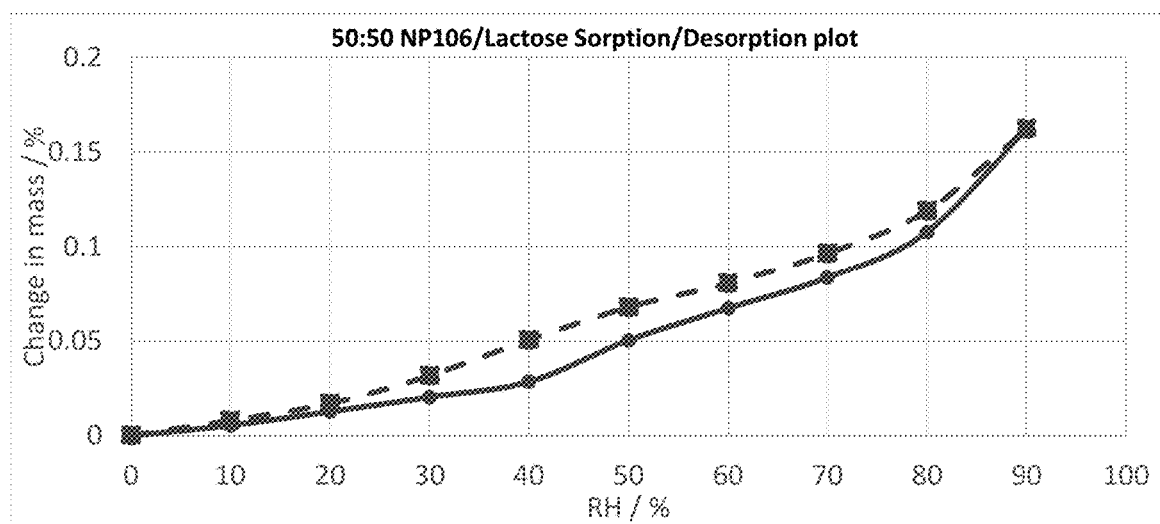
FIG. 47 shows a sorption/desorption trace of batch NP-106-18104-002 from Example 4.

The pre and post micronized material XRPD diffractograms are shown in FIG. 38. Micronized Imatinib exhibited a similar diffraction pattern as observed before micronization. The peak positions remain the same after micronization, but the overall pattern intensity is lower post micronization, and in addition the intensity varied from peak to peak. The peak at 6.0° 2theta and 19° 2theta are significantly more intense for the pre-micronized sample than they are in the micronized sample and peaks at 17° 2theta and 21° 2theta have a higher intensity for the micronized sample than that of the un-micronized sample. The un-micronized sample does show a large, board single peak at 24° 2theta, however, once micronized this peak appears to have split into two, less intense peaks.

ICP-OES

Three samples of Imatinib (1× feed and 2× micronized) were submitted for analysis by ICP-OES for chromium, nickel and iron content using the Thermo Fisher iCap 6500 ICP-OES.

The sample was prepared for analysis by dissolving 50 mg±5 mg in methanol (25 mL); a clear solution was obtained, free from particulates.

All system suitability requirements were met (analytical quality control, drift, calibration linearity).

TABLE 29

ICP-OES results of 463.38 g of micronized Imatinib

| Sample ID | Client Sample ID | Cr Content (ppb w.r.t. sample) | Fe Content (ppb w.r.t. sample) | Ni Content (ppb w.r.t. sample) |
|---|---|---|---|---|
| 222/043-09 | NP-106-004 (NP-106)) (Feed) | ND | ND | ND |
| 222/043-14 | NP-106-004 (NP-106)) (Micronized-Lot 1) | ND | ND | ND |
| 222/043-15 | NP-106-004 (NP-106)) (Micronized-Lot 2) | ND | ND | ND |
| 222/043-25 | NP-106-004 (NP-106)) (Combined 463.38 g) | ND | ND | ND |

Results: Blended Formulation and Suspension Spray-Dryed Formulations

Formulation Performance of High-Payload Carrier Based Formulation Containing Micronized Imatinib Since the feasibility assessment the combination of lactose ML001 for a formulation containing Imatinib with 50% of drug has been evaluated positively, a larger scale of 30 g blend size was formulated. After confirming homogeneity in the formulation by performing BCU, the formulation was characterized with the techniques presented in the methods section. The batch was labelled as NP-106-18104-002.

Formulation Performance of Spray Drying Formulations

The aim of the second part of this study was to evaluate the combination of leucine for a formulation containing Imatinib with 75%, 50% and 90% drug loading. These preparations were manufactured by suspending the micronized Imatinib in an aqueous system with leucine and then spray drying the system.

Three batches of formulation containing varying weight ratios of imatinib: leucine (75:25, 90:10 & 50:50% w/w) were spray dried using a Buchi B290 spray dryer.

Feed solutions were prepared according to the details in Table 30. For each solution, leucine was initially dissolved under stirring into deionised water. Once the leucine had fully dissolved, the micronized imatinib was added to create an opaque white suspension. Addition of the API resulted in some formation of foam. This appeared to be worse in the batches spray dried at higher API concentration (119 #008A/B).

TABLE 30

Overview of Spray Dried formulations

| Batch# | API:Leucine ratio (% w/w) | API mass (g) | Leucine mass (g) | Total mass (g) | Volume of $H_2O$ (mL) | % w/v Solids |
|---|---|---|---|---|---|---|
| 119#008A | 75:25 | 10.50 | 3.50 | 14.00 | 175 | 8 |
| 119#008B | 90:10 | 12.60 | 1.40 | 14.00 | 175 | 8 |
| 119#008C | 50:50 | 6.50 | 6.50 | 13.00 | 325 | 4 |

The feed solutions were spray dried according to the conditions detailed in Table 31. The feed solutions were constantly stirred during spray drying to avoid sedimentation of the suspended API during the run.

TABLE 31

Overview of Spray Dried formulations

| Batch# | Liquid feed rate (g/min) | Inlet Temp. (° C.) | Outlet Temp. (° C.) | Atomisation pressure (bar) | Weight of product (g) | Yield (%) |
|---|---|---|---|---|---|---|
| 119#008A | 2 | 108-112 | 73-76 | 4 | 10.75 | 76.8 |
| 119#008B | 2 | 112-114 | 73-75 | 4 | 10.80 | 77.1 |
| 119#008C | 2 | 110-114 | 73-75 | 4 | 9.58 | 73.7 |

All three batches of formulation were successfully manufactured to produce fine white powders which were collected in similar yield from the collection pot. Losses appeared largely due to deposit of material on the walls of the spray chamber, whilst it's likely there was also some loss of fine particles to the filter due to the high atomisation pressure used for each spray.

After processing it was noted that each of the feed solutions left a foam residue within the feed vessel they were sprayed from. This may also have contributed to loss of yield.

Particle Size & Specific Surface Area Analysis of Spray Dried Formulations and Carrier Based DPI Formulation Table 32 reports the particle size of the spray dried formulations. All three formulations had particle size suitable for pulmonary delivery. Particle size also appeared to slightly increase with increasing leucine content. The carrier-based formulation, batch NP-106-18104-002, (50:50 API: lactose) was smaller than the spray dried formulations.

Table 33 below shows the specific surface area results analysed by BET according to the method described in the methods section above. The surface area of the 90:10, 75:25 and 50:50 preparation was 9.6, 14.0 and 22.0 m²/g, respectively. These data interestingly highlight that decreasing concentration of leucine resulted in higher surface area of the spray-dried particles. This may be due to the formation of surface corrugations at lower leucine concentrations.

TABLE 32

PSD results of Spray Dried formulations

| Batch # | API:Leucine ratio (% w/w) | $d_{10}$ (µm) | $d_{50}$ (µm) | $d_{90}$ (µm) | VMD (µm) |
|---|---|---|---|---|---|
| 119#008C | 50:50 | 0.79 | 2.49 | 5.69 | 2.98 |
| 119#008A | 75:25 | 0.59 | 2.13 | 4.27 | 2.36 |
| 119#008B | 90:10 | 0.47 | 1.90 | 3.60 | 2.01 |
| NP-106-18104-002 | 50:50 | 0.39 | 1.48 | 3.54 | 1.79 |

TABLE 33

Specific surface area (SSA) analyzed by BET of unmicronized and micronized Imatinib.

| Batch # | API:Leucine ratio (% w/w) | Sample Mass (g) | SSA (m²/g) | Mean SSA (m²/g) | Std. Dev | % RSD | Tot. Surface (m²) |
|---|---|---|---|---|---|---|---|
| 119#008C | 50:50 | 0.3545 | 21.9505 | 21.9085 | 0.06 | 0.27 | 7.78 |
|  |  | 0.3472 | 21.8665 |  |  |  | 7.59 |
| 119#008A | 75:25 | 0.3493 | 13.8895 | 13.9704 | 0.11 | 0.82 | 4.85 |
|  |  | 0.3406 | 14.0512 |  |  |  | 4.79 |
| 119#008B | 90:10 | 0.3670 | 9.6732 | 9.5914 | 0.12 | 1.21 | 3.55 |
|  |  | 0.3444 | 9.5095 |  |  |  | 3.28 |
| NP-106-18104-002 | 50:50 | 0.3605 | 3.4106 | 3.4148 | 0.01 | 0.17 | 1.23 |
|  |  | 0.3581 | 3.4189 |  |  |  | 1.22 |

DSC Analysis of Spray Dried Formulations and Carrier Based DPI Formulation

The four samples were analysed by DSC according to the method described in methods section.

For batches 119 #008A-C, the first heating cycle displayed an event at ~210-211° C. which was related to the melting of imatinib. The temperature at which the melt occurred appeared to decrease very slightly with increasing leucine content. The second heating cycle displayed a glass transition for each of the formulations at a temperature of ~70-80° C. This was a result of the API within the formulations being quench cooled during the cooling phase of the DSC method.

For NP-106-18104-002, the first heating cycle displayed two key endothermic events. The first at ~149° C. possibly related to the dehydration of lactose whilst a second, broader event at ~208° C. was probably a result of the melting of both lactose and imatinib. There was possibly a very weak Tg observed at ~101° C. exhibited in the second heating cycle, although it was difficult to discern from the baseline.

DSC Analysis of Leucine and NP-106 Micronized Imatinib

The leucine showed a very weak endothermic event on both cycle 1 and 2 at ~76° C. The micronized API showed a melt on cycle 1 at 212° C. and a weak glass transition in cycle 2 at 78° C., similar to what was observed in the spray dried formulations.

Thermal Gravimetric Analysis for Carrier Based DPI Formulation and Spray Dried Formulations The thermal gravimetry analysis (TGA) of the carrier-based and spray dried formulations (FIGS. 40-43) showed a melt at approximately 210° C. for all formulations and decompositions occurring beyond 250° C.

The carrier-based formulation shows a TGA around 120-150° C., which is related to the presence of lactose in this formulation preparation.

DVS Analysis of Spray Dried Formulations and Carrier Based DPI formulation

Sorption/desorption (DVS) analysis was performed on spray dried formulations and carrier-based formulation. Traces for batches 119 #008A/B/C and NP-106-104-002 are shown in FIGS. 44-47, respectively.

The spray dried formulations generally had very low hygroscopicity. Batch 119 #008A (75:25 imatinib: leucine) took on a maximum of 0.24% moisture at 90% RH during the sorption phase of the analysis, whilst 119 #008B (90:10 imatinib: leucine) took on 1.22% moisture and 119 #008C (50:50 API: leucine) took on 0.37% moisture. When the RH was reduced back to 0% RH, the formulations released virtually all the moisture they had previously taken up.

Small artefacts can be seen in the % weight change trace for batches 119 #008A and 119 #008C. These may be due to vibrations in the surrounding area of the instrument and appear exaggerated due to the small scale of each trace.

XRPD Analysis of Spray Dried Formulations

Figure 48:
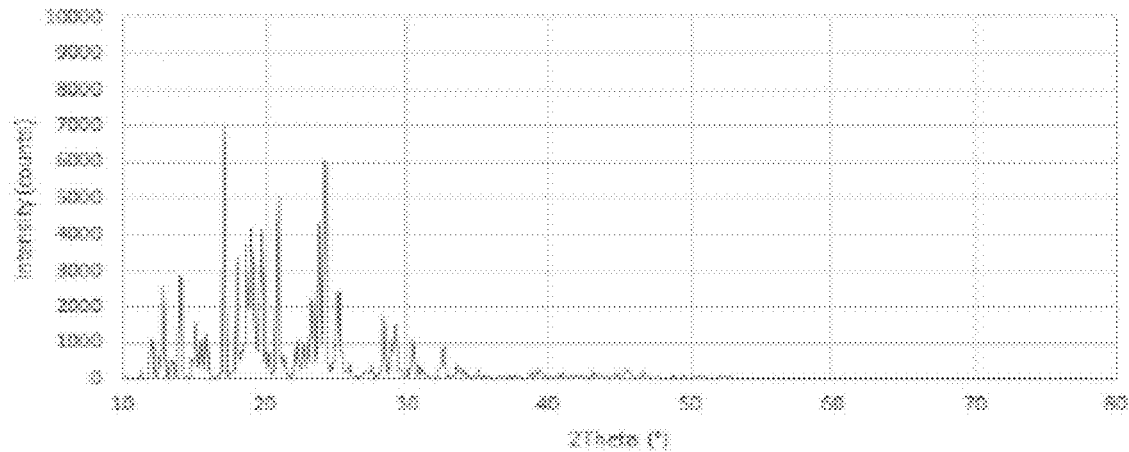
FIG. 48 shows a background subtracted XRPD trace of batch 119 #008A from Example 4.
Figure 49:
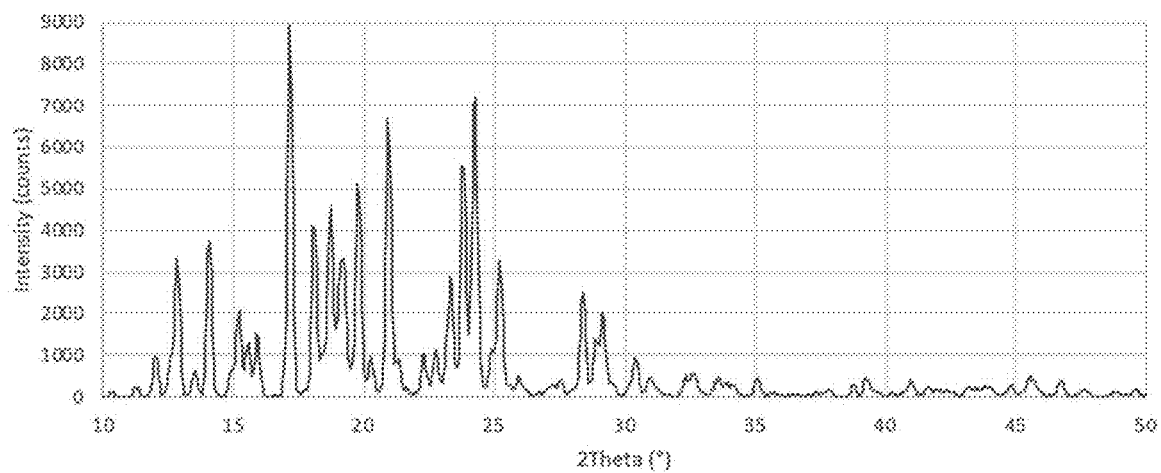
FIG. 49 shows a background subtracted XRPD trace of batch 119 #008B from Example 4.
Figure 50:
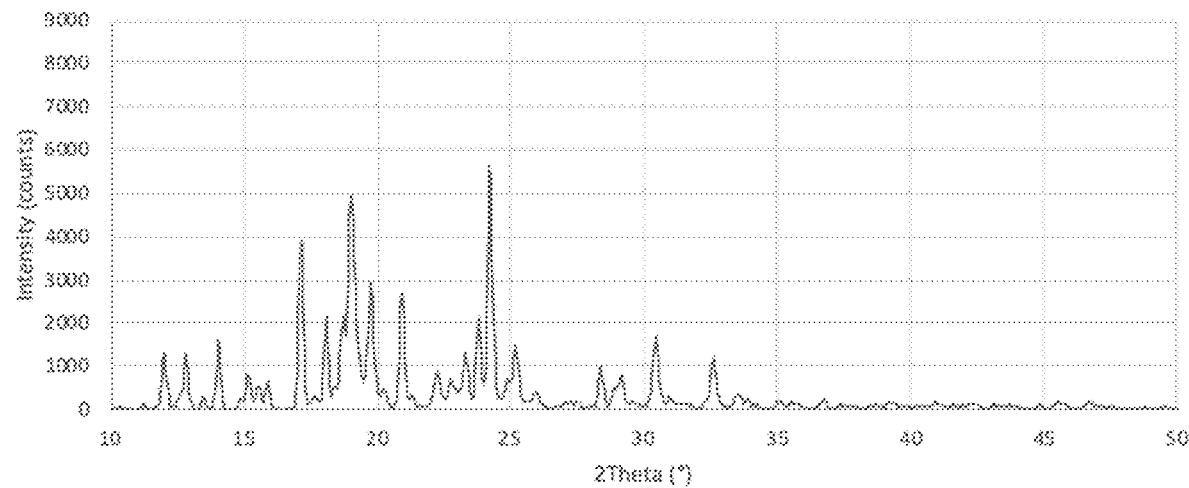
FIG. 50 shows a background subtracted XRPD trace of batch 119 #008C from Example 4.
Figure 51:
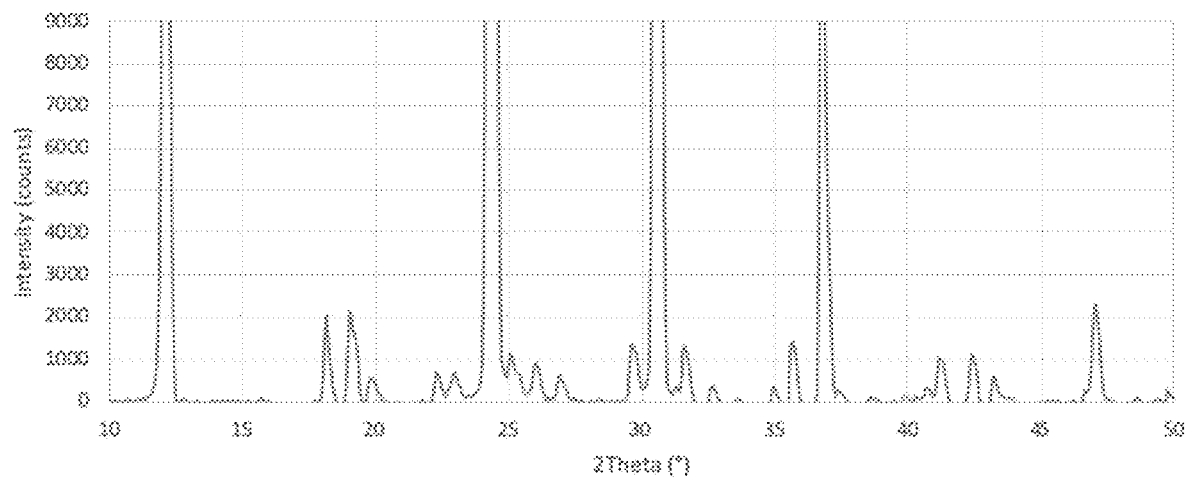
FIG. 51 shows a background trace of Leucine.
Figure 52:
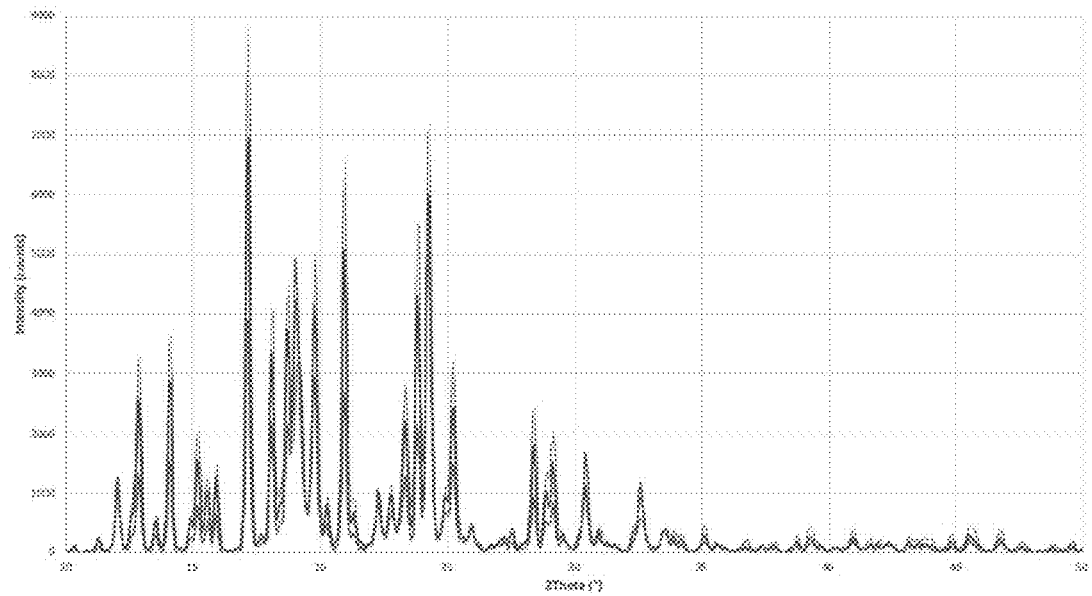
FIG. 52 shows overlaid, background subtracted, XRPD traces of batches 119 #008A, B and C from Example 4.

XRPD analysis was performed on the spray dried formulations according to the method described in the method section above. The background subtracted traces for 119 #008A/B/C can be seen in FIGS. 48, 49, and 50 respectively. All three formulations appeared to be largely crystalline and an overlay of these XRD traces can be seen in FIG. 52. The subtracted background, which would be the trace for the leucine material can be seen in FIG. 51.

Figure 53:
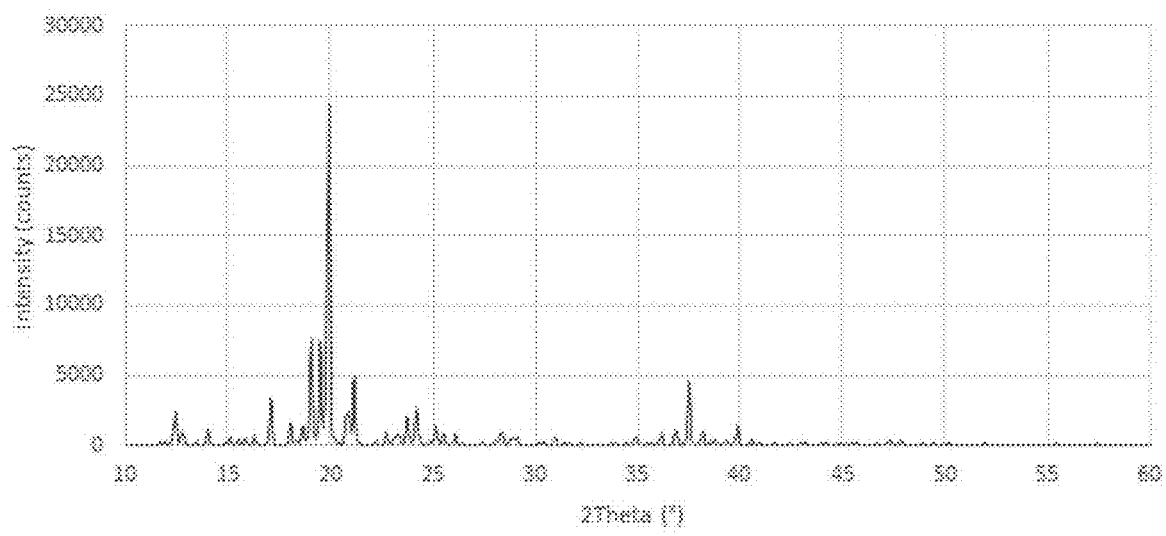
FIG. 53 shows a background subtracted XRPD trace of batch NP-106-18104-002 from Example 4.
Figure 54:
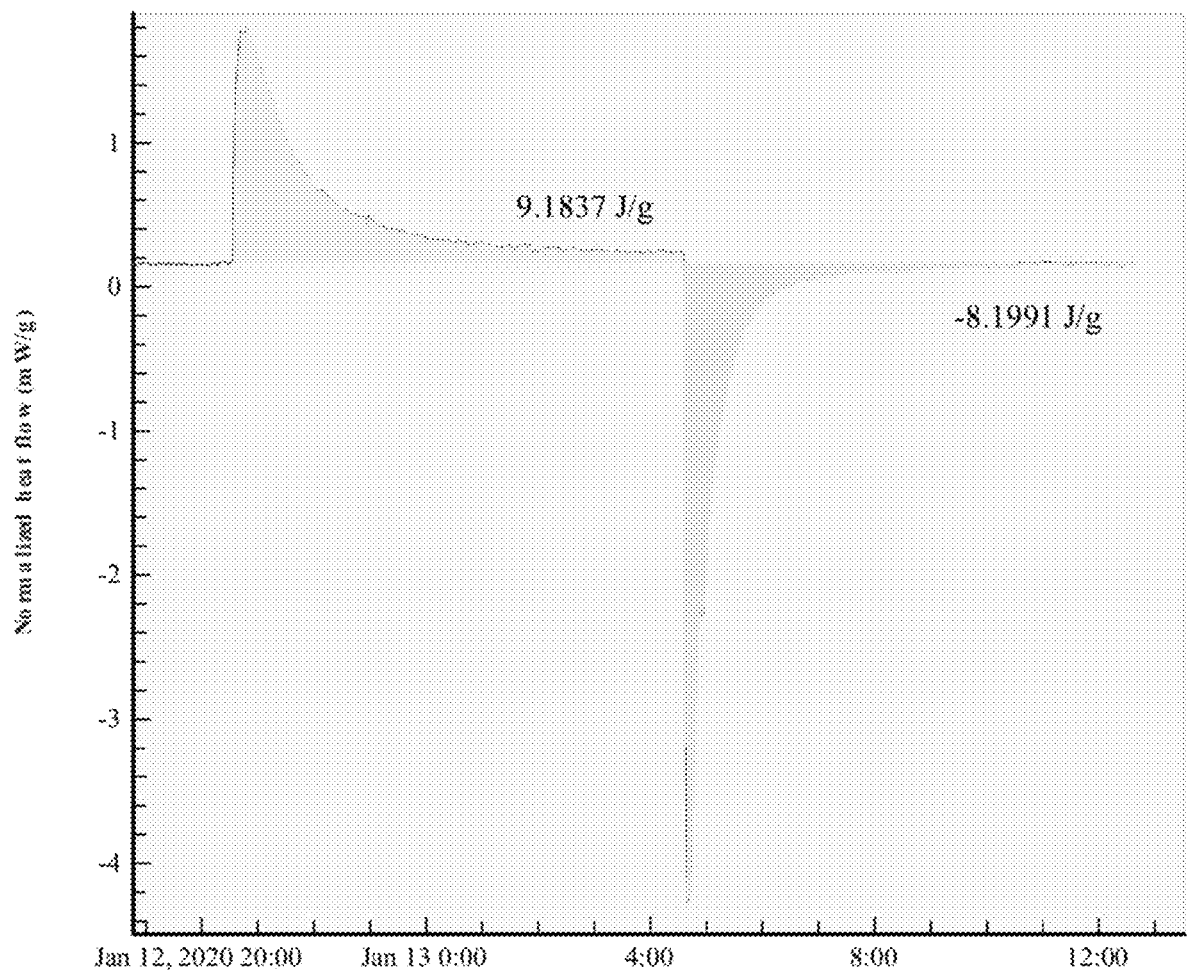
FIG. 54 shows adsorption & desorption for batch NP-106-18104-002 from Example 4.
Figure 55:
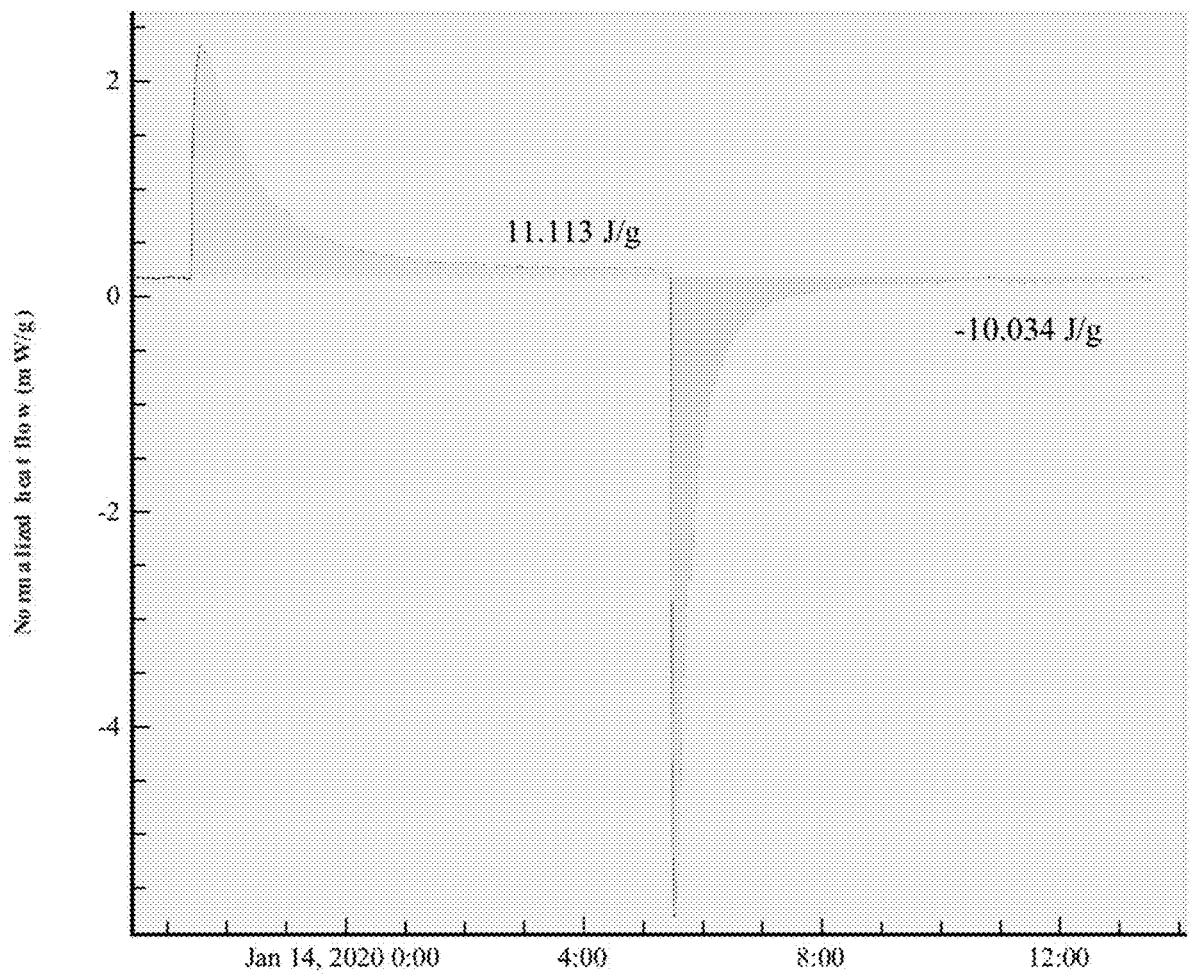
FIG. 55 shows adsorption & desorption for a 50:50 API:Leucine spray-dried formulation from Example 4.
Figure 56:
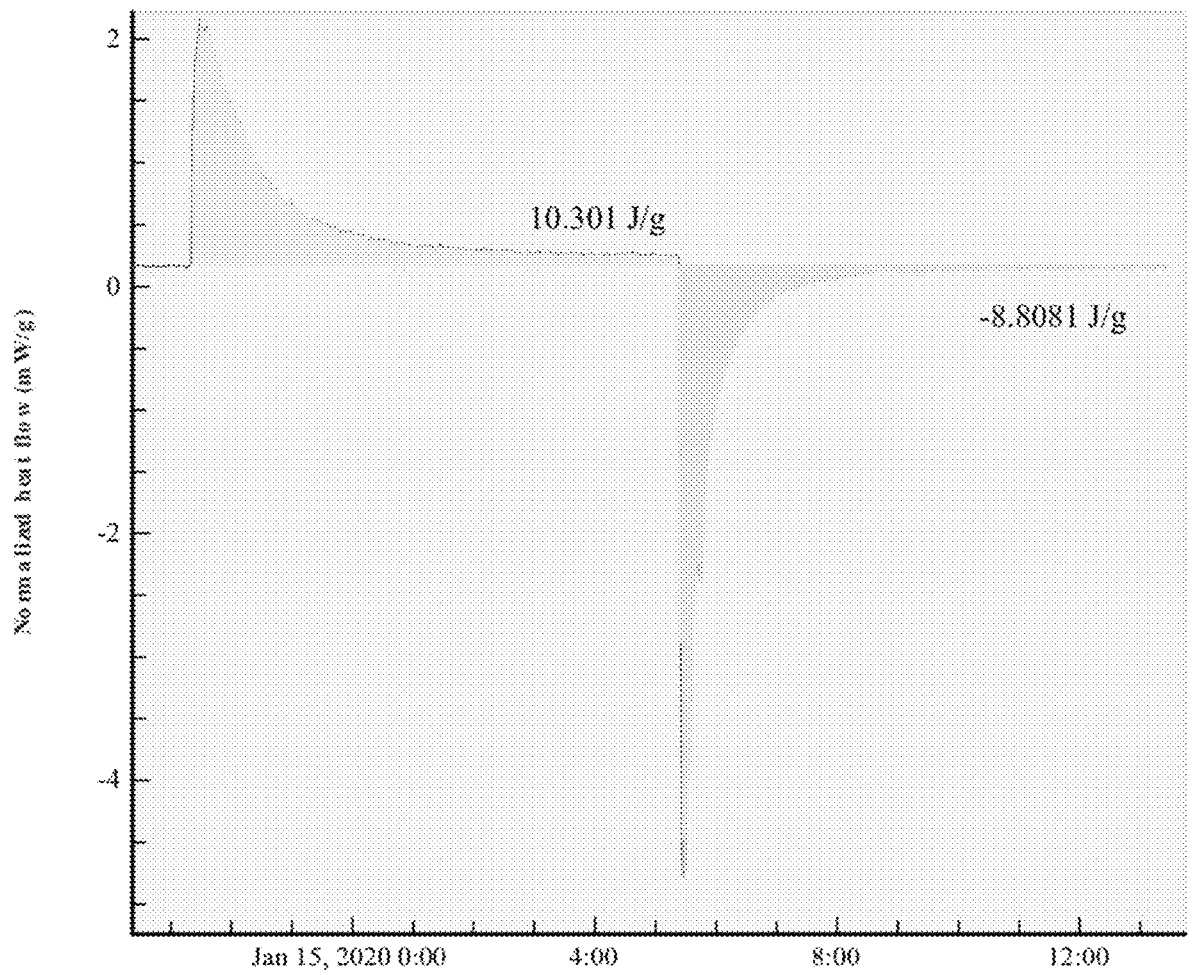
FIG. 56 shows adsorption & desorption for a 75:25 API:Leucine spray-dried formulation from Example 4.
Figure 57:
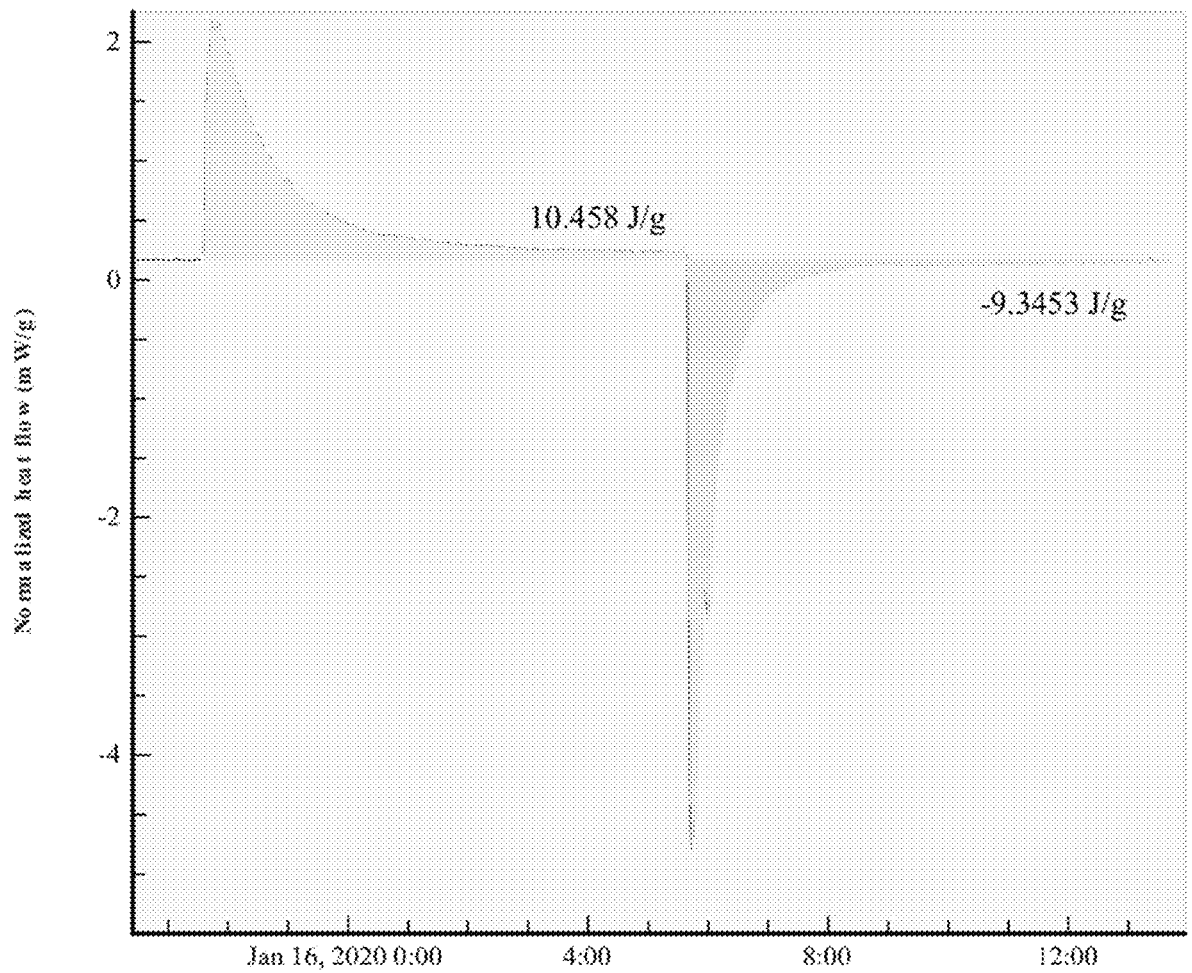
FIG. 57 shows adsorption & desorption for a 90:10 API:Leucine spray-dried formulation from Example 4.

The background subtracted traces for NP-106-18104-002 can be seen in FIG. 53.

Isothermal Perfusion Calorimetry Performed by TAM (Thermal Activity Monitor)

TAM analysis was performed all drug substance material. Analysis was conducted for 6 hours at 0% RH and for 8 hrs at 90% RH. The system was brought back down to 0% RH for a final 8 hours. The wetting (adsorption) and drying (desorption) thermogram over time are shown in FIGS. 54-57 for the micronized, spray-dried 50:50, 75:25 and 90:10 with leucine.

The area under the curve (AUC) of the wetting peak is representative of the enthalpy of re-crystallisation. The AUC of the wetting peak for the micronized, spray-dried 50:50, 75:25 and 90:10 with leucine ranged from 9.2-11.1 J/g. These data suggested that the amorphous content of all system was similar. Further work using this method is advised with unmicronized material to determine the amount of amorphicity in these systems. Our current understanding is that the amorphous content is below the limit of quantification.

Relative Substances by High Performance Liquid Chromatography

In further analysis through High Performance Liquid Chromatography (HPLC), no relative substance was detected and otherwise quantified for Spray Drying formulations and Carrier Based DPI Formulation, NP-106-18104-002.

Results: Time 1 Month at 40° C./75% RH and 25° C./60% RH

Figure 58:
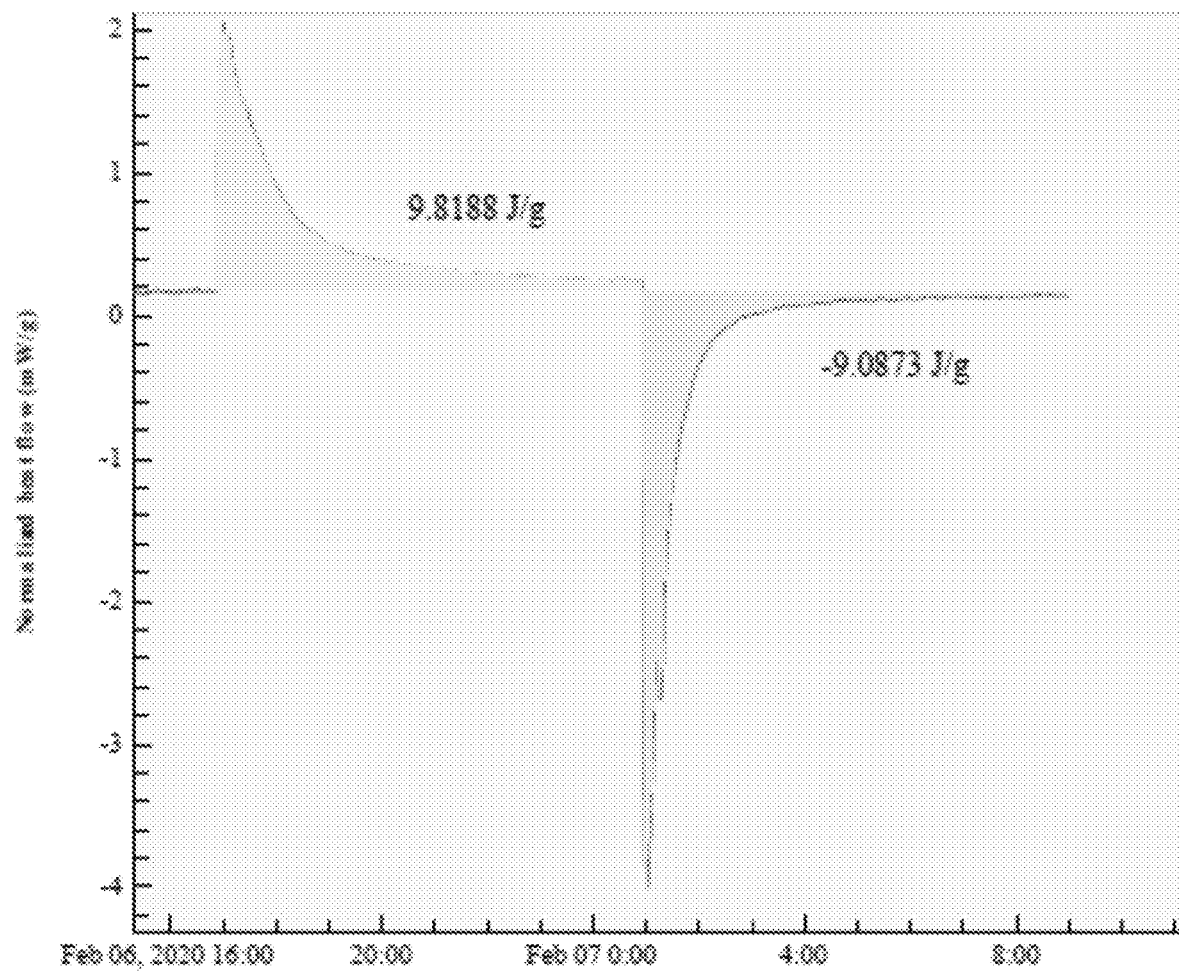
FIG. 58 shows adsorption & desorption for NP-106-104-M2 after one month of conditioning at 25° C./60% RH from Example 4.
Figure 59:
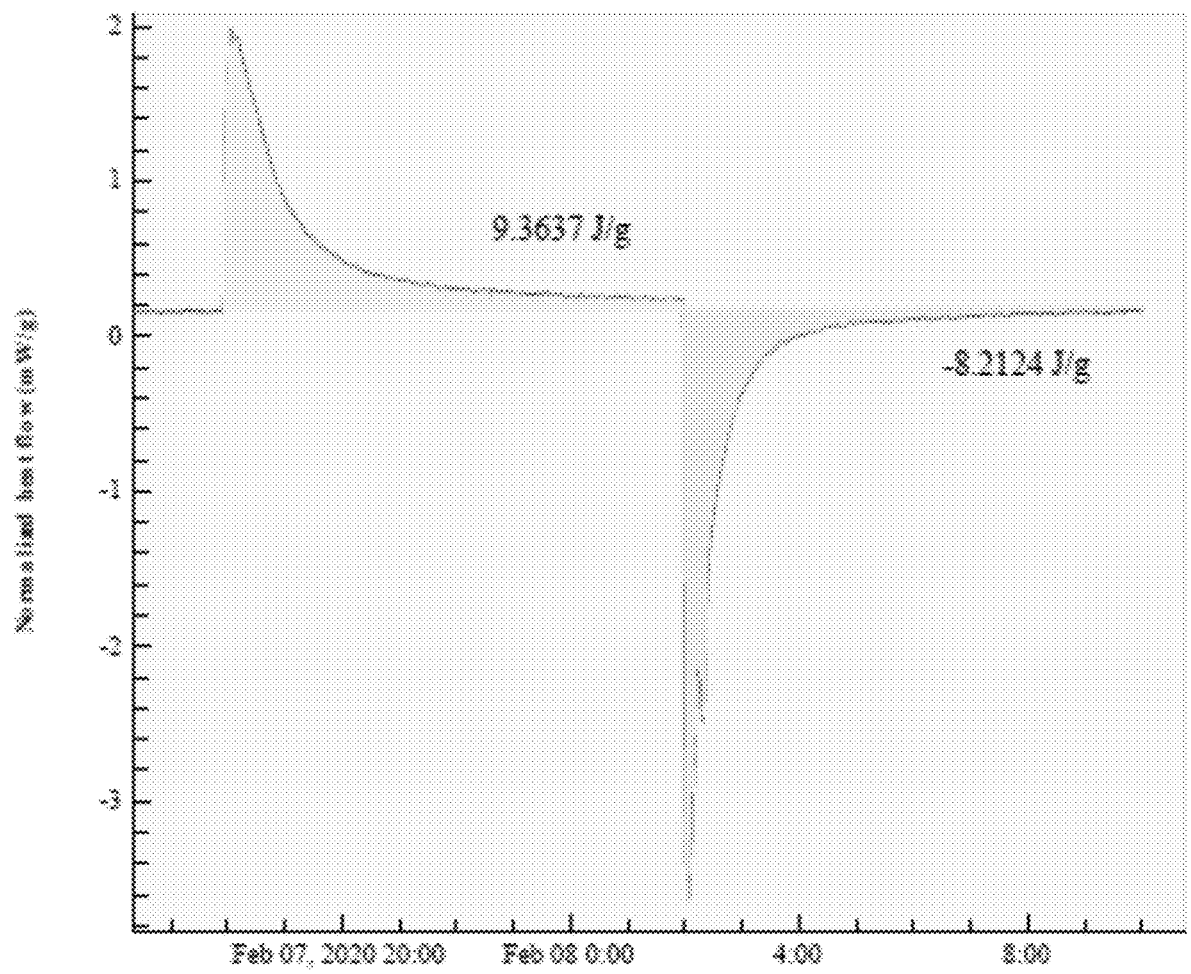
FIG. 59 shows adsorption & desorption for NP-106-104-M2 after one month of conditioning at 40° C./75% RH from Example 4.
Figure 60:
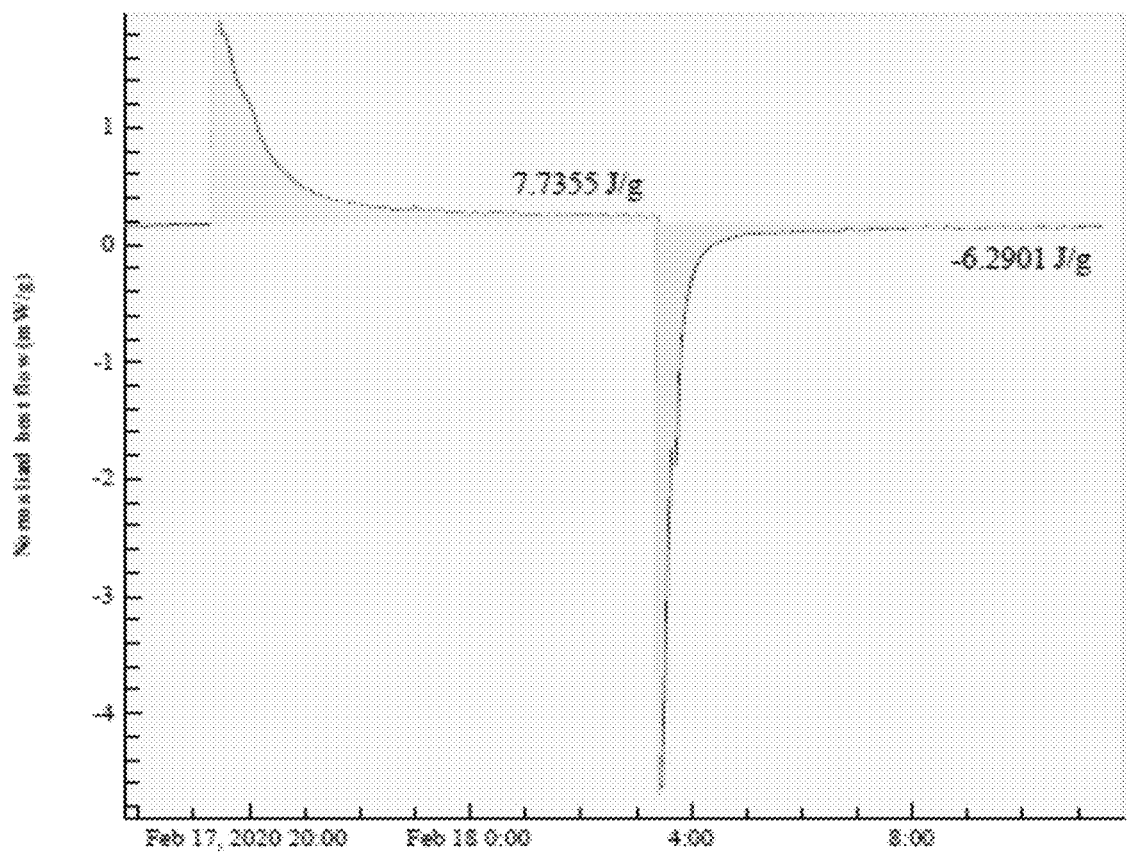
FIG. 60 shows adsorption & desorption for 119 #008A (75:25) after one month of conditioning at 25° C./60% RH from Example 4.
Figure 61:
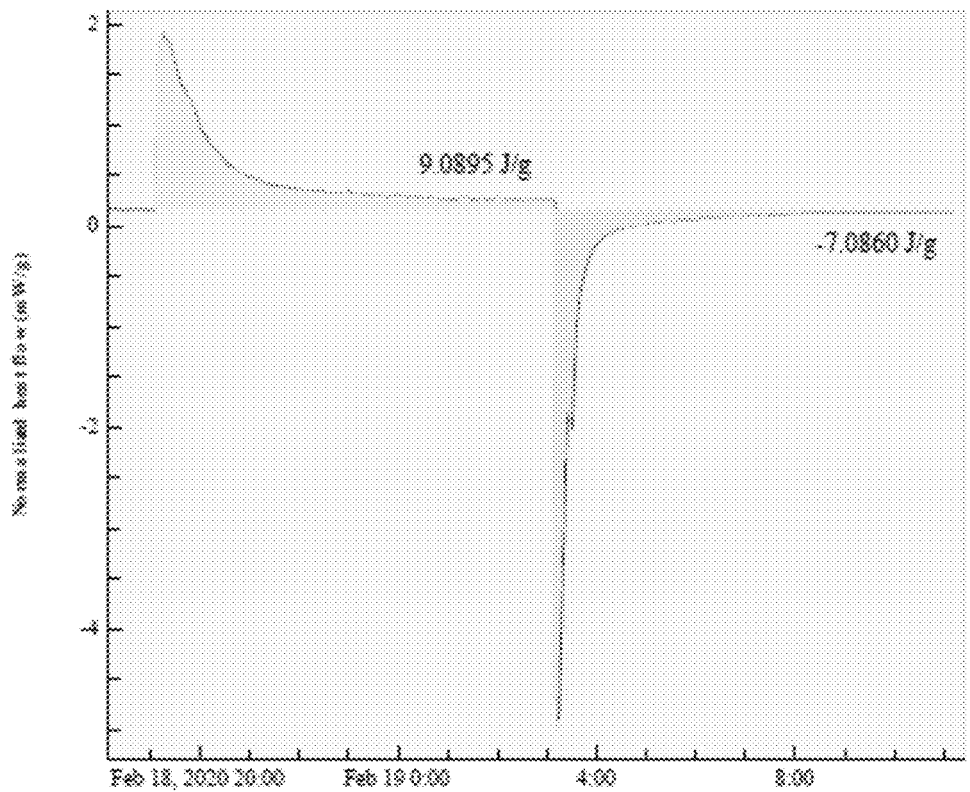
FIG. 61 shows adsorption & desorption for 119 #008B (90:10) after one month of conditioning at 25° C./60% RH from Example 4.
Figure 62:
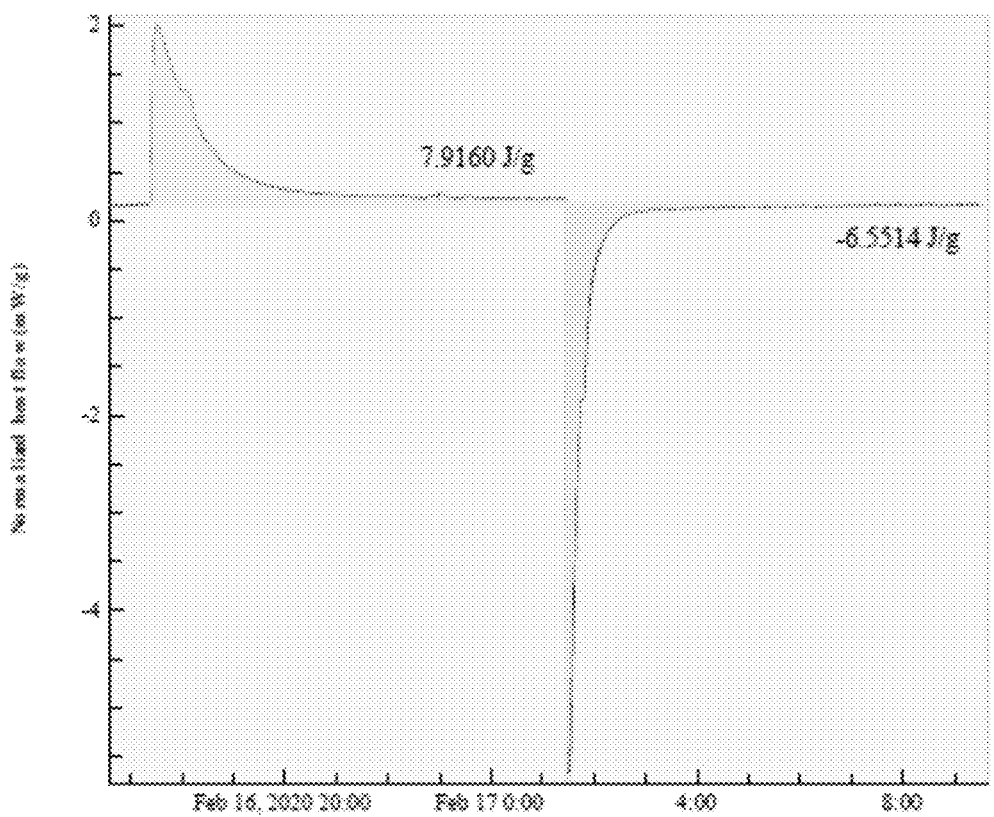
FIG. 62 shows adsorption & desorption for 119 #008C (50:50) after one month of conditioning at 25° C./60% RH from Example 4.

The particle size distribution (PSD) analysis of the micronized material, Spray Dried Formulation and Carrier Based formulation conditioned at 40° C./75% RH and 25° C./60% RH is shown in FIGS. 58 and 59 respectively. These data are also summarised in Table 34.

TABLE 34

Particle size distribution of micronized Imatinib, Spray Dried Formulation and Carrier Based formulation after 1M at 40° C./75% RH and 25° C./60% RH

| Dispersing Conditions | | $d_{10}$/μm (SDev) | $d_{50}$/μm (SDev) | $d_{90}$/μm (SDev) |
|---|---|---|---|---|
| Micronized material-NP-106-104-M2 | | | | |
| @25° C./60% RH | 4 bar | 0.50 | 1.61 | 3.45 |
| @40° C./75% RH | 4 bar | 0.50 | 1.68 | 3.48 |
| Formulation NP-106-18104-002 (50 ML001:50 API) | | | | |
| T = 0 | 4 bar | 0.39 | 1.48 | 3.54 |
| @25° C./60% RH | 4 bar | 0.46 | 1.70 | 3.83 |
| @40° C./75% RH | 4 bar | 0.47 | 1.74 | 3.80 |
| Spray Dried Formulation #119-008A (75:25) | | | | |
| T = 0 | 4 bar | 0.59 | 2.13 | 4.27 |
| @25° C./60% RH | 4 bar | 0.60 | 2.07 | 4.30 |
| @40° C./75% RH | 4 bar | 0.62 | 2.19 | 4.61 |
| Spray Dried Formulation #119-008B (90:10) | | | | |
| T = 0 | 4 bar | 0.47 | 1.90 | 3.60 |
| @25° C./60% RH | 4 bar | 0.52 | 1.92 | 3.66 |
| @40° C./75% RH | 4 bar | 0.52 | 1.96 | 3.72 |
| Spray Dried Formulation #119-008C (50:50) | | | | |
| T+320 | 4 bar | 0.79 | 2.49 | 5.69 |
| @25° C./60% RH | 4 bar | 0.83 | 2.55 | 5.70 |
| @40° C./75% RH | 4 bar | 0.77 | 2.55 | 5.76 |

For all batches, the powder appeared free flowing, with no obvious hardening/aggregation. The particle size of the 119 #008A/B/C T=1M samples were largely similar to T=0. All summary data have been reported in table 35 below.

TABLE 35

Specific surface area (SSA) analyzed by BET of micronized Imatinib, Spray Dried Formulations and Carrier-Based DPI.

| Conditions | API:Leucine ratio (% w/w) | Sample Mass (g) | SSA ($m^2$/g) | Mean SSA ($m^2$/g) | Std. Dev | % RSD | Tot. Surface ($m^2$) |
|---|---|---|---|---|---|---|---|
| Micronized material - NP-106-104-M2 | | | | | | | |
| @40° C./ 75% RH | 100% | 0.3370 | 5.0367 | 5.0513 | 0.02 | 0.41 | 1.70 |
| | | 0.3318 | 5.0659 | | | | 1.68 |
| @25° C./ 60% RH | | 0.3291 | 5.7357 | 5.7757 | 0.06 | 0.98 | 1.89 |
| | | 0.3239 | 5.8157 | | | | 1.88 |
| 119#008A | | | | | | | |
| 119#008A | 75:25 | 0.3493 | 13.8895 | 13.9704 | 0.11 | 0.82 | 4.85 |
| | | 0.3406 | 14.0512 | | | | 4.79 |
| @25° C./ 60% RH @40° C./ 75% RH | 75:25 | | | | | | |
| 119#008B | | | | | | | |
| T = 0 | 90:10 | 0.3670 | 9.6732 | 9.5914 | 0.12 | 1.21 | 3.55 |
| | | 0.3444 | 9.5095 | | | | 3.28 |
| @25° C./ 60% RH | 90:10 | | | | | | |

TABLE 35-continued

Specific surface area (SSA) analyzed by BET of micronized Imatinib, Spray Dried Formulations and Carrier-Based DPI.

| Conditions | API:Leucine ratio (% w/w) | Sample Mass (g) | SSA (m$^2$/g) | Mean SSA (m$^2$/g) | Std. Dev | % RSD | Tot. Surface (m$^2$) |
|---|---|---|---|---|---|---|---|
| @40° C./75% RH | | | | | | | |
| 119#008C | | | | | | | |
| T = 0 | 50:50 | 0.3545 | 21.9505 | 21.9085 | 0.06 | 0.27 | 7.78 |
|  |  | 0.3472 | 21.8665 |  |  |  | 7.59 |
| @25° C./60% RH | 50:50 | | | | | | |
| @40° C./75% RH | | | | | | | |
| NP-106-18104-002 | | | | | | | |
| T = 0 | 50:50 | 0.3605 | 3.4106 | 3.4148 | 0.01 | 0.17 | 1.23 |
|  | 50:50 | | | | | | |

Isothermal Perfusion Calorimetry Performed by TAM (Thermal Activity Monitor)

TAM analysis was performed all drug substance material. Analysis was conducted for 6 hours at 0% RH and for 8 hrs at 90% RH. The system was brought back down to 0% RH for a final 8 hours. The wetting (adsorption) and drying (desorption) thermogram over time are shown in FIGS. 58-59 for the micronized material (NP-106-104-M2) after 1 Month of conditioning at 25° C./60% RH and 40° C./75% RH, The area under the curve (AUC) of the wetting peak is representative of the enthalpy of re-crystallisation. The AUC of the wetting peak for the micronized, from 9.4-9.8 J/g. These data suggested that the amorphous content of all system was similar. Further work using this method is advised with unmicronized material to determine the amount of amorphicity in these systems. Our current understanding is that the amorphous content is below the limit of quantification.

DSC Analysis of Micronized API, Spray Dried Formulations and Carrier Based DPI Formulation

A. Micronized API

Figure 64:
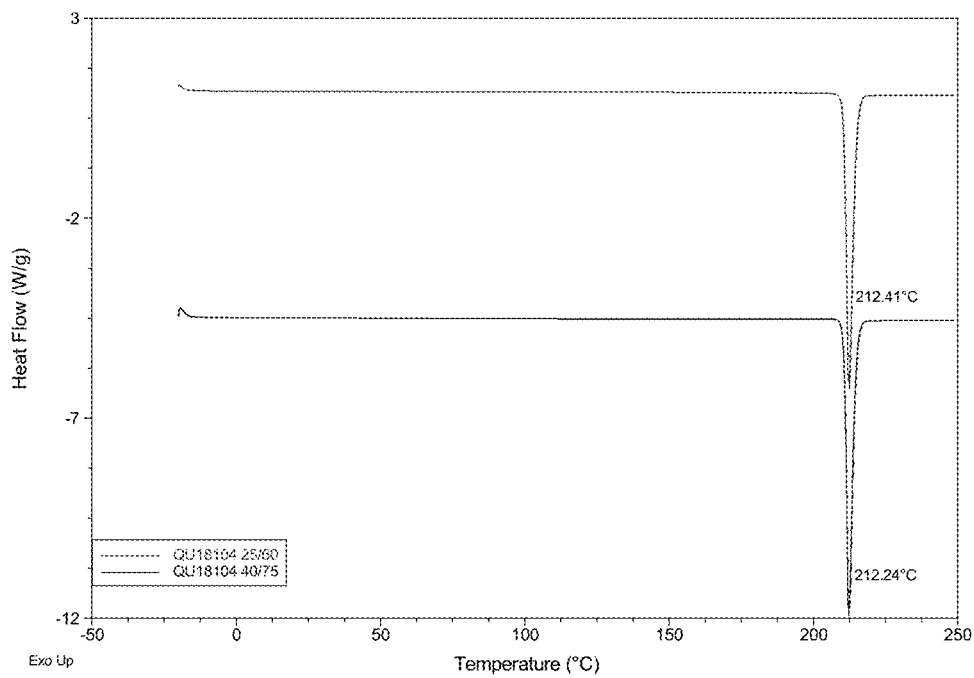
FIG. 64 shows an overlaid DSC thermogram of the first heat cycle for batch NP-106-104-M2 after one month conditioning at 25° C./60% RH and at 40° C./75% RH from Example 4.
Figure 65:
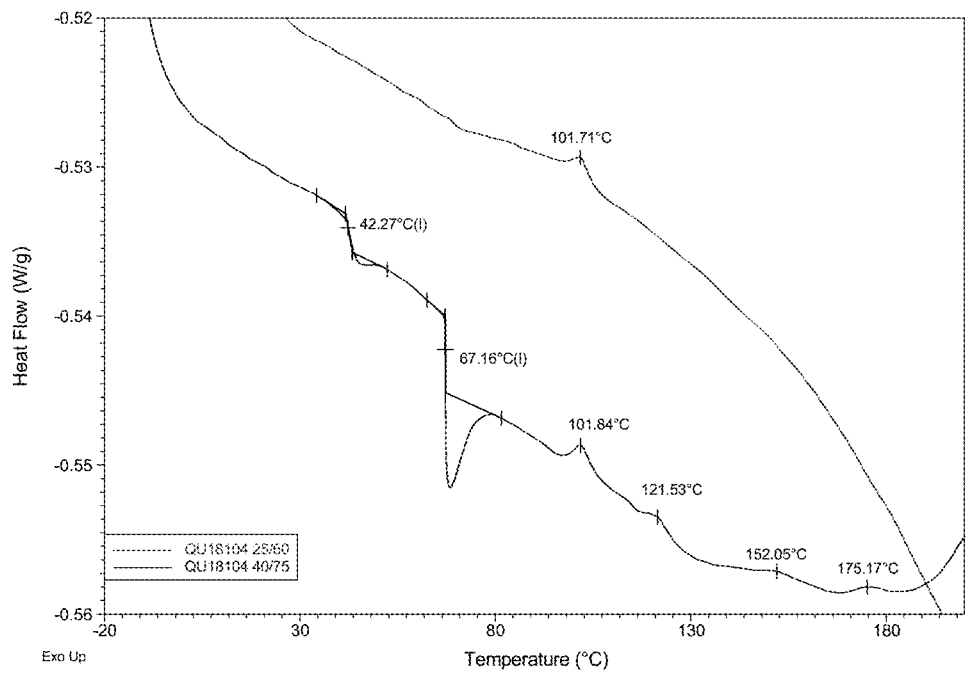
FIG. 65 shows an overlaid DSC thermogram of the magnified first heat cycle for batch NP-106-104-M2 after conditioning at 25° C./60% RH and at 40° C./75% RH (1M) from Example 4.
Figure 66:
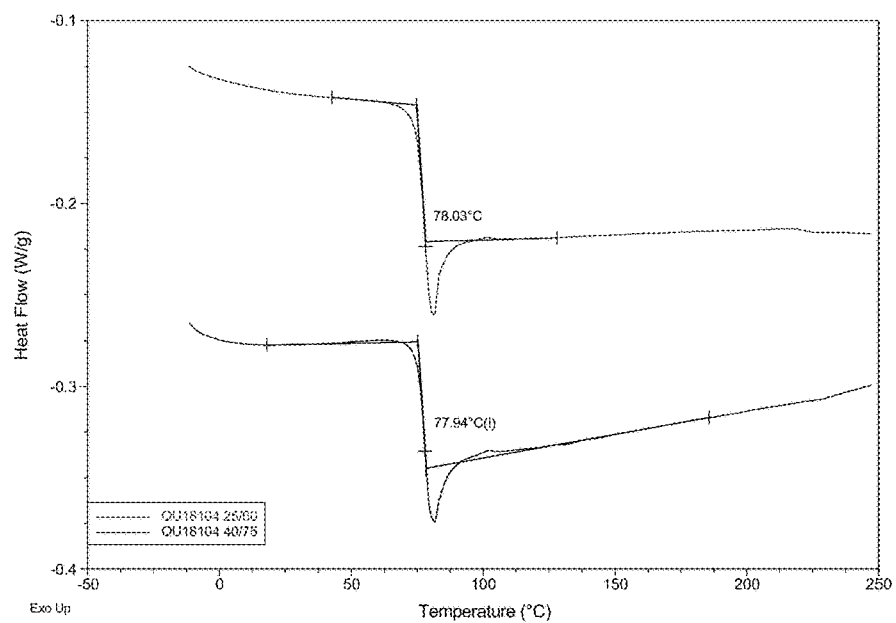
FIG. 66 shows an overlaid DSC thermogram of the second heat cycle for batch NP-106-104-M2 after conditioning at 25° C./60% RH and at 40° C./75% RH (1M) from Example 4.
Figure 67:
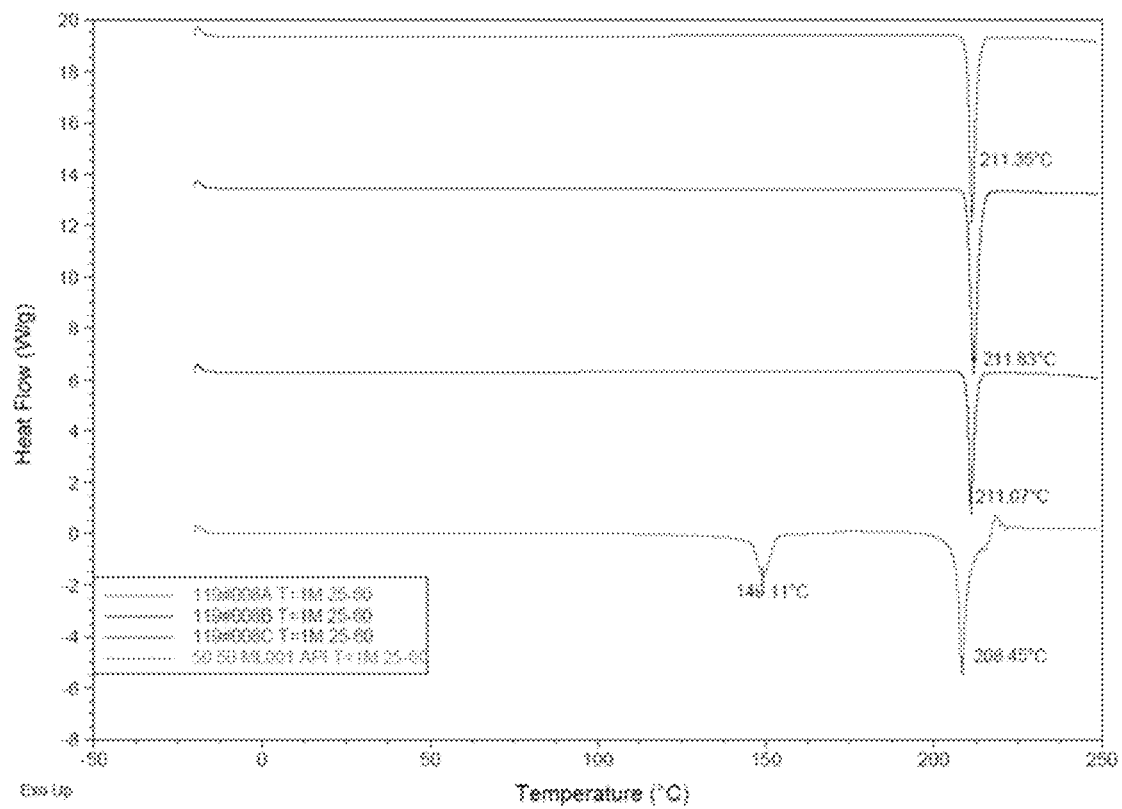
FIG. 67 shows overlaid DSC traces of the first heat cycle for batches 119 #008A-C, NP-106-104-002 after conditioning at 25° C./60% RH from Example 4.
Figure 68:
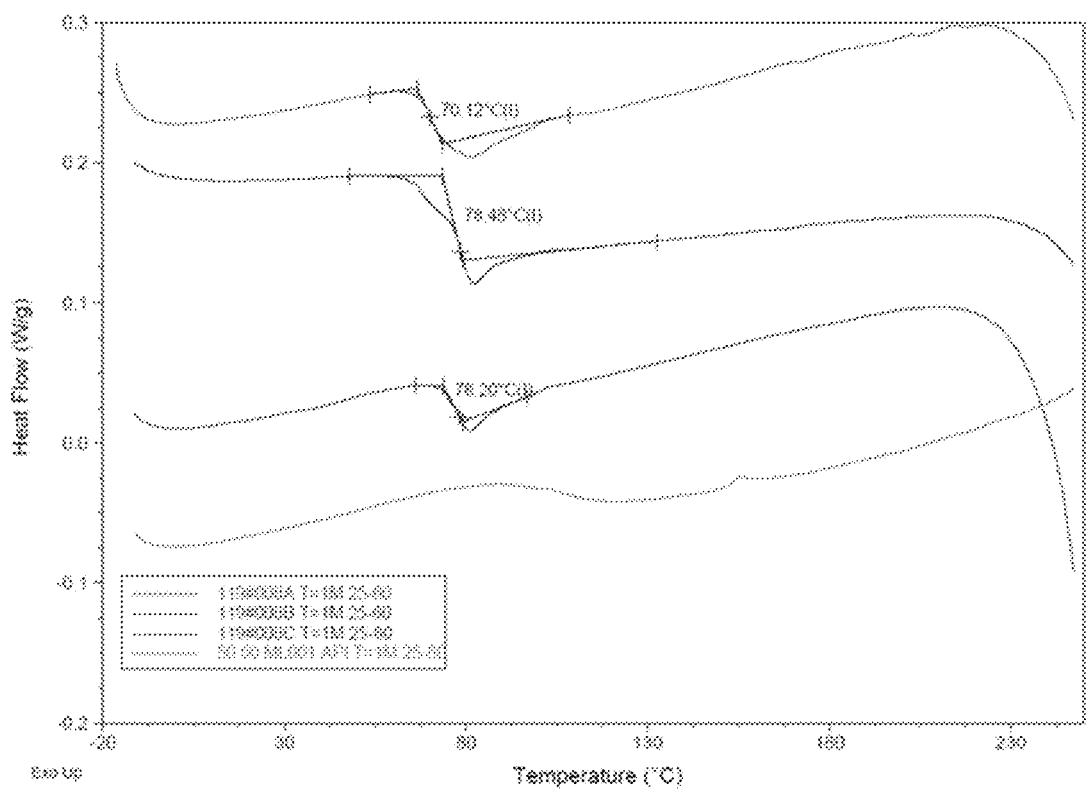
FIG. 68 shows overlaid DSC traces of the second heat cycle for batches 119 #008A-C, NP-106-104-002 after conditioning at 25° C./60% RH from Example 4.
Figure 69:
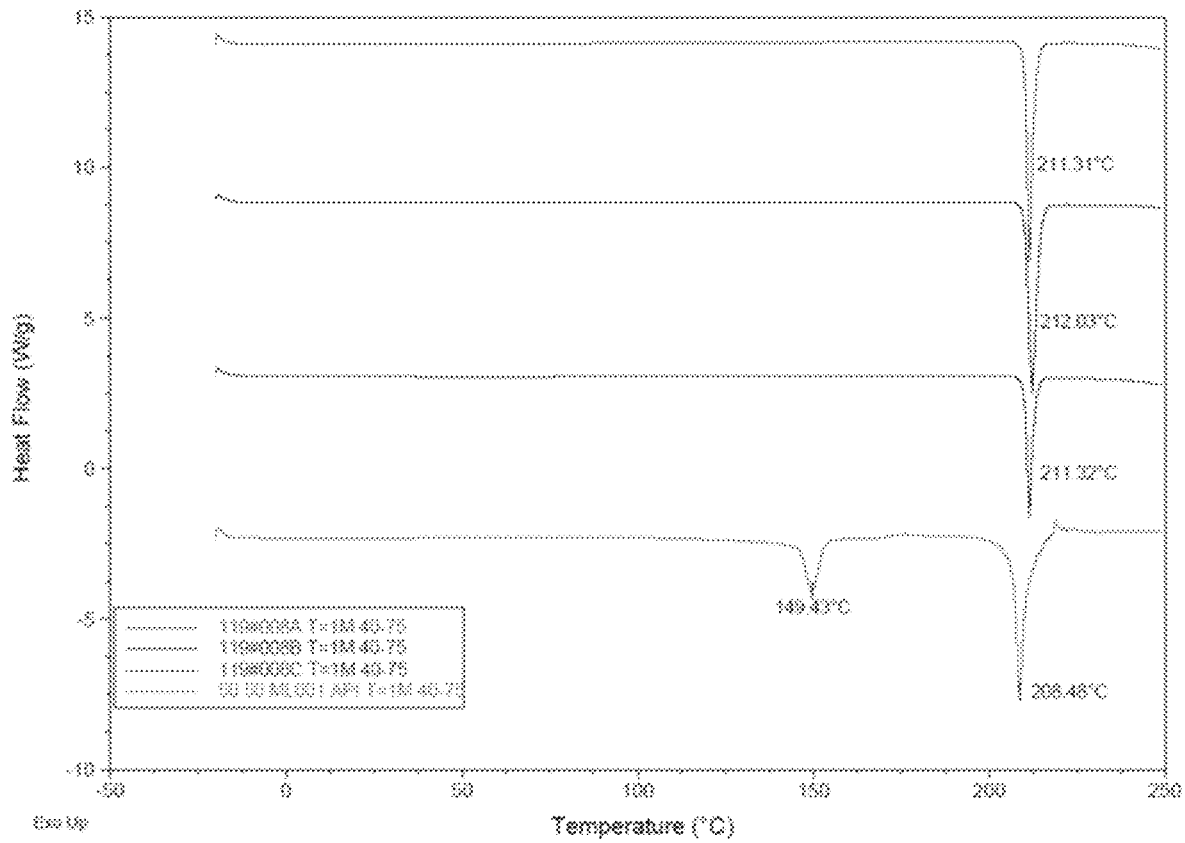
FIG. 69 shows overlaid DSC traces of the first heat cycle for batches 119 #008A-C, NP-106-104-002, after conditioning at 40° C./75% RH from Example 4.
Figure 70:
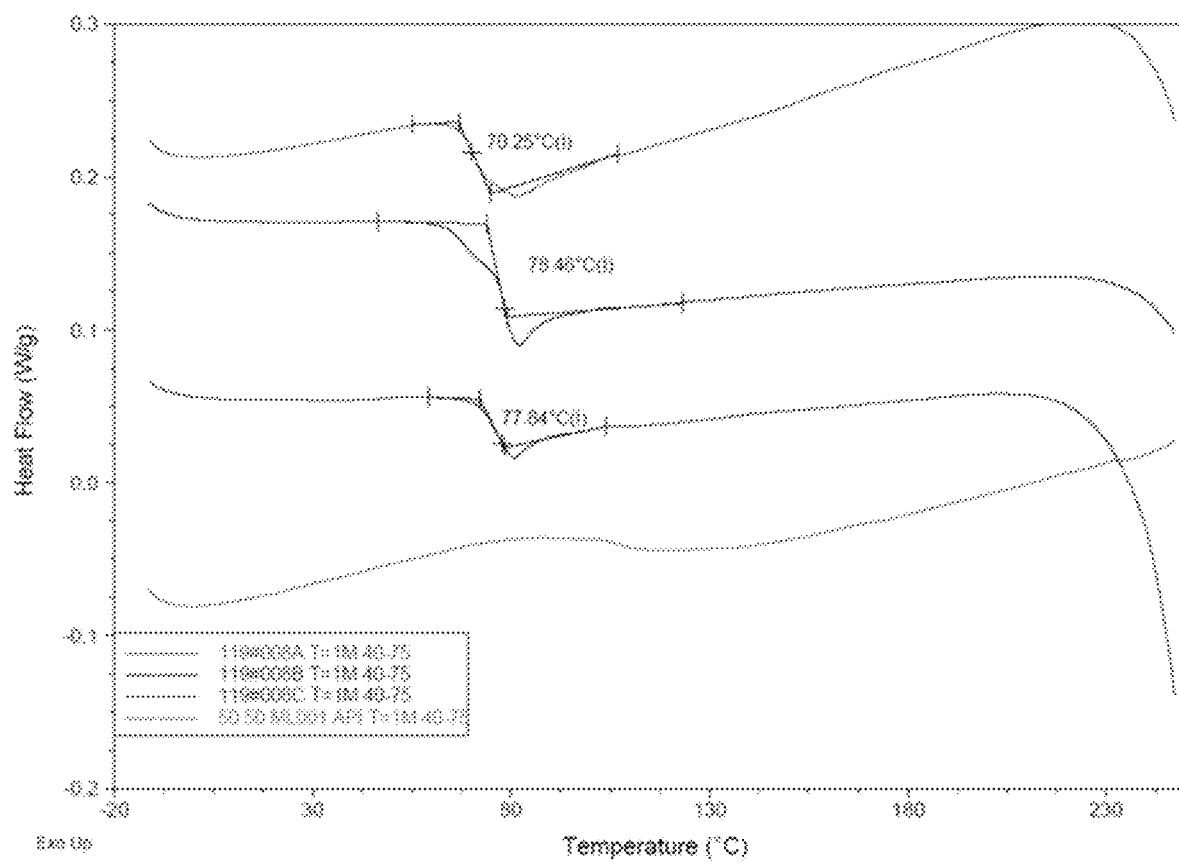
FIG. 70 shows overlaid DSC traces of the second heat cycle for batches 119 #008A-C, NP-106-104-002, after conditioning at 40° C./75% RH from Example 4.

The stability samples were analysed by DSC according to the method described in the method section above. Overlaid traces of the first heat cycle, magnified first heat cycle and second heat cycle can be seen in FIGS. 64-66 respectively.

The first heat cycle for NP-106-104-M2 25/60 displayed a sharp melt event at 212° C. relating to Imatinib. There also appeared to be a very small crystallisation event at 101.7° C. which suggested that there was a small amount of amorphous material within the sample. The second heat cycle displayed a Tg at 78.0° C. This was a result of the imatinib being quench cooled during the cooling phase of the run.

The first heat cycle for NP-106-104-M2 40/75 also displayed a sharp melt event at 212° C. relating to imatinib. A series of very weak glass transitions at 42.3 & 67.2° C. followed by equally small crystallisation events at 101.8, 121.5, 152.1 & 175.2° C. were also observed in the first heat cycle. This again suggested there was a very small amount of amorphous material within the sample. The second heat cycle displayed a Tg at 78.0° C., which was a result of the NP-106 being quench cooled during the cooling phase of the run.

B. Spray Dried Formulations and Carrier-Based DPI

The stability samples were analysed by DSC according to the method described in method section. Overlaid traces of the first heat cycle and second heat cycle for samples stored at 25° C./60% RH and 40° C./75% RH can be seen in FIGS. 67-70.

As observed at T=0, the DSC thermograms for batches 119 #008A-C, stored at 25° C./60% RH (FIGS. 67) and 40° C./75% RH (FIG. 69), the first heating cycle displayed an event at ~211-212° C. which was related to the melting of imatinib. Again, the temperature at which the melt occurred appeared to decrease subtly with increasing leucine content. The second heating cycle for these samples displayed a glass transition for each of the formulations at a temperature of ~70-80° C. There appears to be little impact of storage on these samples. On close examination of the baseline, very small events are observed. These will be interpreted fully along 3-month data, but may indicate a very small amount of amorphous material.

For batch NP-106-104-002, the DSC thermograms were largely similar to the observations at T=0. The first heating cycle displaying two key endothermic events, at ~149° C. and a second, broader event at ~208° C. There was possibly a very weak Tg observed again at ~101° C. exhibited in the second heating cycle, although it was difficult to discern from the baseline.

Figure 63:
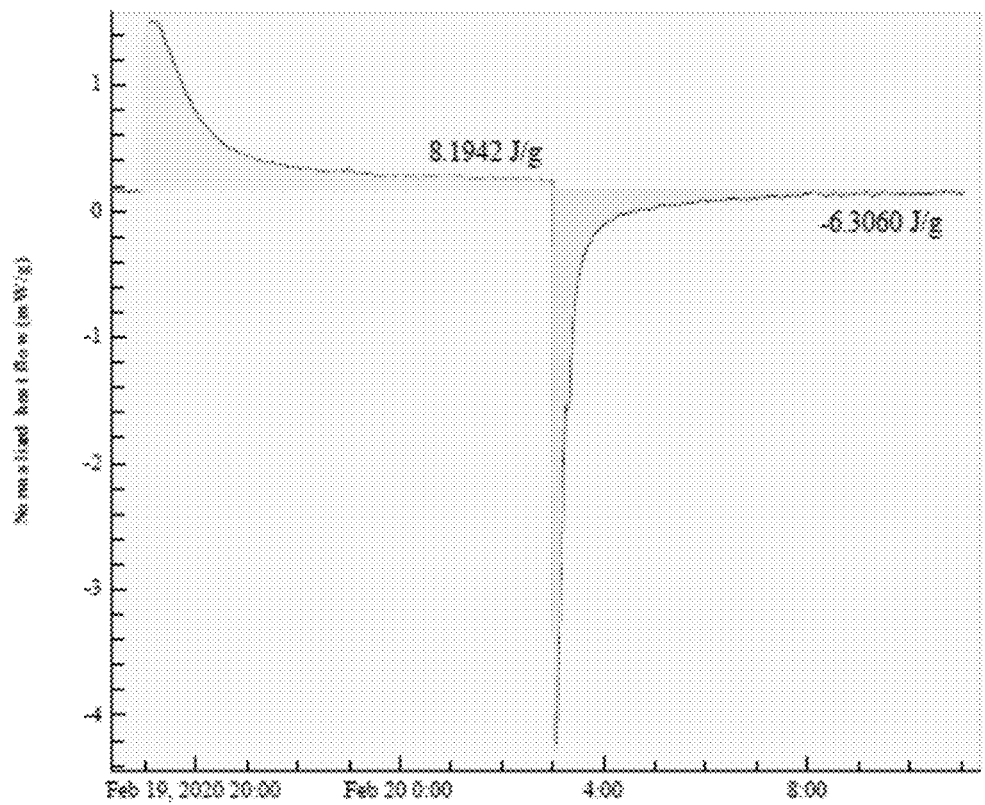
FIG. 63 shows adsorption & desorption for NP-106-104-002 after one month of conditioning at 25° C./60% RH from Example 4.
Figure 71:
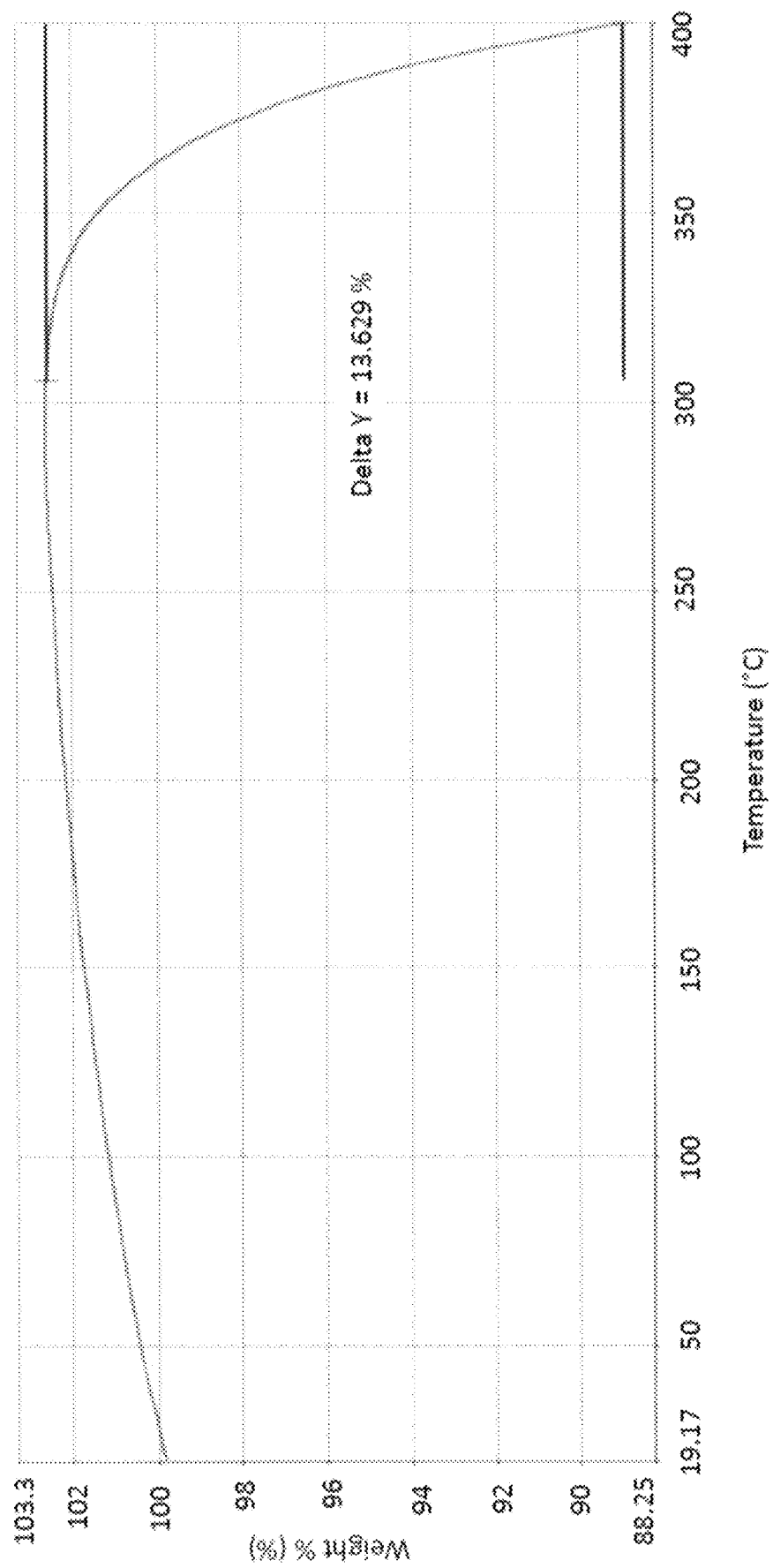
FIG. 71 shows a TGA thermogram of NP-106-104-M2 after conditioning at 40° C./75% RH from Example 4.
Figure 72:
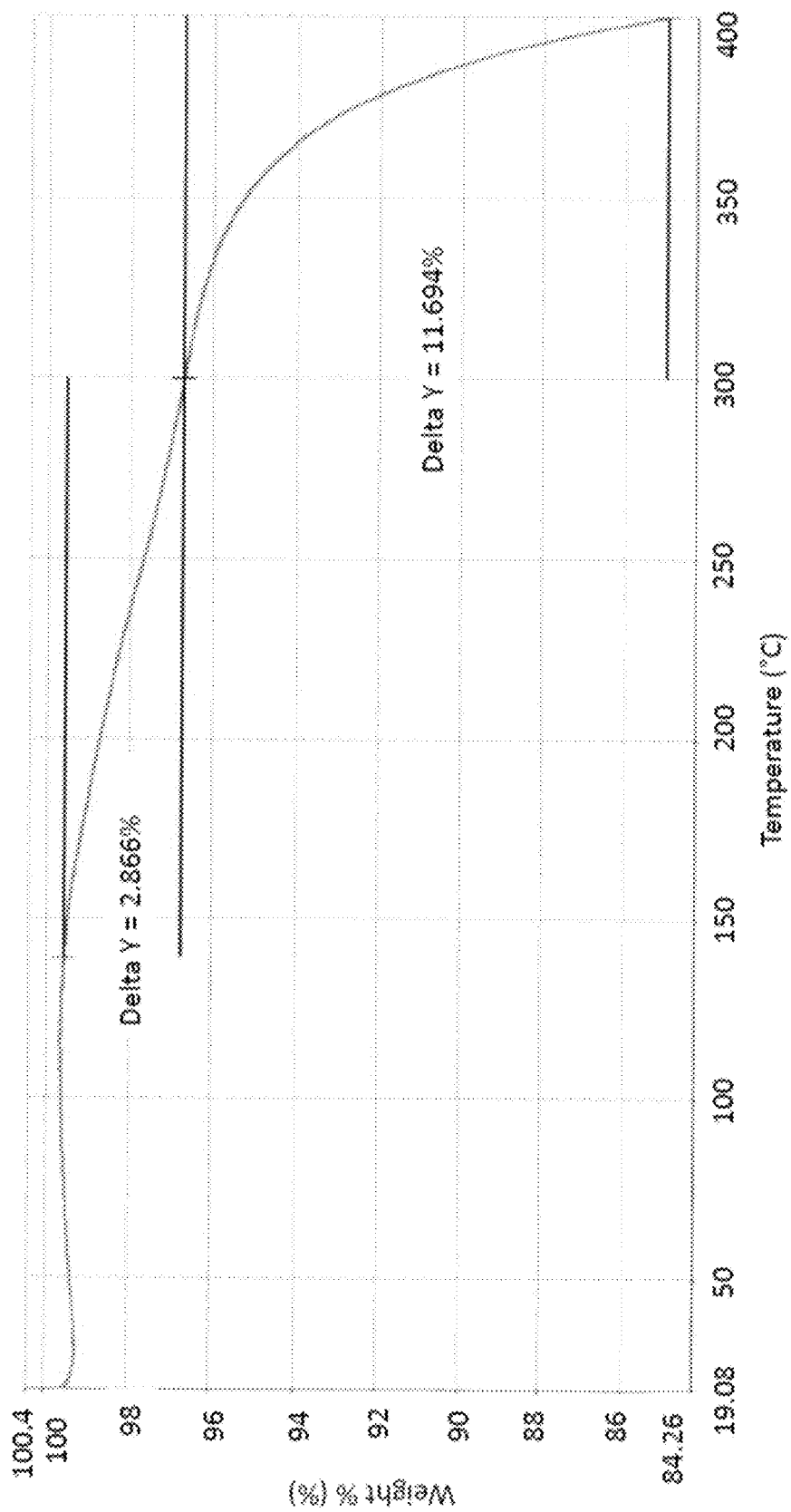
FIG. 72 shows a TGA thermogram of NP-106-104-M2 after conditioning at 25° C./60% RH from Example 4.

Thermal Gravimetric Analysis for Carrier Based DPI Formulation and Spray Dried Formulations As seen in FIG. 63, the thermogram of NP-106-104-M2 at 40° C./75% RH (FIG. 71) shows degradation of the sample starts at Ca. 300° C. with no prior mass loss. The thermogram for NP-106-104-M2 at 25° C./60% RH (FIG. 72) shows an initial steady mass loss of Ca. 3% from 150-300° C. followed by degradation at Ca. 300° C.

DVS Analysis of Micronized API, SprayDried Formulations and Carrier Based DPI Sorption/desorption (DVS) analysis was performed on the stability samples according to the method described in method section above.

A. Micronized API

Figure 73:
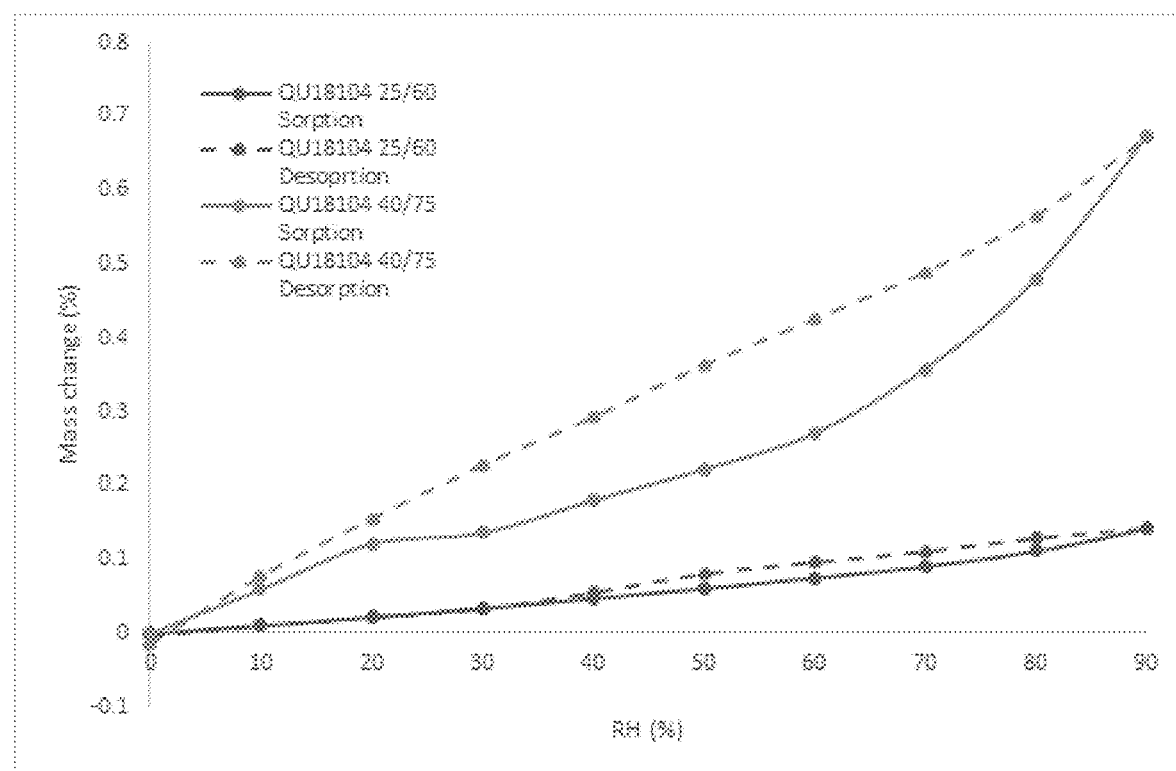
FIG. 73 shows overlaid hysteresis plots for batch NP-106-104-M2 after conditioning at 25° C./60% RH and 40° C./75% RH from Example 4.
Figure 74:
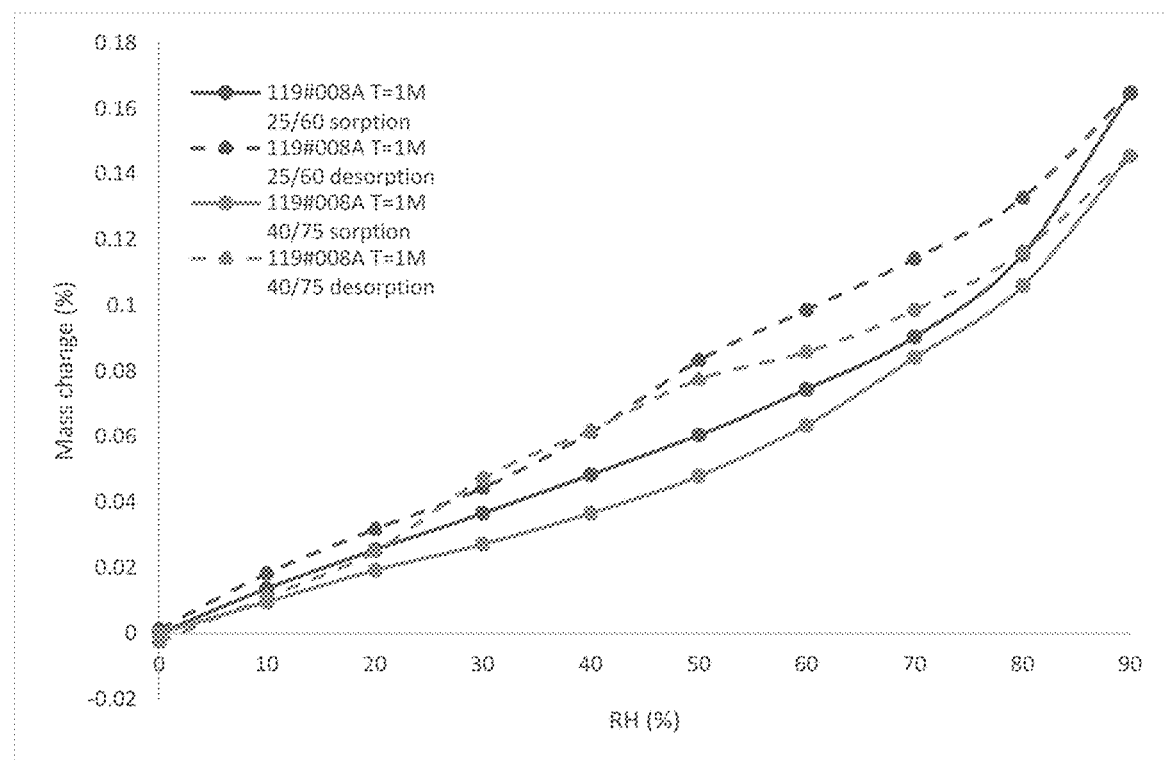
FIG. 74 shows overlaid hysteresis plots for batch 119 #008A (75:25) after conditioning at 25° C./60% RH and 40° C./75% RH from Example 4.
Figure 75:
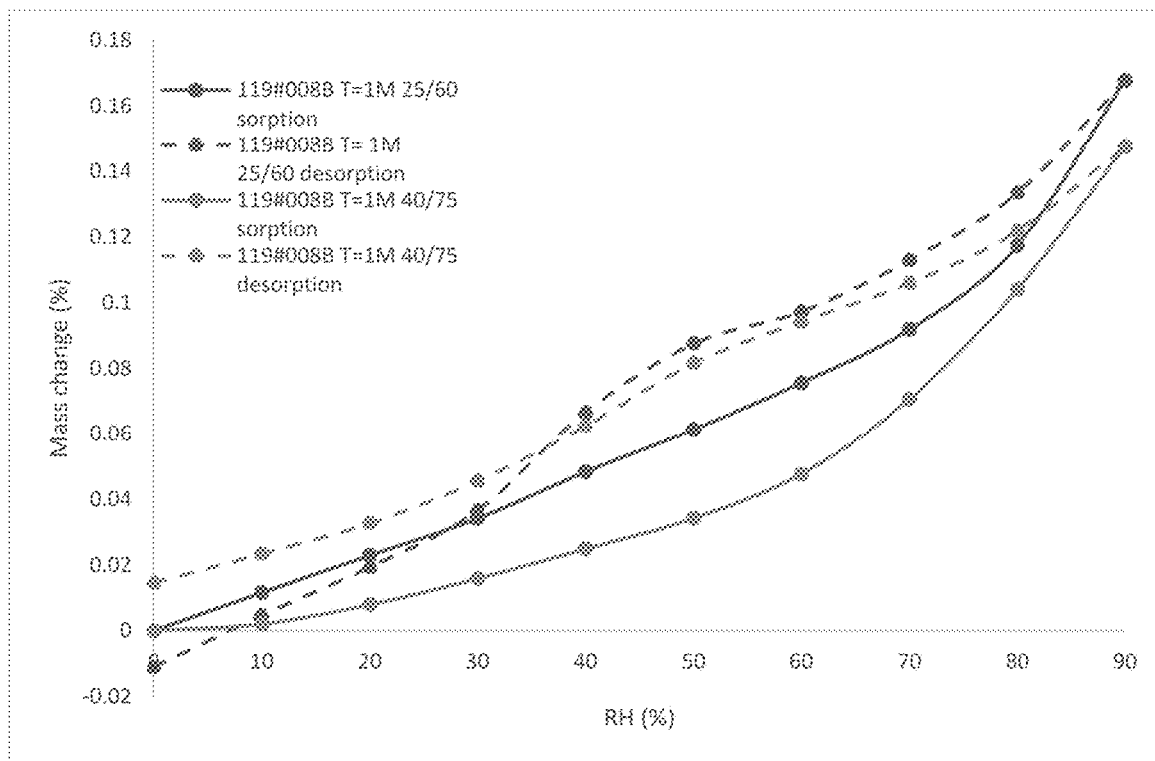
FIG. 75 shows overlaid hysteresis plots for batch 119 #008B (90:10) after conditioning at 25° C./60% RH and 40° C./75% RH from Example 4.
Figure 76:
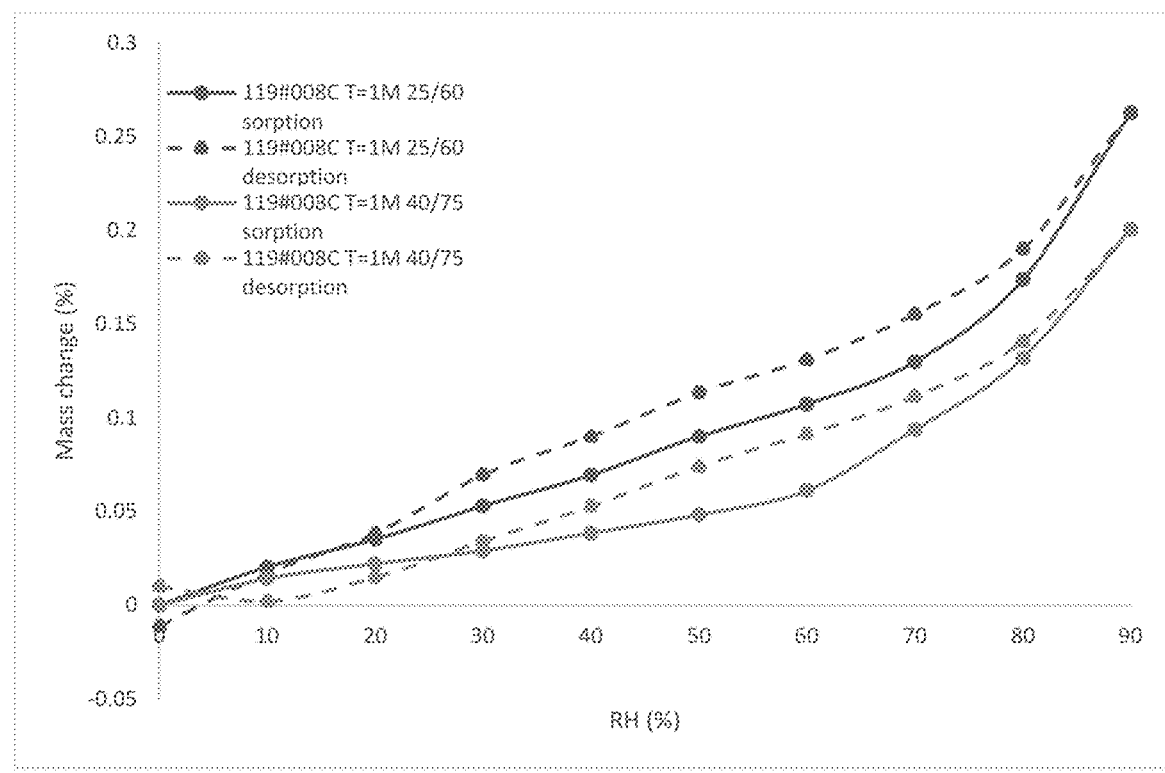
FIG. 76 shows overlaid hysteresis plots for batch 119 #008C (50:50) after conditioning at 25° C./60% RH and 40° C./75% RH from Example 4.
Figure 77:
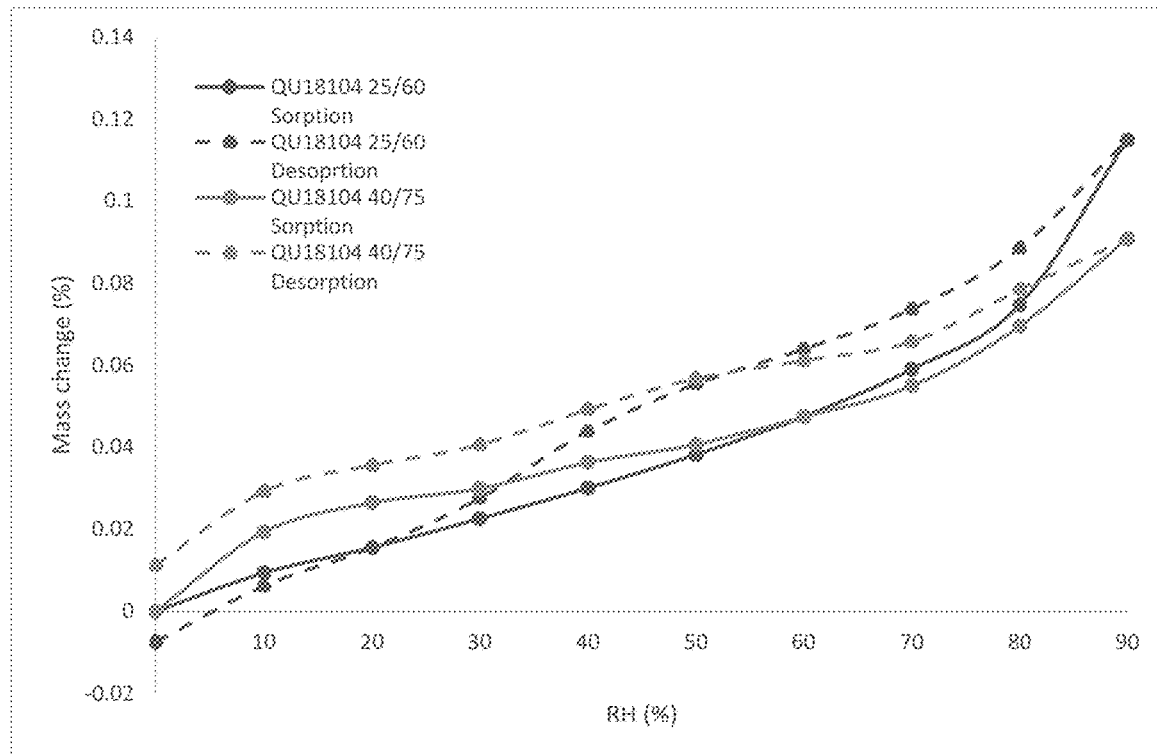
FIG. 77 shows overlaid hysteresis plots for batch NP-106-104-002 after conditioning at 25° C./60% RH and 40° C./75% RH from Example 4.

An overlaid hysteresis plot for batches NP-106-104-M2 at 25° C./60% RH and NP-106-104-M2 at 40° C./75% RH can be seen in FIG. 73.

Both samples took on very little moisture during testing. NP-106-104-M2 at 25° C./60% RH experienced a mass increase of 0.14% at 90% RH during the sorption phase of the analysis, whilst the mass of NP-106-104-M2 at 40° C./75% RH increased by 0.67%. When the RH was reduced back to 0% RH, both samples released all of the moisture they had previously taken up.

Small artefacts can be seen in the % weight change traces of both formulations. These are likely due to vibrations in the surrounding area of the instrument and appear exaggerated due to the small scale of each trace.

B. Spray Dried Formulations and Carrier-Based DPI

Data shows that all formulations remained largely unchanged following storage at either at 25° C./60% RH or at 40° C./75% RH for 1 month. See FIGS. 74-77.

XRPD Analysis of Micronized API, SprayDried Formulations and Carrier Based DPI Formulation

Micronized API

XRPD analysis was performed on the bulk micronized material, labelled as NP-106-104-M2 and according to the method described in the method section above.

Figure 78:
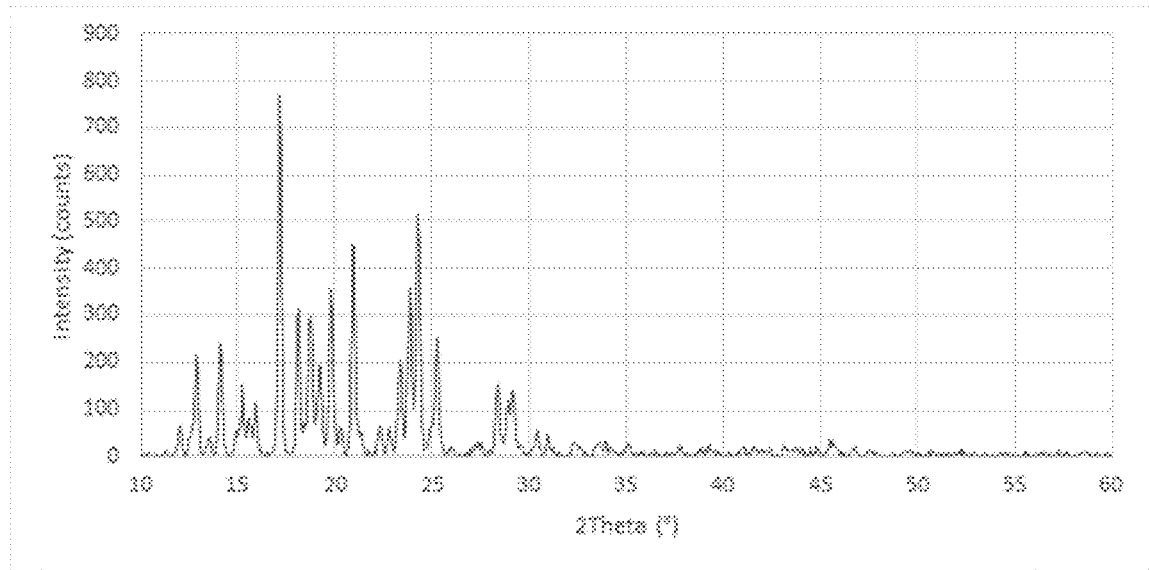
FIG. 78 shows a background subtracted XRPD trace of batch NP-106-104-M2 after conditioning for 1 month at 25° C./60% RH from Example 4.
Figure 79:
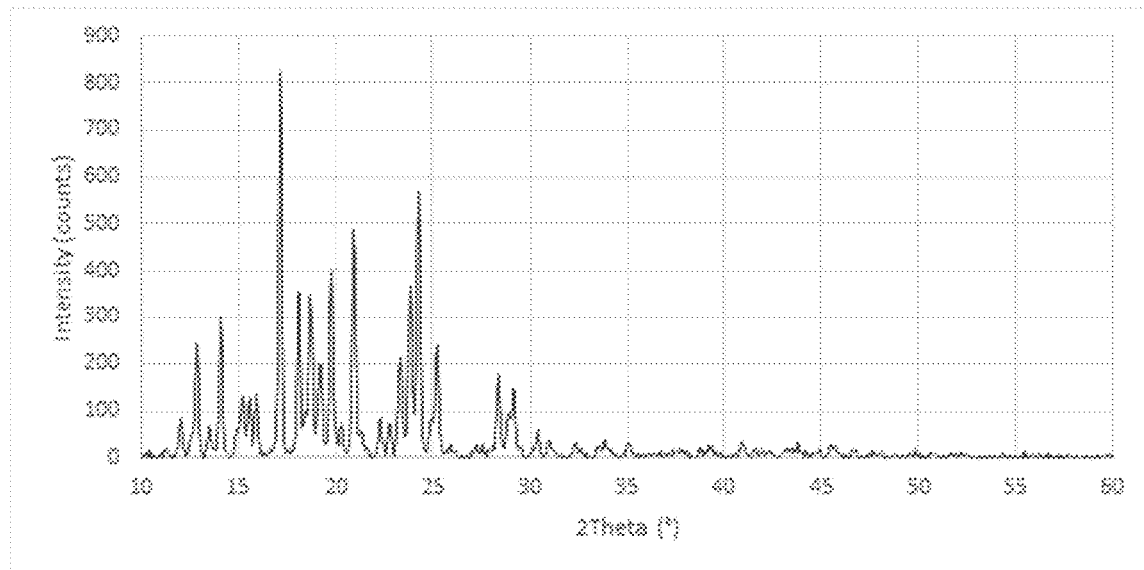
FIG. 79 shows a background subtracted XRPD trace of batch NP-106-104-M2 after conditioning for 1 month at 40° C./75% RH from Example 4.
Figure 80:
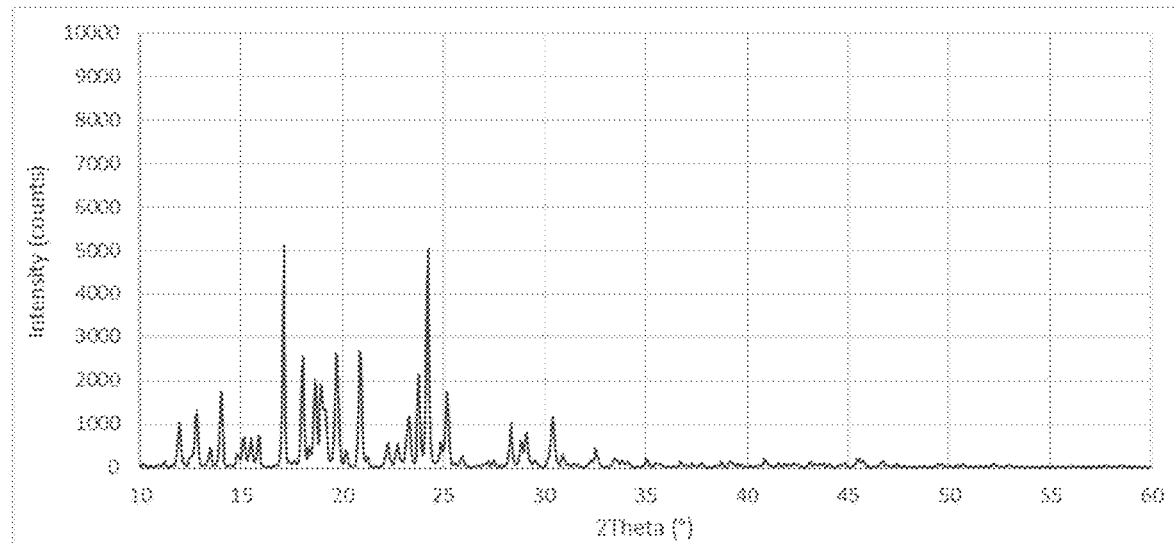
FIG. 80 shows a background subtracted XRPD trace of batch 119 #008A (75:25) after conditioning at 25° C./60% RH from Example 4.
Figure 81:
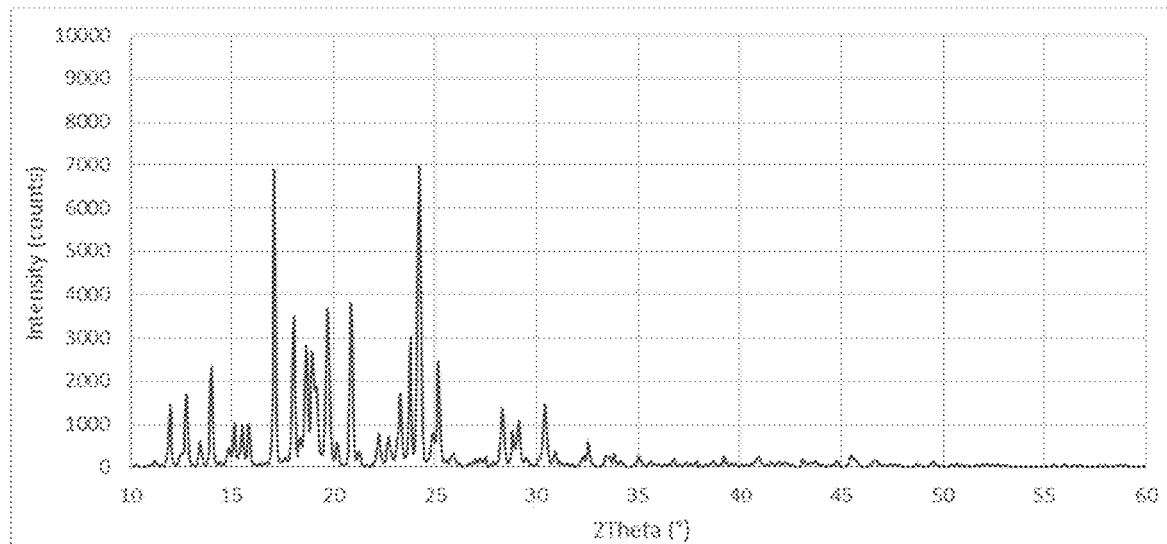
FIG. 81 shows a background subtracted XRPD trace of batch 119 #008A (75:25) after conditioning at 40° C./75% RH from Example 4.
Figure 82:
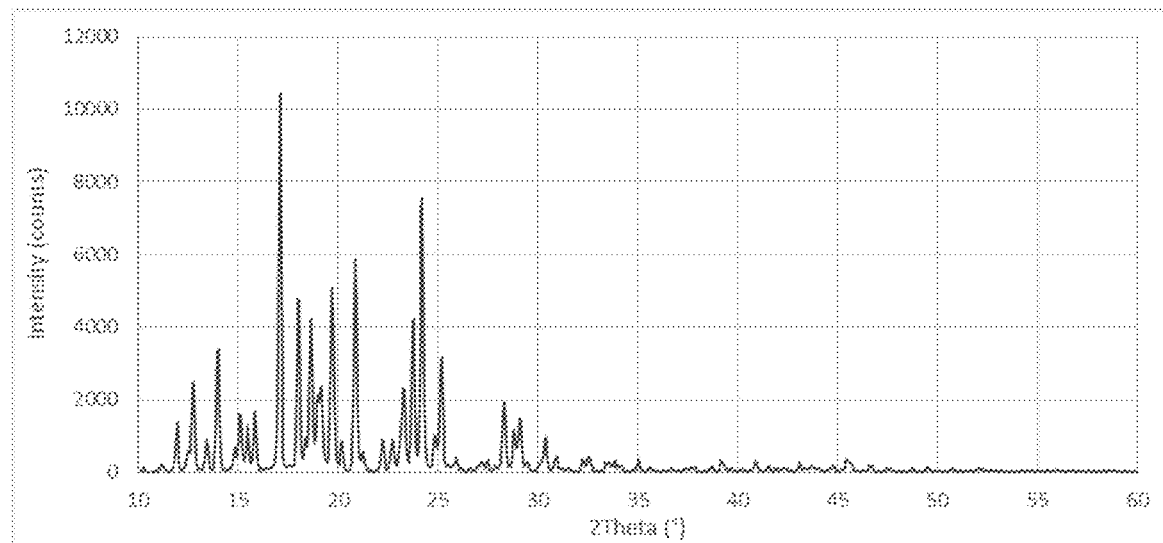
FIG. 82 shows a background subtracted XRPD trace of batch 119 #008B (90:10) after conditioning at 25° C./60% RH from Example 4.
Figure 83:
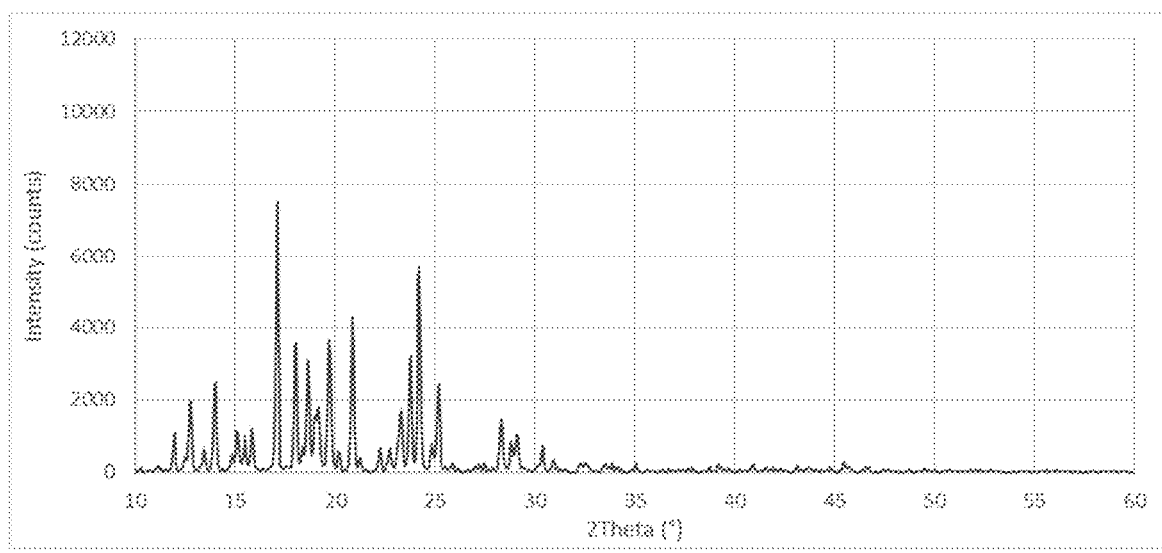
FIG. 83 shows a background subtracted XRPD trace of batch 119 #008B (90:10) after conditioning at 40° C./75% RH from Example 4.
Figure 84:
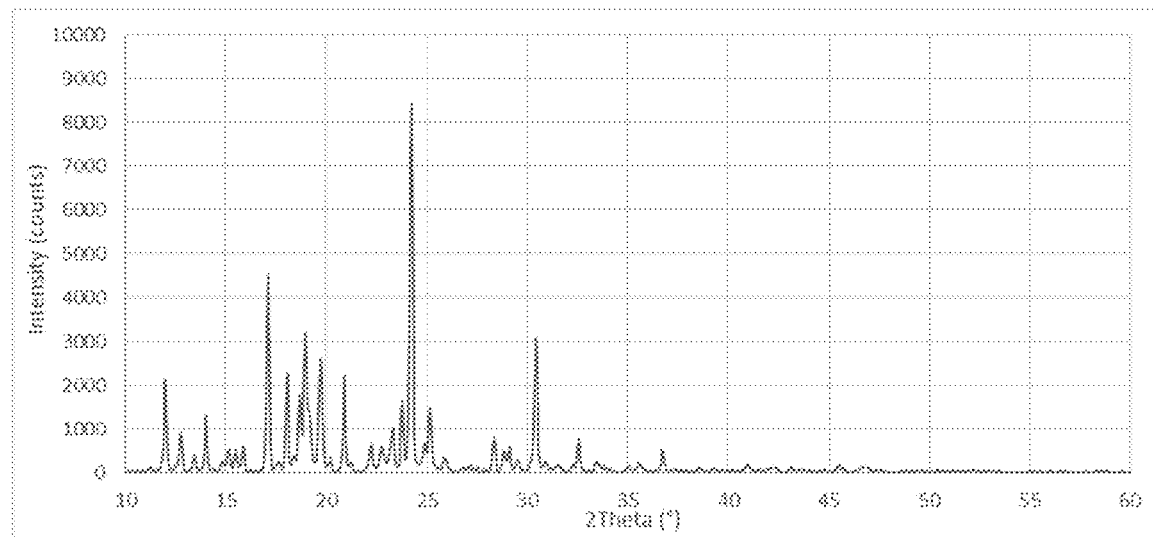
FIG. 84 shows a background subtracted XRPD trace of batch 119 #008C (50:50) after conditioning at 25° C./60% RH from Example 4.
Figure 85:
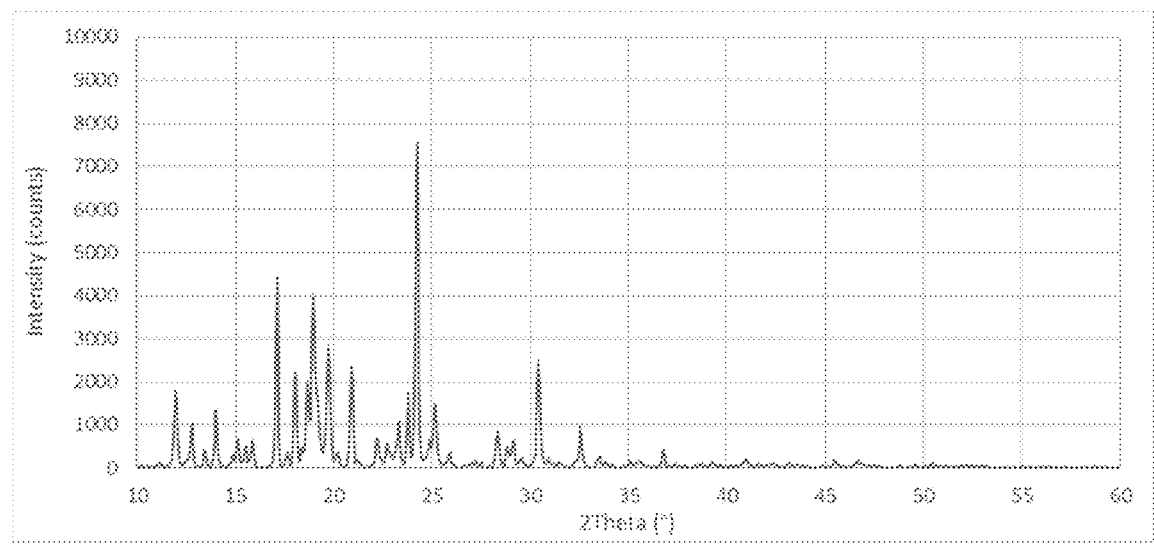
FIG. 85 shows a background subtracted XRPD trace of batch 119 #008C (50:50) after conditioning at 40° C./75% RH from Example 4.
Figure 86:
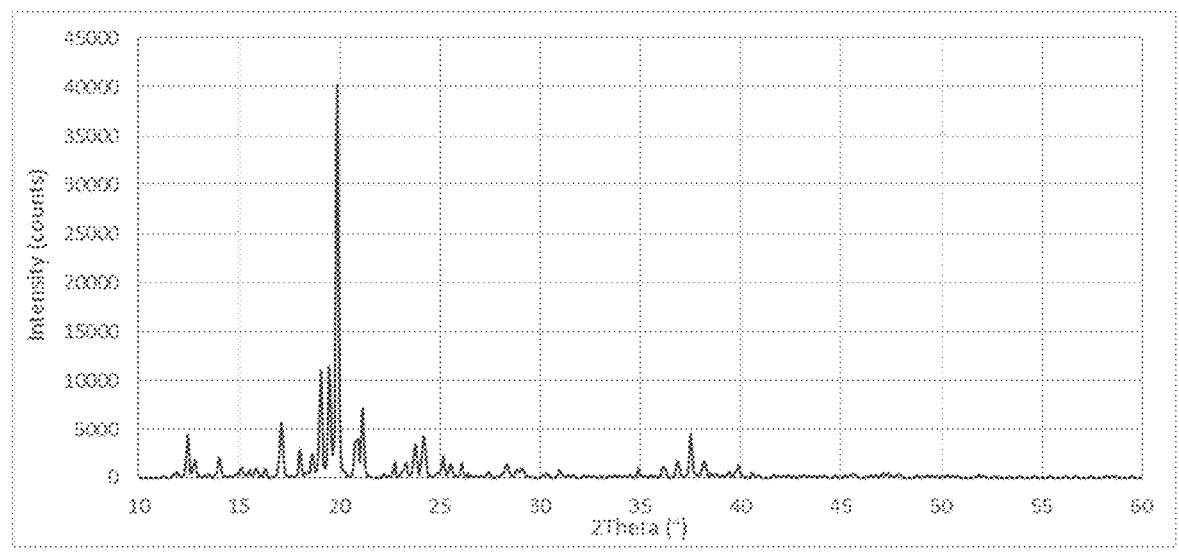
FIG. 86 shows a background subtracted XRPD trace of NP-106-104-002 after conditioning at 25° C./60% RH from Example 4.
Figure 87:
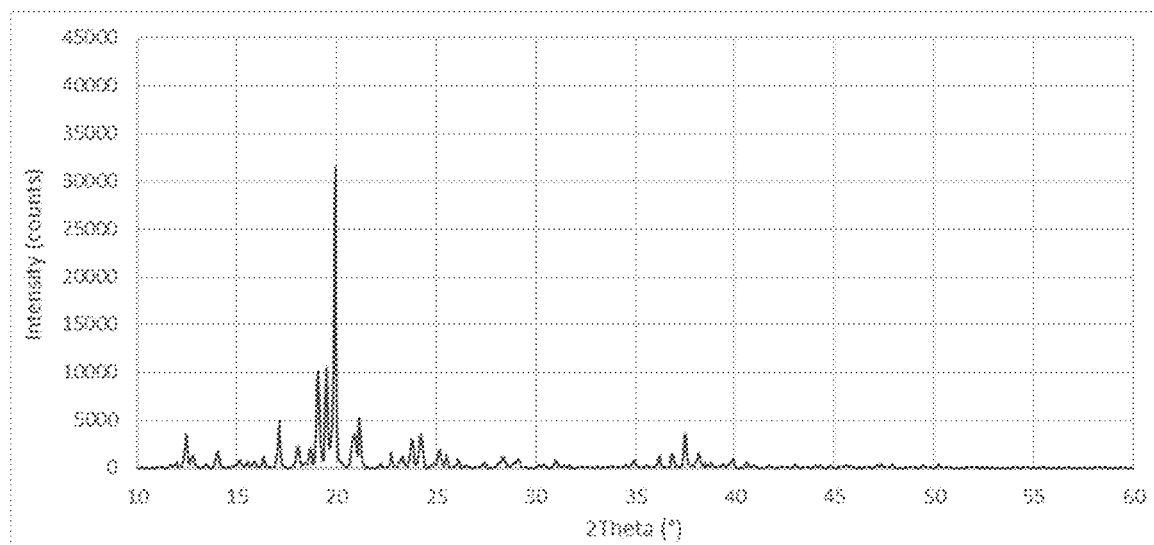
FIG. 87 shows a background subtracted XRPD trace of NP-106-104-002 after conditioning at 40° C./75% RH from Example 4.

The background subtracted traces for NP-106-104-M2 25° C./60% RH and NP-106-104-M2 40° C./75% RH can be seen in FIGS. 78 and 79 respectively. Both formulations appeared to be largely crystalline.

Spray Dried and Carrier-Based Formulations

All the formulations appeared to be predominately crystalline after 1-month storage at both conditions. The background subtracted traces for Spray Dried and Carrier-Based DPI formulations at 25° C./60% RH and 40° C./75% RH can be seen in FIGS. 80-87.

What is claimed is:

1. An inhalable formulation consisting of 100% micronized imatinib or a salt thereof, wherein greater than 80% of the micronized imatinib or salt thereof in the inhalable formulation is present in a single crystal form.

2. The inhalable formulation of claim 1, wherein the inhalable formulation is a dry powder.

3. The inhalable formulation of claim 1, wherein the imatinib or salt thereof is present in a therapeutically effective amount to treat a condition of the pulmonary cardiovascular system.

4. The inhalable formulation of claim 3, wherein the condition of the pulmonary cardiovascular system is pulmonary arterial hypertension (PAH).

5. The inhalable formulation of claim 1, wherein the salt is at least one selected from the group consisting of glycolate, malate, tartrate, malonate, isethionate, and citrate.

6. A method of treating a condition of the pulmonary cardiovascular system, the method comprising providing to a subject an inhalable formulation consisting of 100% micronized imatinib or a slat thereof, wherein greater than 80% of the micronized imatinib or a slat thereof in the inhalable formulation is present in a single crystal form.

7. The method of claim 6, wherein the inhalable formulation is a dry powder.

8. The method of claim 6, wherein the subject is a human.

9. The method of claim 6, wherein the condition of the pulmonary cardiovascular system is pulmonary arterial hypertension (PAH).

10. The method of claim 6, wherein the salt is at least one selected from the group consisting of glycolate, malate, tartrate, malonate, isethionate, and citrate.

11. The method of claim 6, wherein the single crystal form is type A.

* * * * *